United States Patent
Nosse et al.

(10) Patent No.: US 8,822,471 B2
(45) Date of Patent: Sep. 2, 2014

(54) COMPOUNDS, PHARMACEUTICAL COMPOSITIONS AND USES THEREOF

(75) Inventors: Bernd Nosse, Biberach an der Riss (DE); Andreas Blum, Warthausen (DE); Steffen Breitfelder, Attenweiler (DE); Armin Heckel, Biberach an der Riss (DE); Frank Himmelsbach, Mittelbiberach (DE); Elke Langkopf, Biberach an der Riss (DE); Bernd Wellenzohn, Langenargen (DE); Neil J. Ashweek, Escondido, CA (US); Nicole Harriott, San Diego, CA (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 13/418,376

(22) Filed: Mar. 13, 2012

(65) Prior Publication Data

US 2013/0065906 A1    Mar. 14, 2013

(30) Foreign Application Priority Data

Mar. 14, 2011  (EP) .................................. 11158114

(51) Int. Cl.
| | | |
|---|---|---|
| A61K 31/4545 | (2006.01) | |
| A61K 31/506 | (2006.01) | |
| A61K 31/501 | (2006.01) | |
| C07D 413/14 | (2006.01) | |
| C07D 413/04 | (2006.01) | |
| C07D 417/14 | (2006.01) | |

(52) U.S. Cl.
CPC ............ C07D 413/14 (2013.01); C07D 413/04 (2013.01); C07D 417/14 (2013.01)
USPC .................. 514/252.03; 514/255.05; 514/273

(58) Field of Classification Search
USPC ................................. 514/252.03, 255.05, 273
See application file for complete search history.

(56) References Cited

U.S. PATENT DOCUMENTS

| | | | |
|---|---|---|---|
| 7,659,282 B2 * | 2/2010 | Yakatan et al. ............... | 514/289 |
| 2011/0021491 A1 | 1/2011 | Tran et al. | |
| 2011/0166116 A1 | 7/2011 | Dyck et al. | |
| 2013/0065906 A1 | 3/2013 | Nosse et al. | |
| 2013/0143892 A1 | 6/2013 | Heckel et al. | |

FOREIGN PATENT DOCUMENTS

| | | |
|---|---|---|
| EP | 1559428 A1 | 8/2005 |
| WO | 2006113140 A2 | 10/2006 |
| WO | 2007145834 A2 | 12/2007 |
| WO | 2008025798 A1 | 3/2008 |
| WO | 2008109702 A1 | 9/2008 |
| WO | 2010004347 A1 | 1/2010 |
| WO | 2010004348 A1 | 1/2010 |
| WO | 2010149684 A1 | 12/2010 |
| WO | 2010149685 A1 | 12/2010 |
| WO | 2011138427 A2 | 11/2011 |
| WO | 2012080476 A1 | 6/2012 |
| WO | 2012098217 A1 | 7/2012 |
| WO | 2012123449 A1 | 9/2012 |

OTHER PUBLICATIONS

Jones, R.M. et al., "GPR119 agonists for the treatment of type 2 diabetes". Expert Opinion on Therapeutic Patents 2009 Informa Healthcare for GBR LNKSD—DOI: 10.1517/13543770903153878, vol. 19, No. 10, Oct. 2009, p. 1339-1359.

International Search Report and Written Opinion for PCT/EP2012/054376 mailed Jun. 18, 2012.

Rew, Y. "Discovery and optimization of piperidyl benzamide derivatives as a novel class of 11.beta.-HSD1 inhibitiors". Bioorg. Med. Chem Letters, vol. 19, No. 6, Jan. 23, 2009, p. 1797-1801.

* cited by examiner

Primary Examiner — Zohreh Fay

(74) Attorney, Agent, or Firm — Michael P. Morris; Timothy X. Witkowski

(57) ABSTRACT

The present invention relates to compounds of general formula I,

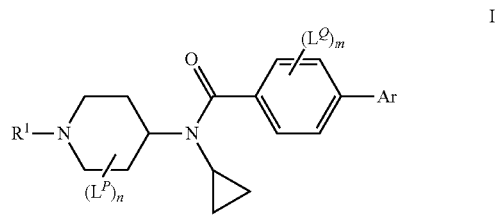

wherein the groups $R^1$, $L^P$, $L^Q$, Ar, m and n are as defined in the application, which have valuable pharmacological properties, and in particular bind to the GPR119 receptor and modulate its activity.

6 Claims, No Drawings

COMPOUNDS, PHARMACEUTICAL COMPOSITIONS AND USES THEREOF

FIELD OF THE INVENTION

The present invention relates to new compounds, in particular compounds of the formula I

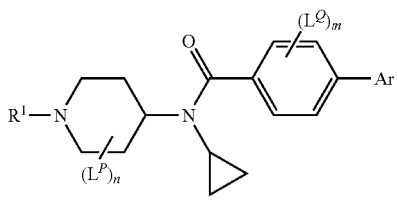

wherein the groups $R^1$, $L^P$, $L^Q$, Ar, m and n are defined as hereinafter, to processes for preparing such compounds, to pharmaceutical compositions, to their use as modulators of the G-protein-coupled receptor GPR119, to methods for their therapeutic use, in particular in diseases and conditions mediated by the modulation of the G-protein-coupled receptor GPR119, and to pharmaceutical compositions comprising them.

BACKGROUND OF THE INVENTION

Diabetes mellitus is a serious metabolic disease which affects more than 100 million people worldwide. In the USA there are more than 12 million diabetics with 600,000 new cases diagnosed every year. The prevalence of diabetes mellitus is increasing, which means in particular a high frequency of complications as well, leading to a substantial impairment of quality of life and life expectancy. Because of diabetes-associated microvascular complications, in the industrialised countries type 2 diabetes is currently the most common cause of adult-onset loss of vision, renal insufficiency and amputations. In addition, type 2 diabetes is associated with a two- to five-fold increase in the risk of cardiovascular disease.

The UKPDS study (United Kingdom Prospective Diabetes Study) showed that intensive treatment with common therapeutic agents, e.g. metformin, sulphonylureas or insulin, results in only a limited improvement in glycaemic control (difference in the HbA1c value ~0.9%). Moreover, glycaemic control deteriorated considerably over time even in patients in the intensive treatment group, and this was put down to a deterioration in beta cell function. Diabetes is also a major cause of damage to the retina at the back of the eye and increases the risk of cataract and glaucoma. Finally, diabetes is associated with nerve damage, particularly in the legs and feet, which affects the patient's ability to feel pain and contributes to serious infections. All in all, complications of diabetes are one of the major causes of death worldwide.

Adiposity (obesity) is the result of an imbalance between calorie intake and energy consumption. It correlates to a high degree with insulin resistance and diabetes. However, the molecular mechanisms that are involved in obesity/diabetes syndromes are not yet clear. At an early stage of the development of obesity, an increased insulin secretion balances out the insulin resistance and protects the patient from hyperglycaemia. However, after a time, the beta cell function worsens and non-insulin-dependent diabetes develops in about 20% of the obese population. Obesity has thus become a critical risk factor for diabetes, but the factors that predispose one group of patients to a pathological change in insulin secretion as a response to the accumulation of fat are currently unknown. Obesity also significantly increases the risk of the development of cardiovascular disease. Diabetes is also implicated in the formation of kidney complaints, eye complaints and problems of the nervous system. Kidney disease, also known as nephropathy, sets in when the filtering mechanism of the kidneys is disrupted and proteins escape into the urine in excessive amounts and finally the kidney fails. Therefore there is a medical need for medicaments for preventing and/or treating metabolic disorders (particularly diabetes, predominantly type 2 diabetes) and the complications thereof. In particular there is a need for medicaments with good activity in terms of glycaemic control, disease-modifying properties and reducing cardiovascular morbidity and mortality, and which also have a better safety profile.

Dyslipidemia is a disorder of lipoprotein metabolism, including lipoprotein overproduction or deficiency. Dyslipidemias may be manifested by elevation of the total cholesterol, LDL cholesterol and triglyceride and free fatty acid concentrations, and a decrease in high-density lipoprotein (HDL) cholesterol concentration in the blood. Dyslipidemia occurs often in situations including diabetes, a common cause of lipidemia. For adults with diabetes, it has been recommended that the levels of LDL, HDL, and total cholesterol, and triglyceride be measured every year. Optimal LDL cholesterol levels for adults with diabetes are less than 100 mg/dL (2.60 mmol/L), optimal HDL cholesterol levels are equal to or greater than 40 mg/dL (1.02 mmol/L), and desirable triglyceride levels are less than 150 mg/dL (1.7 mmol/L).

GPR119 is a G-protein coupled receptor (also known as GPCR2, RUP3, SNORF25 or GDIR) which is expressed predominantly in the beta cells of the pancreas and in the K- and L-cells of the intestine. The GPR119 receptor and isoforms have been identified in mammalian species including human, rat, mouse, hamster, chimpanzee, rhesus monkey, cattle and dog. The expression of GPR119 in the pancreas and particularly in the pancreatic β-cells led to the hypothesis that the GPR119 receptor could have effects upon insulin secretion. Activation of the receptor stimulates the cAMP signal pathway, increasing the intracellular levels of cAMP in these cells. This will lead to an improved diabetic situation by a dual action of such a compound: stimulation of cAMP in the beta cell occurs directly via activation of GPR119 in these cells and furthermore indirectly via stimulation of the release of neuroendocrine peptides like GIP and GLP-1 and PYY from the gut. The release of these peptides may have also additional beneficial effects, e.g. on food intake, gastric emptying and other yet unknown functions. Also, a GPR119 agonist can be expected to bring about an improvement in the beta cell function and the beta cell mass. In fact, activation of GPR119 stimulates insulin secretion in-vitro and in-vivo (in rodents) in a glucose-dependent manner. The discovery of two endogenous ligands, lysophospha-tidylcholine (LPC) and oleoylethanolamide (OEA) as well as more potent GPR119 agonists have led to the characterization of GPR119 as both an insulin and incretin (GLP-1 and GIP) secretagogue receptor capable of lowering plasma glucose and thereby facilitating glycemic control without the risk of hypoglycemia (Biochem. Biophys. Res. Comm. 2005, 744-751; Cell Metabolism 2006, 167-175; Endocrinolgy 2007, 2601-9). It has recently been shown that GPR119 agonists effectively lower the blood glucose levels in diabetic rodents without the risk of hypoglycaemia. GPR119 knockout animals have shown that both insulin and incretin secretion induced by GPR119 agonists are dependent upon GPR119 receptor. In addition, it has been shown that GPR119 agonists decrease food intake resulting in weight loss in Sprague Dawley rats. Therefore the GPR119 agonists may be expected to have a therapeutic benefit in metabolic diseases. Examples of such diseases include type 1 diabetes, type 2 diabetes, insufficient glucose tolerance, insulin resistance, hyper-glycaemia, hyperlipidaemia, hypercholesterolaemia, dyslipidaemia, syndrome X, metabolic syndrome, obesity, high blood pressure, chronic systemic inflammation, retinopathy, neuropathy, nephropathy, atherosclerosis, endothelial dysfunction and bone-related diseases (such as osteoporosis, rheumatoid arthritis or osteoarthritis). For comparison and additional information also see
1. Dhayal, S., Morgan, N. G. The significance of GPR119 agonists as a future treatment for type 2 diabetes. Drug News Perspect. 2010, 23(7), 418-24.
2. Yoshida, S., Tanaka, H., Oshima, H., Yamazaki, T., Yonetoku, Y., Ohishi, T., Matsui, T., Shibasaki, M. AS1907417, a novel GPR119 agonist, as an insulinotropic and β-cell preservative agent for the treatment of type 2 diabetes. Biochem Biophys Res Commun. 2010, 400(4), 745-51.
3. Jones, R. M., Leonard, J. N., Buzard, D. J., Lehman, J. GPR119 agonists for the treatment of type 2 diabetes. Expert Opinion on Therapeutic Patents 2009, Vol. 19, No. 10: 1339-1359.

AIM OF THE PRESENT INVENTION

The aim of the present invention is to provide new compounds, in particular new N-cyclopropyl-N-piperidinyl-benzamide derivatives, which are active with regard to the G-protein-coupled receptor GPR119.

Another aim of the present invention is to provide new compounds, in particular new N-cyclopropyl-N-piperidinyl-benzamide derivatives, which are agonists of the G-protein-coupled receptor GPR119.

A further aim of the present invention is to provide new compounds, in particular new N-cyclopropyl-N-piperidinyl-benzamide derivatives, which have an activating effect on the G-protein-coupled receptor GPR119 in vitro and/or in vivo and possess suitable pharmacological and pharmacokinetic properties to use them as medicaments.

A further aim of the present invention is to provide effective GPR119 agonists, in particular for the treatment of metabolic disorders, for example diabetes, dyslipidemia and/or obesity.

A further aim of the present invention is to provide methods for treating a disease or condition mediated by the activation the G-protein-coupled receptor GPR119 in a patient.

A further aim of the present invention is to provide a pharmaceutical composition comprising at least one compound according to the invention.

A further aim of the present invention is to provide a combination of at least one compound according to the invention with one or more additional therapeutic agents.

A further aim of the present invention is to provide methods for the synthesis of the new compounds, in particular N-cyclopropyl-N-piperidinyl-benzamide derivatives.

A further aim of the present invention is to provide starting and/or intermediate compounds suitable in methods for the synthesis of the new compounds.

Further aims of the present invention become apparent to the one skilled in the art by the description hereinbefore and in the following and by the examples.

OBJECT OF THE INVENTION

It has now been found that the compounds according to the invention described in more detail hereinafter have surprising and particularly advantageous properties, and in particular as GPR119 agonists.

In a first aspect the invention thus relates to a compound of formula I

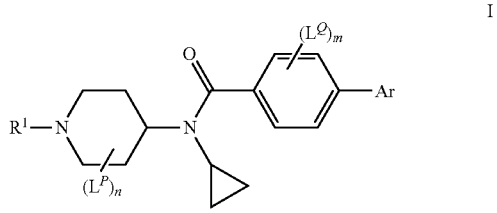

wherein
$R^1$ is selected from the group $R^1$-G1 consisting of a 5- or 6-membered heteroaromatic ring which contains 1, 2 or 3 heteroatoms independently of each other selected from N, O and S; and wherein optionally a second carbocyclic ring may be condensed to said heteroaromatic ring, wherein said second carbocyclic ring is unsaturated or aromatic and 5- or 6-membered and may optionally contain 1, 2 or 3 heteroatoms independently of each other selected from N, O and S, and wherein in said second carbocyclic ring 1 or 2 —$CH_2$-groups may be optionally replaced by —N($R^N$)—, —C(=O)—, —S(=O)— or —S(=O)$_2$—, and
  wherein in said heteroaromatic ring and/or said second carbocyclic ring the H-atom in one or more NH groups may be optionally replaced by $R^N$, and
  wherein each of said heteroaromatic ring and/or second carbocyclic ring independently of each other may be optionally substituted with one or more substituents selected from $L^{Ar}$; and
  wherein said heteroaromatic ring or said second carbocyclic ring may be optionally substituted with a group $R^2$; and
$R^N$ independently of each other is selected from the group $R^N$-G1 consisting of H, $C_{1-4}$-alkyl, $C_{1-4}$-alkyl-C(=O)—, and $C_{1-4}$-alkyl-S(=O)$_2$—; and
Ar is selected from the group Ar-G1 consisting of a phenyl ring, a tetrazolyl ring, and a 5- or 6-membered heteroaromatic ring which contains 1, 2 or 3 heteroatoms independently of each other selected from N, O and S; and wherein optionally a second carbocyclic ring may be condensed to said phenyl ring or heteroaromatic ring, wherein said second carbocyclic ring is unsaturated or aromatic and 5- or 6-membered and may contain 1, 2 or 3 heteroatoms independently of each other selected from N, O and S, and wherein in said second carbocyclic ring 1 or 2 —$CH_2$-groups may be optionally replaced by —N($R^N$)—, —C(=O)—, —S(=O)— or —S(=O)$_2$—, and
  wherein in said heteroaromatic ring and/or said second carbocyclic ring the H-atom in one or more NH groups may be optionally replaced by $R^N$, and
  wherein each of said phenyl ring, heteroaromatic ring and/or second carbocyclic ring independently of each other may be optionally substituted with one or more substituents selected from $L^{Ar}$; and
  wherein said phenyl ring, tetrazolyl ring, heteroaromatic ring or second carbocyclic ring may be optionally substituted with a group T; and
T is selected from the group T-G1 consisting of F, Cl, Br, I, CN, OH, $NO_2$, $C_{1-6}$-alkyl-, $C_{1-6}$-alkenyl-, $C_{1-6}$-alkynyl-, $C_{3-6}$-cycloalkyl, $C_{1-6}$-alkyl-O—, $C_{3-6}$-cycloalkyl-O—, $C_{1-6}$-alkyl-S—, HO—C(=O)—, $C_{1-6}$-alkyl-O—C(=O)—, $C_{1-4}$-alkyl-C(=O)—, $C_{3-6}$-cycloalkyl-C (=O)—, $C_{1-4}$-alkyl-S(=O)—, $C_{1-4}$-alkyl-S(=O)$_2$—, $R^{NT1}R^{NT2}N$—, $R^{NT1}R^{NT2}N$—C(=O)—, $R^{NT1}R^{NT2}N$—S(=O)$_2$—, $R^{NT1}R^{NT2}N$—C(=O)—($R^N$)N—, heterocyclyl, heterocyclyl-O—, aryl, aryl-O—, heteroaryl and heteroaryl-O—, wherein each alkyl, alkenyl, alkynyl, and cycloalkyl group may be optionally substituted with one or more substituents independently of each other selected from F, Cl, CN, OH, $C_{1-3}$-alkyl, $C_{3-6}$-cycloalkyl, $C_{1-3}$-alkyl-O—, $R^{NT1}R^{NT2}N$—, $R^{NT1}R^{NT2}N$—C(=O)—, $C_{1-4}$-alkyl-S(=O)—, $C_{1-4}$-alkyl-S(=O)$_2$—, $R^{NT1}R^{NT2}N$—S(=O)$_2$—, aryl, heteroaryl, and heterocyclyl, and wherein aryl denotes phenyl or naphthyl, and wherein heteroaryl is a 5- or 6-membered aromatic carbocyclic ring which contains 1, 2, 3 or 4 heteroatoms independently of each other selected from N, O and S, wherein the H-atom in one or more NH groups may be optionally replaced by $R^N$; and wherein heterocyclyl is a 4- to 7-membered unsaturated or saturated carbocyclic ring in which 1 or 2 —CH$_2$-groups independently of each other are replaced by NR$^N$, O, —C(=O)—, S, —S(=O)— or —S(=O)$_2$—, and/or in which a —CH-group is replaced by N; and wherein each aryl, heteroaryl or heterocyclyl group may be optionally substituted with one or more substituents independently of each other selected from $L^{Ar}$; and $R^{NT1}$ is selected from the group $R^{NT1}$-G1 consisting of H, $C_{1-6}$-alkyl, $C_{3-6}$-cycloalkyl, $C_{1-6}$-alkyl-C(=O)—, $C_{1-6}$-alkyl-S(=O)$_2$, heterocyclyl, aryl and heteroaryl, wherein each alkyl and cylcoalkyl group may be optionally substituted with one or more substituents independently of each other selected from the group consisting of F, OH, CN, $C_{1-4}$-alkyl, $C_{1-4}$-alkyl-O—, $R^N_2$N, $C_{1-4}$-alkyl-S(=O)$_2$—, $C_{3-6}$-cycloalkyl, heterocyclyl, phenyl and heteroaryl; and wherein heterocyclyl is a $C_{4-7}$-cycloalkyl ring in which 1 or 2 —CH$_2$-groups independently of each other are replaced by NR$^N$, O, C(=O), S, S(=O) or S(=O)$_2$; and wherein heterocyclyl may be optionally substituted with one or more substituents independently of each other selected from F, $C_{1-4}$-alkyl, $R^N_2$N, OH and $C_{1-4}$-alkyl-O—; and wherein aryl is phenyl or naphthyl; and wherein heteroaryl is a 5- or 6-membered aromatic carbocyclic ring which contains 1, 2 or 3 heteroatoms independently of each other selected from N, O and S, wherein the H-atom in one or more NH groups may be optionally replaced by $R^N$; and wherein aryl, phenyl and heteroaryl may be optionally substituted with one or more substituents $L^{Ar}$; and $R^{NT2}$ is selected from the group $R^{NT2}$-G1 consisting of H and $C_{1-6}$-alkyl; or $R^{NT1}$ and $R^{NT2}$ are linked to form one group selected from the group $R^{NT1}R^{NT2}$-G1 consisting of a $C_{3-5}$-alkylene group, wherein 1 or 2 —CH$_2$-groups independently of each other are replaced by NR$^N$, O, C(=O), S, S(=O) or S(=O)$_2$; and which may be optionally substituted with one or more substituents independently of each other selected from F, $C_{1-4}$-alkyl, $(R^N)_2$N, OH and $C_{1-4}$-alkyl-O—;

$L^{Ar}$ is selected from the group $L^{Ar}$-G1 consisting of F, Cl, Br, I, CN, OH, NO$_2$, $C_{1-4}$-alkyl-, $C_{1-4}$-alkyl-O—, $(R^N)_2$N—C(=O), $(R^N)_2$N—, and $C_{1-4}$-alkyl-S(=O)$_2$—, wherein each alkyl group may be optionally substituted with one or more substituents independently of each other selected from F, Cl, CN, OH and $C_{1-3}$-alkyl-O—; and $L^P$ is selected from the group $L^P$-G1 consisting of F and $C_{1-3}$-alkyl, wherein the alkyl group may be substituted with one or more F-atoms; and $L^Q$ is selected from the group $L^Q$-G1 consisting of F, Cl, CN, OH, $C_{1-4}$-alkyl, $C_{3-7}$-cycloalkyl-, $F_2$HC, $F_3$C, $C_{1-4}$-alkyl-O—, $F_2$HC—O—, $F_3$C—O— and $C_{3-7}$-cycloalkyl-O—; and $R^2$ is selected from the group $R^2$-G1 consisting of F, Cl, Br, I, CN, OH, NO$_2$, $C_{1-6}$-alkyl-, $C_{1-6}$-alkenyl-, $C_{1-6}$-alkynyl-, $C_{3-6}$-cycloalkyl, $C_{1-6}$-alkyl-O—, $C_{3-6}$-cycloalkyl-O—, $C_{1-6}$-alkyl-S—, HO—C(=O)—, $C_{1-6}$-alkyl-O—C(=O)—, $C_{1-4}$-alkyl-C(=O)—, $C_{3-6}$-cycloalkyl-C(=O)—, $C_{1-4}$-alkyl-S(=O)—, $C_{1-4}$-alkyl-S(=O)$_2$—, $R^{NT1}R^{NT2}N$—, $R^{NT1}R^{NT2}N$—C(=O)—, $R^{NT1}R^{NT2}N$—S(=O)$_2$—, $R^{NT1}R^{NT2}N$—C(=O)—($R^N$)N—, heterocyclyl, heterocyclyl-O—, aryl, aryl-O—, heteroaryl and heteroaryl-O—, wherein each alkyl, alkenyl, alkynyl, and cycloalkyl group may be optionally substituted with one or more substituents independently of each other selected from F, Cl, CN, OH, $C_{1-3}$-alkyl, $C_{3-6}$-cycloalkyl, $C_{1-3}$-alkyl-O—, $R^{NT1}R^{NT2}N$—, $R^{NT1}R^{NT2}N$—C(=O)—, $C_{1-4}$-alkyl-S(=O)—, $C_{1-4}$-alkyl-S(=O)$_2$—, $R^{NT1}R^{NT2}N$—S(=O)$_2$—, aryl, heteroaryl, and heterocyclyl, and wherein aryl denotes phenyl or naphthyl, and wherein heteroaryl is a 5- or 6-membered aromatic carbocyclic ring which contains 1, 2, 3 or 4 heteroatoms independently of each other selected from N, O and S, wherein the H-atom in one or more NH groups may be optionally replaced by $R^N$; and wherein heterocyclyl is a 4- to 7-membered unsaturated or saturated carbocyclic ring in which 1 or 2 —CH$_2$-groups independently of each other are replaced by NR$^N$, O, —C(=O)—, S, —S(=O)— or —S(=O)$_2$—, and/or in which a —CH-group is replaced by N; and wherein each aryl, heteroaryl or heterocyclyl group may be optionally substituted with one or more substituents independently of each other selected from $L^{Ar}$; and m is an integer selected from 0, 1, or 2; and n is an integer selected from 0, 1, 2, 3, or 4;

including any tautomers and stereoisomers thereof, or a salt thereof or a solvate or hydrate thereof.

In a further aspect the present invention relates to processes for preparing a compound of general formula I and to new intermediate compounds in these processes.

A further aspect of the invention relates to a salt of the compounds of general formula I according to this invention, in particular to a pharmaceutically acceptable salt thereof.

In a further aspect this invention relates to a pharmaceutical composition, comprising one or more compounds of general formula I or one or more pharmaceutically acceptable salts thereof according to the invention, optionally together with one or more inert carriers and/or diluents.

In a further aspect this invention relates to a method for treating diseases or conditions which are mediated by activating the G-protein-coupled receptor GPR119 in a patient in need thereof characterized in that a compound of general formula I or a pharmaceutically acceptable salt thereof is administered to the patient.

According to another aspect of the invention, there is provided a method for treating a metabolic disease or disorder in a patient in need thereof characterized in that a compound of general formula I or a pharmaceutically acceptable salt thereof is administered to the patient.

According to another aspect of the invention, there is provided the use of a compound of the general formula I or a pharmaceutically acceptable salt thereof for the manufacture of a medicament for a therapeutic method as described hereinbefore and hereinafter.

According to another aspect of the invention, there is provided a compound of the general formula I or a pharmaceutically acceptable salt thereof for use in a therapeutic method as described hereinbefore and hereinafter.

In a further aspect this invention relates to a method for treating a disease or condition mediated by the activation of the G-protein-coupled receptor GPR119 in a patient that includes the step of administering to the patient in need of such treatment a therapeutically effective amount of a compound of the general formula I or a pharmaceutically acceptable salt thereof in combination with a therapeutically effective amount of one or more additional therapeutic agents.

In a further aspect this invention relates to a use of a compound of the general formula I or a pharmaceutically acceptable salt thereof in combination with one or more additional therapeutic agents for the treatment of diseases or conditions which are mediated by the activation of the G-protein-coupled receptor GPR119.

In a further aspect this invention relates to a pharmaceutical composition which comprises a compound according to general formula I or a pharmaceutically acceptable salt thereof and one or more additional therapeutic agents, optionally together with one or more inert carriers and/or diluents.

Other aspects of the invention become apparent to the one skilled in the art from the specification and the experimental part as described hereinbefore and hereinafter.

DETAILED DESCRIPTION

Unless otherwise stated, the groups, residues, and substituents, particularly Ar, $R^1$, $R^2$, T, $R^N$, $R^{NT1}$, $R^{NT2}$, $L^{Ar}$, $L^P$, $L^Q$, m, and n are defined as above and hereinafter. If residues, substituents, or groups occur several times in a compound, as for example $R^N$, $L^{Ar}$, $L^P$ or $L^Q$, they may have the same or different meanings. Some preferred meanings of individual groups and substituents of the compounds according to the invention will be given hereinafter. Any and each of these definitions may be combined with each other.

$R^1$:

$R^1$-G1:

The group $R^1$ is preferably selected from the group $R^1$-G1 as defined hereinbefore and hereinafter.

$R^1$-G2:

According to one embodiment the group $R^1$ is selected from the group $R^1$-G2 consisting of a 5-membered heteroaromatic ring which contains 2 or 3 heteroatoms independently of each other selected from N, O and S and a 6-membered heteroaromatic ring which contains 1 or 2 N atoms; and wherein optionally a second carbocyclic ring may be condensed to said 5- and 6-membered heteroaromatic rings, wherein said second carbocyclic ring is unsaturated or aromatic and 5- or 6-membered and may contain 1 or 2 heteroatoms independently of each other selected from N, O and S, and wherein in said second carbocyclic ring 1 or 2 —CH$_2$- groups may be optionally replaced by —N($R^N$)—, —C(=O)— or —S(=O)$_2$—, and wherein in said heteroaromatic ring and/or said second carbocyclic ring the H-atom in one or more NH groups may be optionally replaced by $R^N$, and wherein each of said heteroaromatic ring and/or second carbocyclic ring independently of each other may be optionally substituted with one or two substituents selected from $L^{Ar}$; and wherein said heteroaromatic ring or said second carbocyclic ring may be optionally substituted with a group $R^2$.

$R^1$-G3:

According to one embodiment the group $R^1$ is selected from the group $R^1$-G3 consisting of

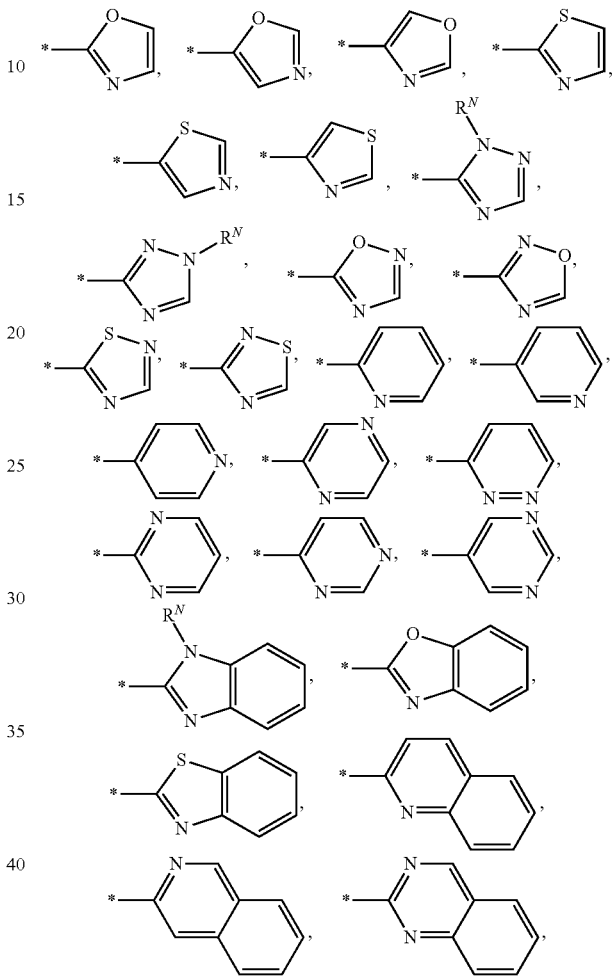

wherein each ring may be optionally substituted with one substituent $L^{Ar}$ and each group may be optionally substituted with one substituent $R^2$.

$R^1$-G3a:

According to one embodiment the group $R^1$ is selected from the group $R^1$-G3a consisting of

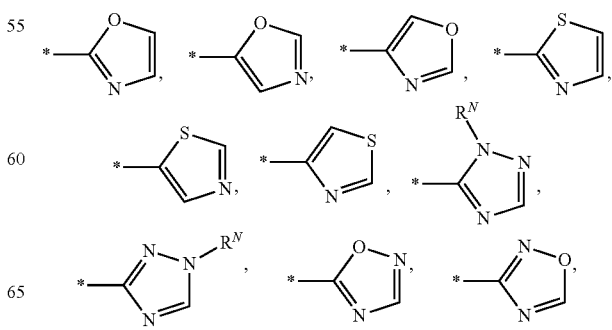

-continued

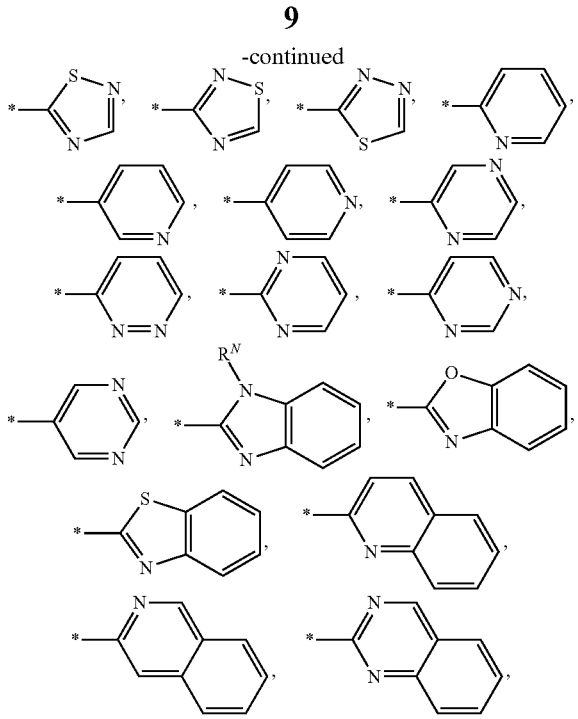

wherein each ring may be optionally substituted with one substituent $L^{Ar}$ and each group may be optionally substituted with one substituent $R^2$.

$R^1$-G4:

In another embodiment the group $R^1$ is selected from the group $R^1$-G4 consisting of

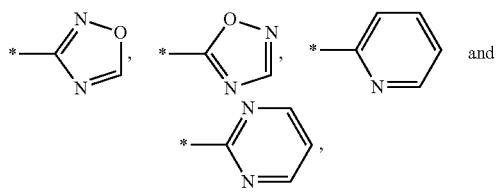

wherein each ring may be optionally substituted with one substituent $R^2$.

$R^1$-G4a:

In another embodiment the group $R^1$ is selected from the group $R^1$-G4a consisting of

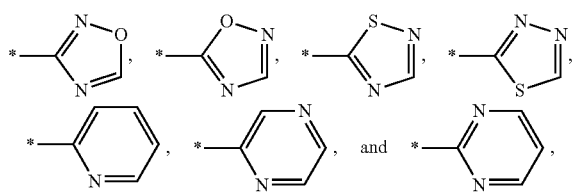

wherein each ring may be optionally substituted with one substituent $R^2$.

$R^1$-G5:

In another embodiment the group $R^1$ is selected from the group $R^1$-G5 consisting of

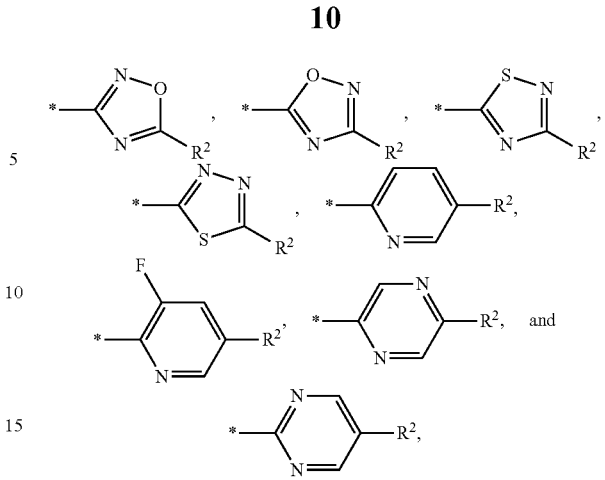

wherein $R^2$ is selected from the group consisting of:
H, F, Cl, Br, CN, $C_{1-4}$-alkyl, $C_{2-4}$-alkenyl, $C_{3-5}$-cycloalkyl, —O—$C_{1-4}$-alkyl, —C(=O)—O—$C_{1-4}$-alkyl, —NH$_2$, —NH($C_{1-4}$-alkyl), —N($C_{1-4}$-alkyl)$_2$, tetrahydropyranyl, benzyl, phenyl, pyridinyl, thiophenyl and thiazolyl,
  wherein each alkyl group may be substituted with one to three F atoms or one OH, —OCH$_3$ or tetrahydropyranyl group, and
  wherein each phenyl group may be substituted with F, Br, I or —OCH$_3$.

$R^1$-G5a:

In another embodiment the group $R^1$ is selected from the group $R^1$-G5a consisting of

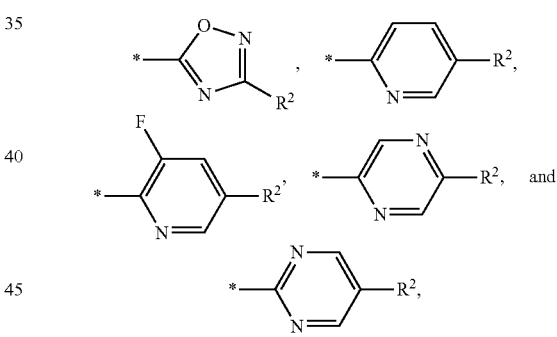

wherein $R^2$ is selected from the group consisting of: Cl, $C_{1-4}$-alkyl, cyclopropyl, and CF$_3$.

$R^N$ $R^N$-G1:

The group $R^N$ is preferably selected from the group $R^N$-G1 as defined hereinbefore and hereinafter.

RN-G2:

In another embodiment the group $R^N$ is selected from the group $R^N$-G2 consisting of H, methyl, ethyl, isopropyl, methylcarbonyl, and methylsulfonyl.

$R^N$-G3:

In another embodiment the group $R^N$ is selected from the group $R^N$-G3 consisting of H, methyl, methylcarbonyl, and methylsulfonyl.

$R^N$-G4:

In another embodiment the group $R^N$ is selected from the group $R^N$-G4 consisting of H, and methyl.

Ar:
Ar-G1:
  The group Ar is preferably selected from the group Ar-G1 as defined hereinbefore and hereinafter.
Ar-G2:
  In one embodiment the group Ar is selected from the group Ar-G2 consisting of a phenyl ring, a tetrazolyl ring, a 6-membered heteroaromatic ring which contains 1 or 2 N-atoms, and a 5-membered heteroaromatic ring which contains 1, 2 or 3 heteroatoms independently of each other selected from N, O and S; and wherein optionally a second carbocyclic ring may be condensed to said phenyl ring or said heteroaromatic ring, wherein said second carbocyclic ring is unsaturated or aromatic and is 5- or 6-membered and may optionally contain 1 or 2 heteroatoms independently of each other selected from N, O and S, and wherein in said second carbocyclic ring 1 or 2 —CH$_2$-groups may optionally be replaced by —N(R$^N$)—, —C(=O)—, —S(=O)— or —S(=O)$_2$—, and
    wherein in said heteroaromatic rings and/or said second carbocyclic ring the H-atom in one or more NH groups may be optionally replaced by R$^N$, and
    wherein each of said phenyl ring, heteroaromatic rings and second carbocyclic rings may be optionally substituted independently of each other with one or more substituents selected from L$^{Ar}$; and
    wherein said phenyl ring, tetrazolyl ring, heteroaromatic rings or second carbocyclic ring may be optionally substituted with a group T.
Ar-G2a:
  In another embodiment the group Ar is selected from the group Ar-G2a consisting of a phenyl ring, a tetrazolyl ring, a 6-membered heteroaromatic ring which contains 1 or 2 N-atoms and a 5-membered heteroaromatic ring which contains 1, 2 or 3 heteroatoms independently of each other selected from N, O and S; wherein said phenyl ring, tetrazolyl ring or heteroaromatic ring may be optionally substituted with a group T, and wherein said phenyl ring and heteroaromatic carbocyclic ring may be optionally substituted with one or more substituents independently of each other selected from L$^{Ar}$, and
  wherein in said heteroaromatic carbocyclic rings the H-atom in one or more NH groups may be optionally replaced by R$^N$.
Ar-G2b:
  In another embodiment the group Ar is selected from the group Ar-G2b consisting of a phenyl ring, a 5-membered heteroaromatic ring which contains 2 or 3 heteroatoms independently of each other selected from N, O or S, and a 6-membered heteroaromatic ring which contains 1 or 2 N atoms; and wherein a second carbocyclic ring is condensed to said phenyl ring or said heteroaromatic ring, wherein said second carbocyclic ring is unsaturated or aromatic and is 5- or 6-membered and may optionally contain 1 or 2 heteroatoms independently of each other selected from N, O and S, and wherein in said second carbocyclic ring 1 or 2 —CH$_2$-groups may be optionally replaced by —N(R$^N$)—, —C(=O)—, —S(=O)— or —S(=O)$_2$—, and
    wherein in said heteroaromatic ring and/or said second ring the H-atom in one or more NH groups may be optionally replaced by R$^N$, and
    wherein each of said phenyl ring, heteroaromatic ring and second carbocyclic ring may be optionally substituted with one or more substituents independently of each other selected from L$^{Ar}$; and
    wherein said phenyl ring, heteroaromatic ring or second carbocyclic ring may be optionally substituted with a group T.

Ar-G3:
  In one embodiment the group Ar is selected from the group Ar-G3 consisting of the cyclic groups phenyl, pyridinyl, pyrazinyl, pyridazinyl, pyrimidinyl, isoxazolyl, oxazolyl, oxadiazolyl, imidazolyl, pyrazolyl, triazolyl, tetrazolyl, thienyl and thiazolyl, and wherein optionally a second carbocyclic ring may be condensed to said cyclic groups, wherein said second carbocyclic ring is selected from the group consisting of cyclopentene, cyclohexene, dihydropyrrole, tetrahydropyridine, tetrahydropyrazine, dihydrooxazine, dihydrofuran, dihydropyran, [1,3]dioxol, dihydrodioxine, dihydropyrimidine, dihydropyrazine, dihydropyridazine, benzene, pyridine, pyrimidine, pyrazine, pyridazine, oxazole, triazole and thiazole, wherein in said second carbocyclic ring 1 or 2 —CH$_2$-groups may be optionally replaced by —C(=O)—, and wherein in said cyclic groups and/or second carbocyclic ring the H-atom in one or more —NH-groups may be replaced independently of each other by the substituent R$^N$,
    wherein each of the beforementioned rings may be optionally substituted with one or more substituents independently of each other selected from L$^{Ar}$, and
    wherein said cyclic group or second carbocyclic ring may be optionally substituted with a group T.
Ar-G3a:
  In one embodiment the group Ar is selected from the group Ar-G3a consisting of a phenyl, tetrazolyl, and a heteroaromatic ring selected from pyridinyl, pyrazinyl, pyridazinyl, pyrimidinyl, isoxazolyl, oxazolyl, oxadiazolyl, imidazolyl, pyrazolyl, triazolyl, thienyl and thiazolyl, wherein said phenyl and heteroaromatic rings may be optionally substituted with one or more substituents independently of each other selected from L$^{Ar}$, and wherein said phenyl, tetrazolyl, or heteroaromatic ring may be optionally substituted with a group T.
Ar-G3b:
  In one embodiment the group Ar is selected from the group Ar-G3b consisting of a phenyl and a heteroaromatic ring selected from pyridinyl, pyrazinyl, pyridazinyl, pyrimidinyl, isoxazolyl, oxazolyl, oxadiazolyl, imidazolyl, pyrazolyl, pyrrolyl, thienyl, thiazolyl and triazolyl ring, and wherein a second carbocyclic ring is condensed to said phenyl or heteroaromatic ring, wherein said second carbocyclic ring is selected from the group consisting of cyclopentene, cyclohexene, dihydropyrrole, pyrrole, tetrahydropyridine, tetrahydropyrazine, dihydrooxazine, dihydrofuran, dihydropyran, [1,3]dioxol, dihydrodioxine, dihydropyrimidine, dihydropyrazine, dihydropyridazine, benzene, pyridine, pyrimidine, pyrazine, pyridazine, oxazole, triazole and thiazole, wherein in said second carbocyclic ring 1 or 2 —CH$_2$-groups may be optionally replaced by —C(=O)—, and wherein in said heteroaromatic ring and/or second carbocyclic ring the H-atom in one or more —NH-groups may be replaced independently of each other by the substituent R$^N$,
    wherein each of the beforementioned rings may be optionally substituted with one or more substituents independently of each other selected from L$^{Ar}$, and
    wherein said phenyl ring, heteroaromatic ring or second carbocyclic ring may be optionally substituted with a group T.
Ar-G4:
  In one embodiment the group Ar is selected from the group Ar-G4 consisting of the cyclic groups phenyl, pyridyl, pyrazinyl, pyridazinyl, pyrimidinyl, isoxazolyl, oxazolyl, imidazolyl, pyrazolyl, thienyl, thiazolyl, [1,2,3]triazolyl, [1,2,4]triazolyl, tetrazolyl, [1,2,4]triazolo[1,5-a]pyridinyl, benzooxazolyl, benzothiazolyl, indan-1-onyl, indolyl, 2,3-dihydro-indolyl, quinoxalinyl, quinolinyl, 3H-quinazolin-4-onyl, 2,3-dihydro-benzo[1,4]dioxinyl, isoindole-1,3-dionyl, 1,3-dihydro-indol-2-onyl, 1H-indazolyl, and indanyl, wherein in the beforementioned groups in one or more —NH-groups the H-atom may be optionally replaced independently of each other by the substituent $R^N$, and wherein each ring may be optionally substituted with one or more substituents independently of each other selected from $L^{Ar}$, and wherein the beforementioned cyclic groups may be optionally substituted with a group T.

Ar-G5:

In another embodiment the group Ar is selected from the group Ar-G5 consisting of:

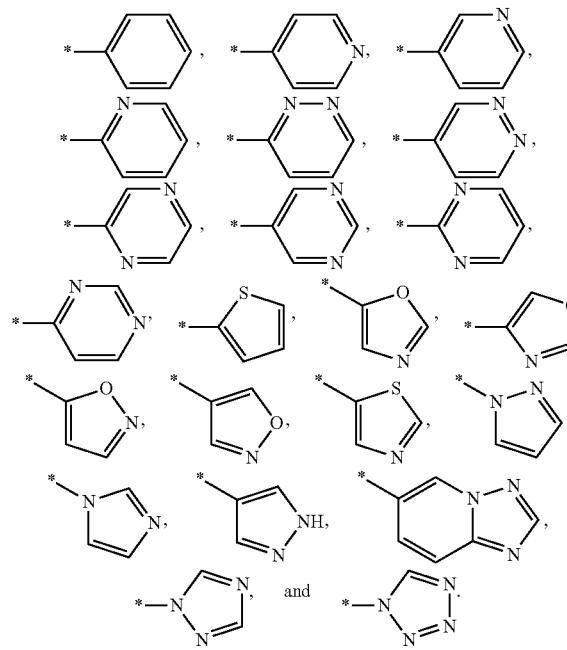

wherein in the above groups a H-atom in a —NH-group may be optionally replaced by the substituent $R^N$, and wherein each group is not substituted with a group T or is substituted with a group T, and each ring may be optionally substituted with one or more substituents independently of each other selected from $L^{Ar}$, and wherein the groups T and $L^{Ar}$ are defined as hereinbefore and hereinafter.

Ar-G5a:

In another embodiment the group Ar is selected from the group Ar-G5a consisting of:

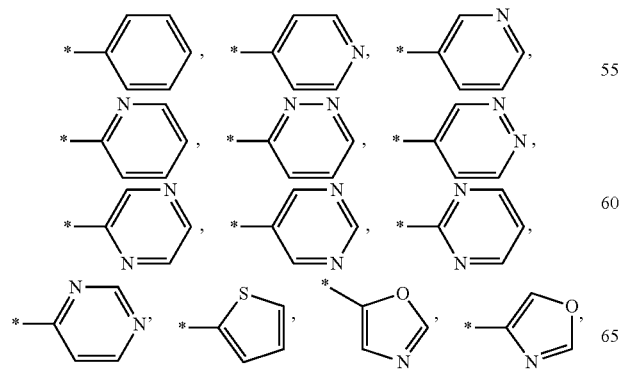

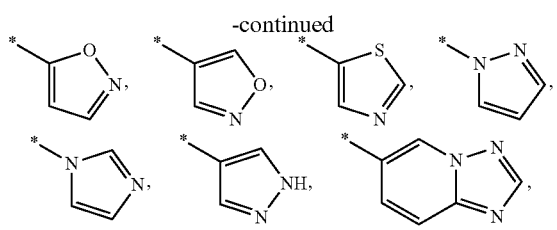

wherein in the above groups a H-atom in a —NH-group may be optionally replaced by the substituent $R^N$, and wherein each group is not substituted with a group T or is substituted with a group T, and each ring may be optionally substituted with one or more substituents independently of each other selected from $L^{Ar}$, and wherein the groups T and $L^{Ar}$ are defined as hereinbefore and hereinafter.

Ar-G6:

In another embodiment the group Ar is selected from the group Ar-G6 consisting of:

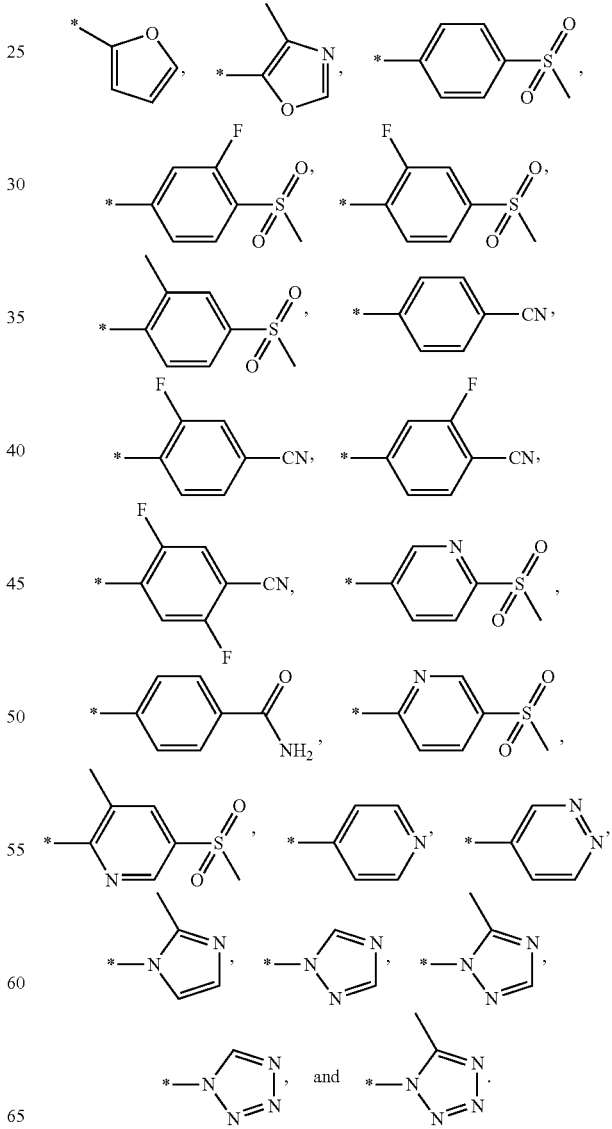

Ar-G6a:

In another embodiment the group Ar is selected from the group Ar-G6a consisting of:

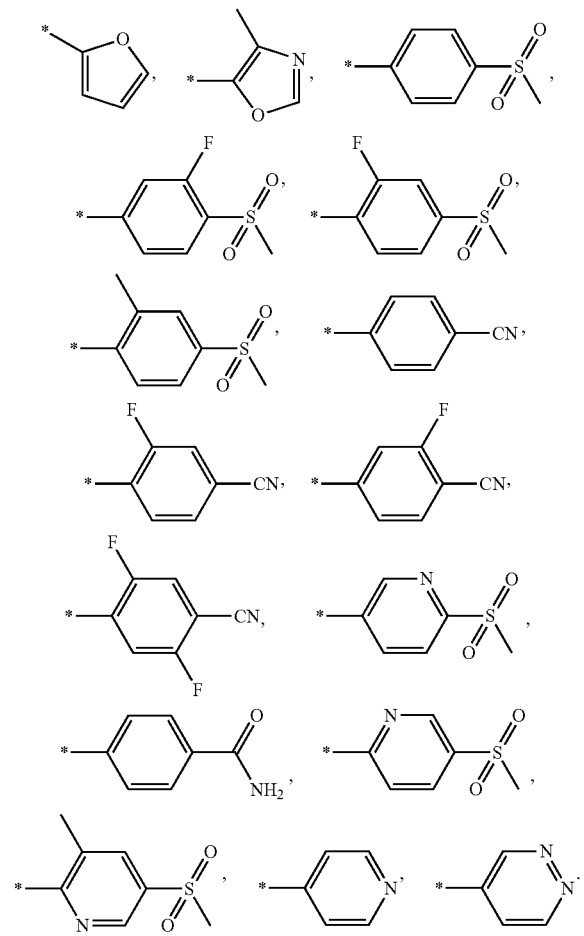

Ar-G6b:

In another embodiment the group Ar is selected from the group Ar-G6b consisting of:

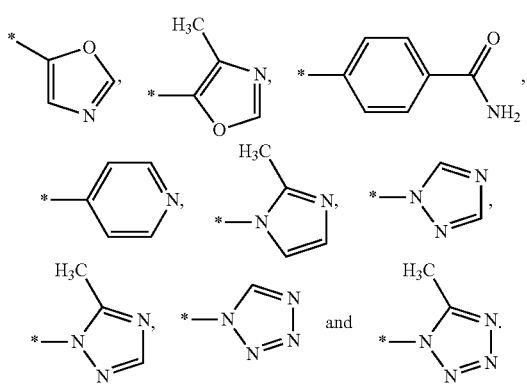

Ar-G7a:

In another embodiment the group Ar is selected from the group Ar-G7a consisting of:

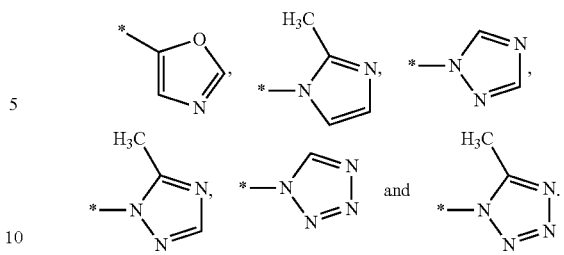

Ar-G7b:

In another embodiment the group Ar is selected from the group Ar-G7b consisting of:

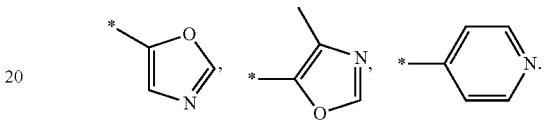

T

T-G1:

The group T is preferably selected from the group T-G1 as defined hereinbefore and hereinafter.

T-G2:

According to one embodiment the group T is selected from the group T-G2 consisting of F, Cl, Br, CN, OH, $C_{1-4}$-alkyl-, $C_{1-4}$-alkyl-O—, $C_{1-4}$-alkyl-O—C(=O)—, $C_{1-4}$-alkyl-C(=O)—, $C_{1-4}$-alkyl-S(=O)—, $C_{1-4}$-alkyl-S(=O)$_2$—, $R^{NT1}R^{NT2}$N—C(=O)—, $R^{NT1}R^{NT2}$N—S(=O)$_2$—, $R^{NT1}R^{NT2}$N—, wherein each alkyl-group may be optionally substituted with one or more substituents independently of each other selected from F, Cl, CN, OH, phenyl, heteroaryl, and heterocyclyl, and in addition the group T-G2 consists of $R^{NT1}R^{NT2}$N—C(=O)—$C_{1-4}$-alkyl- and $C_{1-4}$-alkyl-S(=O)$_2$—$C_{1-4}$-alkyl-, wherein heteroaryl is selected from the group consisting of pyridinyl, pyrimidinyl, pyridazinyl, pyrazinyl, pyrazolyl, imidazolyl, [1,2,4]triazolyl and tetrazolyl; and wherein heterocyclyl is selected from the group consisting of azetidinyl, pyrrolidinyl, piperidinyl, piperazinyl and morpholinyl, wherein in each of the beforementioned groups a —CH$_2$-group may be optionally replaced by a group selected from —C(=O)— and —S(=O)$_2$—, and wherein each of the beforementioned groups may be optionally substituted with one or more substituents independently of each other selected from $C_{1-3}$-alkyl; and wherein phenyl and heteroaryl may be optionally substituted independently of each other with one or more substituents $L^{Ar}$.

T-G3:

According to another embodiment the group T is selected from the group T-G3 consisting of CN, $C_{1-3}$-alkyl-, NC—$C_{1-3}$-alkyl-, $C_{1-4}$-alkyl-S(=O)—, $C_{1-4}$-alkyl-S(=O)$_2$—, $R^{NT1}R^{NT2}$N—S(=O)$_2$—, $R^{NT1}R^{NT2}$N—C(=O)—, and $R^{NT1}R^{NT2}$N—.

T-G4:

According to another embodiment the group T is selected from the group T-G4 consisting of CN, H$_3$C—, $C_{1-3}$-alkyl-S(=O)—, $C_{1-3}$-alkyl-S(=O)$_2$— and $R^{NT1}R^{NT2}$N—C(=O)—.

$R^{NT1}$ $R^{NT1}$-G1:

$R^{NT1}$ is preferably selected from the group $R^{NT1}$-G1 as defined hereinbefore and hereinafter.

$R^{NT1}$-G2:

In another embodiment $R^{NT1}$ is selected from the group $R^{NT1}$-G2 consisting of H, $C_{1-3}$-alkyl, $C_{3-6}$-cycloalkyl, $C_{1-4}$-alkyl-C(=O)—, $C_{1-4}$-alkyl-S(=O)$_2$—
wherein each alkyl and cylcoalkyl group may be optionally substituted with one or more substituents independently of each other selected from the group consisting of F, OH, $C_{1-3}$-alkyl-O— and $(R^N)_2$N.

$R^{NT1}$-G3:

In another embodiment $R^{NT1}$ is selected from the group $R^{NT1}$-G3 consisting of H, $C_{1-3}$-alkyl, $C_{1-3}$-alkyl-C(=O)—, $C_{1-3}$-alkyl-S(=O)$_2$—.

$R^{NT2}$ $R^{NT2}$-G1:

$R^{NT2}$ is preferably selected from the group $R^{NT2}$-G1 as defined hereinbefore and hereinafter.

$R^{NT2}$-G2:

In another embodiment $R^{NT2}$ is selected from the group $R^{NT2}$-G2 consisting of H and $C_{1-3}$-alkyl.

$R^{NT1}R^{NT2}$ $R^{NT1}R^{NT2}$-G1:

According to one embodiment the groups $R^{NT1}$ and $R^{NT2}$ are linked and form a group which is selected from the group $R^{NT1}R^{NT2}$-G1 as defined hereinbefore and hereinafter.

$R^{NT1}R^{NT2}$-G2:

According to another embodiment the groups $R^{NT1}$ and $R^{NT2}$ are linked and together with the N-atom to which they are attached form a group which is selected from the group $R^{NT1}R^{NT2}$-G2 consisting of azetidinyl, pyrrolidinyl, piperidinyl, morpholinyl, piperazinyl, piperazin-2-onyl, N—$C_{1-3}$-alkyl-piperazinyl, N—$C_{1-3}$-alkyl-piperazin-2-onyl, and N—($C_{1-3}$-alkyl-O(=O))-piperazinyl, which may be optionally substituted with one or more substituents independently of each other selected from the group consisting of F, HO, $C_{1-3}$-alkyl, $C_{1-3}$-alkyl-O—, and $(R^N)_2$N.

$L^{Ar}$:

$L^{Ar}$-G1:

The group $L^{Ar}$ is preferably selected from the group $L^{Ar}$-G1 as defined hereinbefore and hereinafter.

$L^{Ar}$-G2:

In another embodiment the group $L^{Ar}$ is selected from the group $L^{Ar}$-G2 consisting of F, Cl, Br, I, CN, OH, $C_{1-3}$-alkyl-, $C_{1-3}$-alkyl-O—, $H_2N$—, $C_{1-3}$-alkyl-NH— and ($C_{1-3}$-alkyl)$_2$N—, wherein the $C_{1-3}$-alkyl- and $C_{1-3}$-alkyl-O— group may be optionally substituted with one or more F-atoms.

$L^{Ar}$-G3:

In another embodiment the group $L^{Ar}$ is selected from the group $L^{Ar}$-G3 consisting of F, CN, OH, $H_3C$—, $F_3C$—, $HF_2C$—, $H_3C$—O—, $HF_2C$—O—, $F_3C$—O—.

$R^2$:

$R^2$-G1:

The group $R^2$ is preferably selected from the group $R^2$-G1 as defined hereinbefore and hereinafter.

$R^2$-G2:

According to one embodiment the group $R^2$ is selected from the group $R^2$-G2 consisting of F, Cl, Br, I, CN, OH, $C_{1-6}$-alkyl-, $C_{1-6}$-alkenyl-, $C_{1-6}$-alkynyl-, $C_{3-6}$-cycloalkyl, $C_{1-6}$-alkyl-O—, $C_{3-6}$-cycloalkyl-O—, $C_{1-6}$-alkyl-S—, $C_{1-6}$-alkyl-O—C(=O)—, $C_{1-4}$-alkyl-S(=O)—, $C_{1-4}$-alkyl-S(=O)$_2$—$C_{1-4}$-alkyl-, $C_{1-4}$-alkyl-S(=O)$_2$—, $C_{1-4}$-alkyl-S(=O)$_2$—$C_{1-4}$-alkyl-, $R^{NT1}R^{NT2}$N—, $R^{NT1}R^{NT2}$N—$C_{1-3}$-alkyl-, $R^{NT1}R^{NT2}$N—C(=O)—, $R^{NT1}R^{NT2}$N—S(=O)$_2$—, $R^{NT1}R^{NT2}$N—S(=O)$_2$—$C_{1-4}$-alkyl-, $R^{NT1}R^{NT2}$N—C(=O)—$C_{1-4}$-alkyl-, heterocyclyl, heterocyclyl-O—, phenyl and heteroaryl, wherein each alkyl, alkenyl, alkynyl, and cycloalkyl group may be optionally substituted with one or more substituents independently of each other selected from F, Cl, CN, OH, $C_{1-3}$-alkyl, $C_{3-6}$-cycloalkyl, $C_{1-3}$-alkyl-O—, phenyl, heteroaryl, and heterocyclyl, and
wherein heteroaryl is selected from the group consisting of pyridinyl, pyrimidinyl, pyridazinyl, pyrazinyl, pyrazolyl, imidazolyl, thiazolyl, and thienyl; and
wherein heterocyclyl is selected from the group consisting of pyrrolidin-2-onyl, piperidin-2-onyl, piperazin-2-onyl, morpholinyl, morpholin-3-onyl, oxetanyl, tetrahydrofuranyl, and tetrahydropyranyl, each of which may be optionally substituted with one or two substituents independently of each other selected from $C_{1-3}$-alkyl; and
wherein phenyl and heteroaryl may be optionally substituted independently of each other with one or more substituents $L^{Ar}$.

$R^2$-G3:

According to one embodiment the group $R^2$ is selected from the group $R^2$-G3 consisting of F, Cl, CN, $C_{1-6}$-alkyl-, $C_{3-6}$-cycloalkyl, $C_{1-6}$-alkyl-O—, $C_{3-6}$-cycloalkyl-O—, $C_{1-4}$-alkyl-S(=O)—, $C_{1-4}$-alkyl-S(=O)$_2$—, $R^{NT1}R^{NT2}$N—, $R^{NT1}R^{NT2}$N—$C_{1-3}$-alkyl-, $R^{NT1}R^{NT2}$N—C(=O)—, $R^{NT1}R^{NT2}$N—S(=OP)$_2$—, $R^{NT1}R^{NT2}$N—C(=O)—$C_{1-4}$-alkyl-, heterocyclyl, heterocyclyl-O—, phenyl and heteroaryl, wherein each alkyl and cycloalkyl group may be optionally substituted with one or more substituents independently of each other selected from F, $H_3C$—, HO—, $H_3C$—O—, phenyl, and heterocyclyl, and
wherein heteroaryl is selected from the group consisting of pyridinyl, pyrimidinyl, pyridazinyl, pyrazinyl, thienyl, and thiazolyl; and
wherein heterocyclyl is selected from the group consisting of oxetanyl, tetrahydrofuranyl and tetrahydropyranyl, each of which may be optionally substituted with one or two $H_3C$— groups; and
wherein phenyl and heteroaryl may be optionally substituted with one substituent $L^{Ar}$.

$R^2$-G3a:

According to another embodiment the group $R^2$ is selected from the group $R^2$-G3a consisting of F, Cl, Br, I, NC—, $C_{1-4}$-alkyl-, $F_3C$—, $F_3C$—$H_2C$—, cyclopropyl, cyclobutyl, tetrahydropyran-4-yl, tetrahydropyran-4-ylmethyl-, $C_{1-4}$-alkyl-O—C(=O)—, $C_{1-3}$-alkyl-O—, thienyl, pyridyl, and phenyl, wherein the phenyl ring may be optionally monosubstituted with F, Cl, $CH_3$, or $OCH_3$.

$R^2$-G4:

According to another embodiment the group $R^2$ is selected from the group $R^2$-G4 consisting of F, Cl, NC—, $C_{1-4}$-alkyl-, $F_3C$—, cyclopropyl, cyclobutyl, $C_{1-3}$-alkyl-O—, thienyl and phenyl, wherein the phenyl ring may be optionally monosubstituted with F, Cl, $CH_3$, or $OCH_3$.

$R^2$-G4a:

According to another embodiment the group $R^2$ is selected from the group $R^2$-G4a consisting of F, Cl, Br, I, NC—, $C_{1-4}$-alkyl-, $F_3C$—, $F_3C$—$H_2C$—, cyclopropyl, cyclobutyl, $C_{1-3}$-alkyl-O—, thienyl and phenyl, wherein the phenyl ring may be optionally monosubstituted with F, Cl, $CH_3$, or $OCH_3$.

$L^P$:

$L^P$-G1:

The group $L^P$ is preferably selected from the group $L^P$-G1 as defined hereinbefore and hereinafter.

$L^P$-G2:

In another embodiment the group $L^P$ is selected from the group $L^P$-G2 consisting of F and methyl.

$L^P$-G3:

In another embodiment the group $L^P$ is selected from the group $L^P$-G3 consisting of F.

$L^Q$:

$L^Q$-G1:

The group $L^Q$ is preferably selected from the group $L^Q$-G1 as defined hereinbefore and hereinafter.

$L^Q$-G2:

In another embodiment the group $L^Q$ is selected from the group $L^Q$-G2 consisting of F, CN, OH, $H_3C-$, $F_2HC$, $F_3C$, $H_3C-O-$, $F_2HC-O-$, and $F_3C-O-$.

$L^Q$-G3:

In another embodiment the group $L^Q$ is selected from the group $L^Q$-G3 consisting of F and $H_3C-$.

$L^Q$-G4:

In another embodiment the group $L^Q$ is selected from the group $L^Q$-G4 consisting of F.

m:

The index m is an integer selected from 0, 1 or 2.

According to one embodiment the index m is 1 or 2, in particular 1.

According to another embodiment the index m is 0.

n:

The index n is an integer selected from 0, 1, 2, 3 or 4.

According to one embodiment the index n is 1 or 2, in particular 1.

According to another embodiment the index n is 0.

The following preferred embodiments of compounds of the formula I are described using generic formulae I.1 to I.4, wherein any tautomers and stereoisomers, solvates, hydrates and salts thereof, in particular the pharmaceutically acceptable salts thereof, are encompassed.

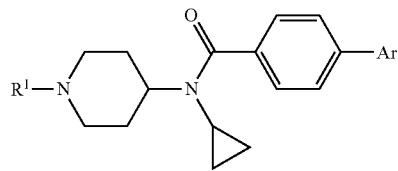

I.1

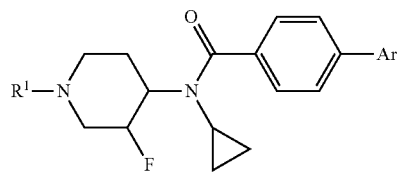

I.2

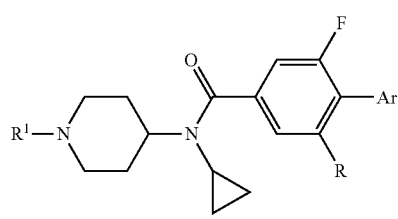

I.3

R = H, F

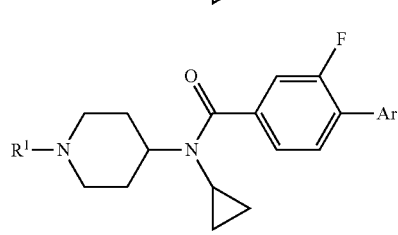

I.4 wherein the groups $R^1$ and Ar are defined as hereinbefore and hereinafter.

Examples of preferred subgeneric embodiments according to the present invention are set forth in the following table, wherein each substituent group of each embodiment is defined according to the definitions set forth hereinbefore and wherein all other substituents of the formula I are defined according to the definitions set forth hereinbefore:

| Embodiment | Formula | $R^1$- | Ar- |
|---|---|---|---|
| E-1 | I | $R^1$-G1 | Ar-G1 |
| E-2 | I | $R^1$-G2 | Ar-G2a |
| E-3 | I | $R^1$-G2 | Ar-G2b |
| E-4 | I | $R^1$-G2 | Ar-G4 |
| E-5 | I | $R^1$-G2 | Ar-G5 |
| E-6 | I.1 | $R^1$-G1 | Ar-G1 |
| E-7 | I.1 | $R^1$-G2 | Ar-G2a |
| E-8 | I.1 | $R^1$-G2 | Ar-G2b |
| E-9 | I.1 | $R^1$-G2 | Ar-G4 |
| E-10 | I.1 | $R^1$-G2 | Ar-G5 |
| E-11 | I.1 | $R^1$-G5 | Ar-G6b |
| E-12 | I.2 | $R^1$-G1 | Ar-G1 |
| E-13 | I.2 | $R^1$-G2 | Ar-G2a |
| E-14 | I.2 | $R^1$-G2 | Ar-G2b |
| E-15 | I.2 | $R^1$-G2 | Ar-G4 |
| E-16 | I.2 | $R^1$-G2 | Ar-G5 |
| E-17 | I.3 | $R^1$-G1 | Ar-G1 |
| E-18 | I.3 | $R^1$-G2 | Ar-G2a |
| E-19 | I.3 | $R^1$-G2 | Ar-G2b |
| E-20 | I.3 | $R^1$-G2 | Ar-G4 |
| E-21 | I.3 | $R^1$-G2 | Ar-G5 |
| E-22 | I.3 | $R^1$-G5a | Ar-G7a |
| E-23 | I.4 | $R^1$-G1 | Ar-G1 |
| E-24 | I.4 | $R^1$-G2 | Ar-G2a |
| E-25 | I.4 | $R^1$-G2 | Ar-G2b |
| E-26 | I.4 | $R^1$-G2 | Ar-G4 |
| E-27 | I.4 | $R^1$-G2 | Ar-G5 |
| E-28 | I.4 | $R^1$-G5a | Ar-G7a |

Particularly preferred compounds, including their tautomers and stereoisomers, the salts thereof, or any solvates or hydrates thereof, are described in the experimental section hereinafter.

The following compounds are mentioned as examples of compounds according to the invention:

Example 1

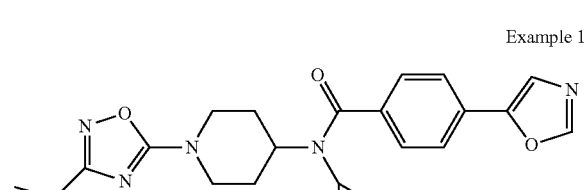

Example 2

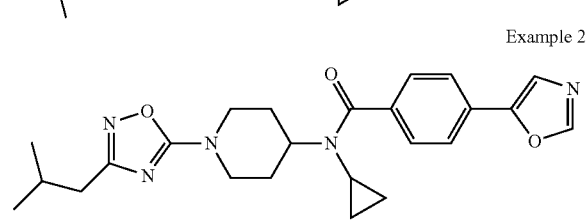

Example 3
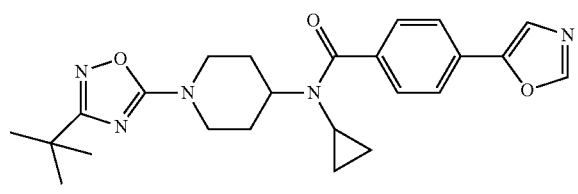
Example 4
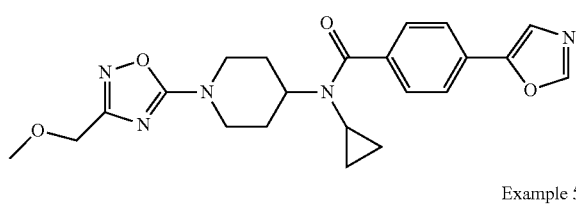
Example 5
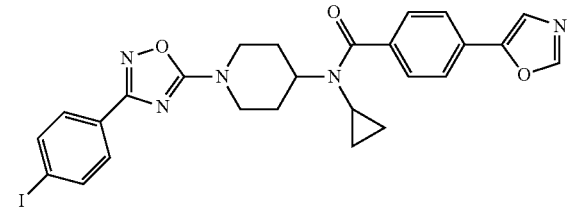
Example 6
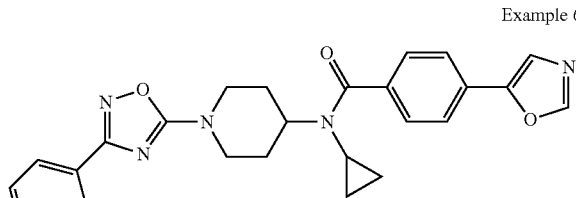
Example 7
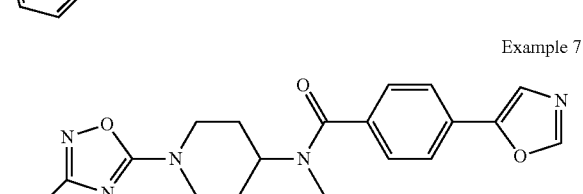
Example 8
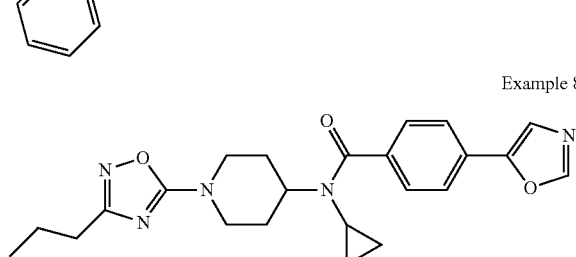
Example 9
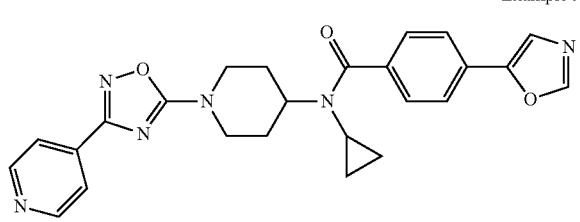
Example 10
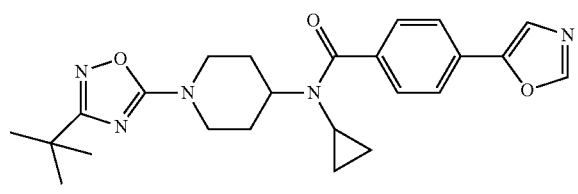
Example 11
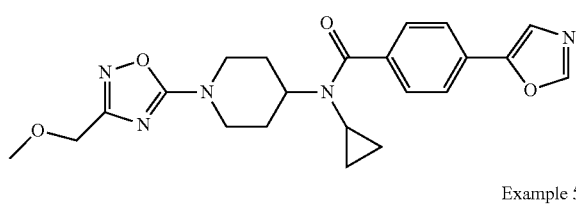
Example 12
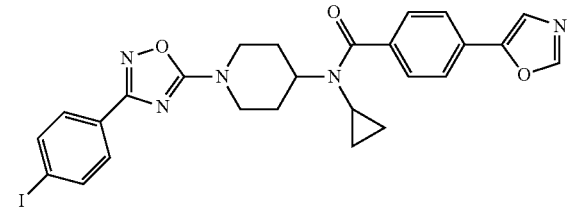
Example 13
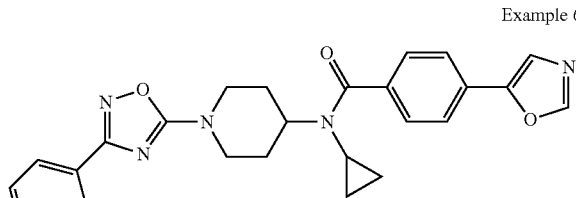
Example 14
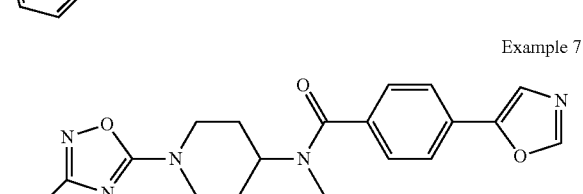
Example 15
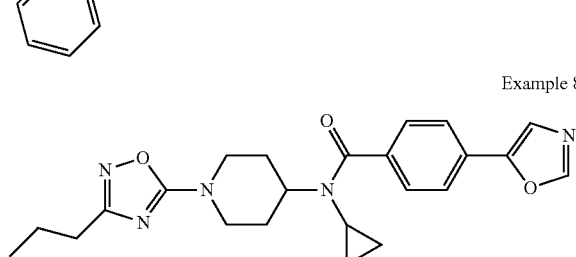
Example 16
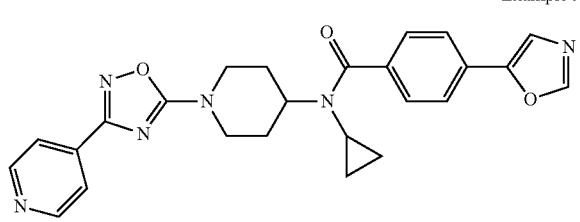

Example 17

Example 18

Example 19

Example 20

Example 21

Example 22

Example 23

Example 24

R = 4-chlorophenyl

Example 25

Example 26

Example 27

R = 4-methoxyphenyl

Example 28

Example 29

Example 30

Example 31

Example 32

Example 33

Example 34

Example 35

Example 36

Example 37

Example 38

Example 39

R = phenyl

Example 40

R = 4-bromophenyl

Example 41

Example 42

Example 43

Example 44

Example 45

Example 46
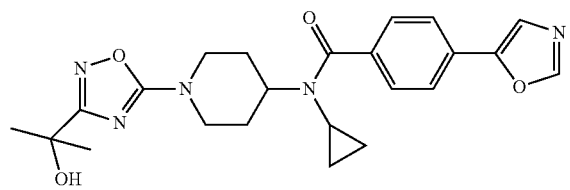
Example 47
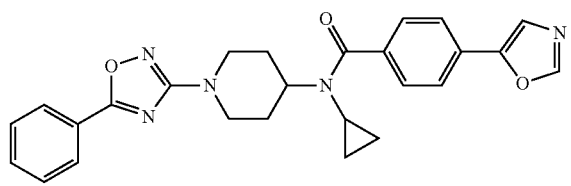
Example 48
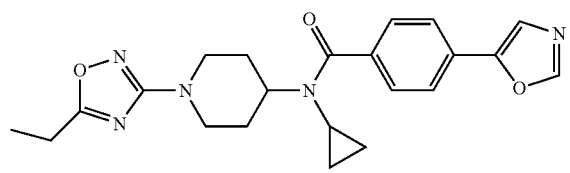
Example 49
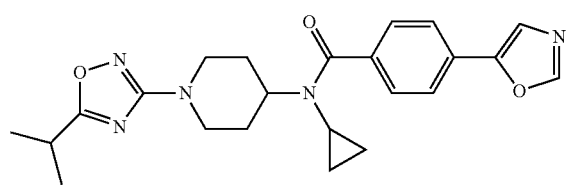
Example 50
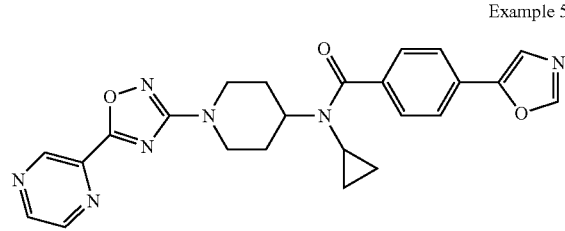
Example 51
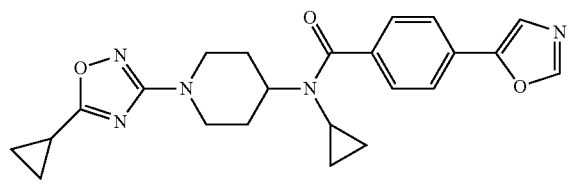
Example 52
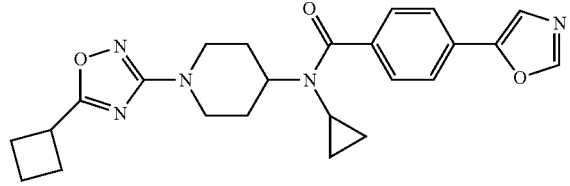
Example 53
Example 54
Example 55
Example 56
Example 57
Example 58
Example 59

Example 60

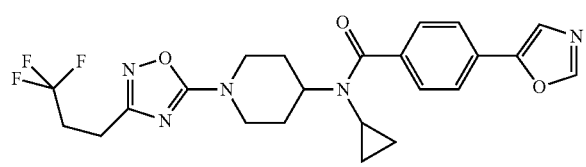

including any tautomers and stereoisomers thereof, or a salt thereof or a solvate or hydrate thereof.

The compounds according to the invention and their intermediates may be obtained using methods of synthesis which are known to the one skilled in the art and described in the literature of organic synthesis. Preferably the compounds are obtained analogously to the methods of preparation explained more fully hereinafter, in particular as described in the experimental section. In some cases the sequence adopted in carrying out the reaction schemes may be varied. Variants of these reactions that are known to the skilled man but are not described in detail here may also be used. The general processes for preparing the compounds according to the invention will become apparent to the skilled man on studying the schemes that follow. Starting compounds are commercially available or may be prepared by methods that are described in the literature or herein, or may be prepared in an analogous or similar manner. Before the reaction is carried out any corresponding functional groups in the compounds may be protected using conventional protecting groups. These protecting groups may be cleaved again at a suitable stage within the reaction sequence using methods familiar to the skilled man.

The compounds of the invention I can principally be assembled from the building blocks 1 to 5 as sketched in Scheme 1; $R^1$, $L^P$, $L^Q$, m, n, and Ar have the meanings as defined hereinbefore and hereinafter. Building blocks 1 to 5 are either known compounds that are commercially available or of which a synthesis is reported or can be synthesized in analogy to proceedings described herein or in the literature for related compounds. The order of linking the building blocks is variable and the most effective way depends on the precise decoration of the building blocks and the reactivity of the groups to be linked and may vary for each of them. In principle, almost each order of linking is conceivable, however, combining building block 1 with building block 2 followed by attachment of building block 3 and finally compound 4, optionally already bearing building block 5, is preferred in most of the cases. For varying one individual residue or for the synthesis of particular target compounds a deviating proceeding may be more appropriate.

Scheme 1

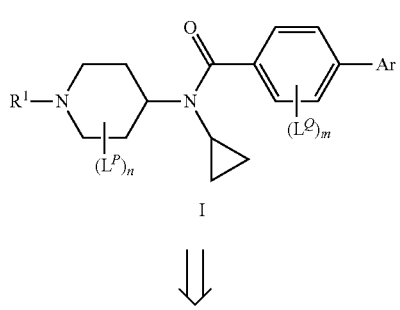

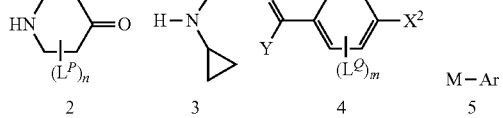

$X^1, X^2, Y$ = leaving group
M = metal or pseudo-metal group

A general way of attaching residue $R^1$ to the N atom of the piperidine of the compounds of the invention (I) or an intermediate towards them is sketched in Scheme 2; $R^1$, $L^P$, and n have the meanings as defined hereinbefore and hereinafter. The reaction may be conducted as a classical nucleophilic substitution on a heteroaromatic bearing a leaving group, such as F, Cl, Br, $SO_2C_{1-4}$-alkyl, $SO_2$aryl, and $NO_2$. The reaction partners are preferably coupled in the presence of a rather mild base, e.g. $Na_2CO_3$, $K_2CO_3$, or $Cs_2CO_3$, pyridine, 4-dimethylaminopyridine, triethylamine, ethyldiisopropylamine, 1,8-diazabicylo[5.4.0]undec-7-ene, in toluene, tetrahydrofuran, 1,4-dioxane, 1,2-dimethoxyethane, acetonitrile, N,N-dimethylformamide, N,N-dimethylacetamide, N-methylpyrrolidinone, water, methanol, ethanol, isopropanol, dimethyl sulfoxide, or mixtures thereof, at 20 to 220° C. by conventional or microwave heating. Alternatively, the piperidine 2' may be transformed into the corresponding metal piperidide by deprotonation with a strong base, e.g. butyl lithium, NaH, or KH, prior to the addition of the electrophile 1'.

In certain cases the use of transition metals as catalysts for the coupling may be beneficial or even essential. The leaving group X in compound 1' is then preferably Cl, Br, I, $OSO_2CH_3$, $OSO_2$tolyl, and $OSO_2CF_3$. The reactions are preferably conducted with a transition metal derived catalyst which is preferably based on copper or palladium. The catalyst may be an elemental form of the transition metal, such as palladium on charcoal or nanoparticles of palladium, a salt of the transition metal, such as CuCl, CuBr, CuI, $Cu(O_3SCF_3)_2$, $Cu(O_2CCH_3)_2$, $PdCl_2$, $PdBr_2$, $Pd(O_2CCH_3)_2$, and $Pd(O_2CCF_3)_2$, or a complex of the transition metal, such $Pd_2$(dibenzylideneacetone)$_3$, all of which may optionally be combined with additional ligands, such as phosphines, e.g. triphenylphosphine, tritolylphosphine, tri-cyclohexylphosphine, tri-tert-butylphosphine, 1,1'-bis(diphenylphosphino) ferrocene, optionally substituted biphenyl-di-tert-butylphosphines or biphenyl-dicyclohexyl-phosphines, 2,2'-bis (diphenylphosphinyl)-1,1'-binaphthyl, 1,3-disubstituted imidazole or imidazolidine carbenes, phosphites, 1,3-diketones, nitriles, or alkenes. The coupling reaction is preferably conducted in the presence of a base, such as NaOtBu, KOtBu, $LiN(SiMe_3)_2$, $K_2CO_3$, $Cs_2CO_3$, or $K_3PO_4$, in toluene, benzene, tetrahydrofuran, 1,4-dioxane, 1,2-dimethoxyethane, N,N-dimethylformamide, N,N-dimethylacetamide, N-methylpyrrolidinone, dimethyl sulfoxide, tBuOH, or mixtures thereof, at 0 to 180° C.

Alternatively, particular residues $R^1$ in compound 6 or any other intermediate towards compound I or compound I itself, such as [1,2,4]oxadiazoles and [1,2,4]triazoles, may be assembled from the corresponding cyanamide of compound 2' or another corresponding intermediate and N-hydroxyamidine or N-aminoamidine, respectively, as described, for example, in the experimental part.

Scheme 2

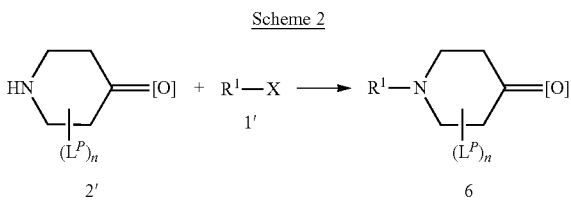

[O] = O or protective group for =O, e.g., OCH$_2$CH$_2$O
X = leaving group, e.g., F, Cl, Br, I, OSO$_2$CF$_3$, OSO$_2$C$_{1-4}$-alkyl, OSO$_2$-aryl, SO$_2$C$_{1-2}$-alkyl, NO$_2$ The linkage between the piperidine and the cyclopropylamine fragment is preferably established via reductive amination from a piperidinone, such as 6', and cyclopropylamine (3) (Scheme 3); R$^1$, L$^P$, and n have the meanings as defined hereinbefore and hereinafter. Suited reducing agents may be complex metal hydrides, such as sodium borohydride, lithium borohydride, sodium triacetoxyborohydride, or sodium cyanoborohydride, optionally used in combination with an acid, e.g. acetic acid, or hydrogen that is employed in the presence of a transition metal catalyst, e.g. palladium on charcoal or Raney-Ni.

Scheme 3

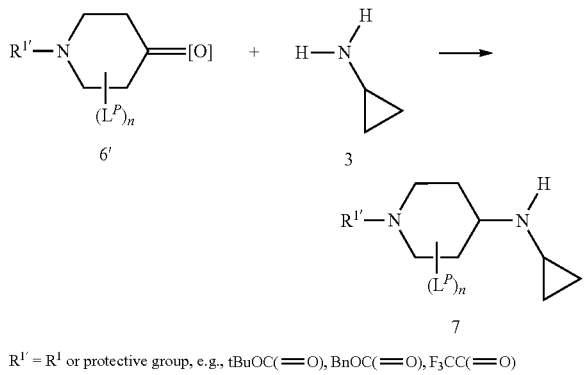

R$^{1'}$ = R$^1$ or protective group, e.g., tBuOC(=O), BnOC(=O), F$_3$CC(=O)

The amide linkage in compounds I or any intermediate towards I of the carboxylic carbon atom and the N bearing the cyclopropyl group is a routine transformation in organic synthesis with a plethora of methods and strategies known (Scheme 4); R$^1$, L$^P$, L$^Q$, m, n, and Ar have the meanings as defined hereinbefore and hereinafter. The carboxylic acid may be transformed into a sufficiently reactive derivative to be coupled with the amine in a separate reaction step or in situ. Suited derivatives of the carboxylic acid for the former proceeding may be, for example, carboxylic chlorides, fluorides, cyanides, anhydrides, mixed anhydrides, imidazolides, oxybenzotriazolides, pentafluorophenyl esters, or 4-nitrophenyl esters. In situ activation of the carboxylic acid may be achieved with e.g. 2-(1H-benzotriazol-1-yl)-1,1,3,3-tetramethyluronium tetrafluoroborate or 2-(7-azabenzotriazol-1-yl)-1,1,3,3-tetramethyluronium hexafluorophosphate. The couplings are preferably conducted in the presence of a base, e.g. ethyl-diisopropyl-amine, triethylamine, imidazole, pyridine, potassium carbonate, or calcium oxide, and/or another additive, such as 4-dimethylaminopyridine or 1-hydroxybenzotriazol, in solvents, preferably selected from tetrahydrofuran, 1,2-dimethoxyethane, ether, 1,4-dioxane, N,N-dimethylformamide, N,N-dimethylacetamide, N-methylpyrrolidinone, acetonitrile, ethyl acetate, dichloromethane, 1,2-dichloroethane, toluene, benzene, hexanes, and mixtures thereof, preferably at −10 to 140° C.

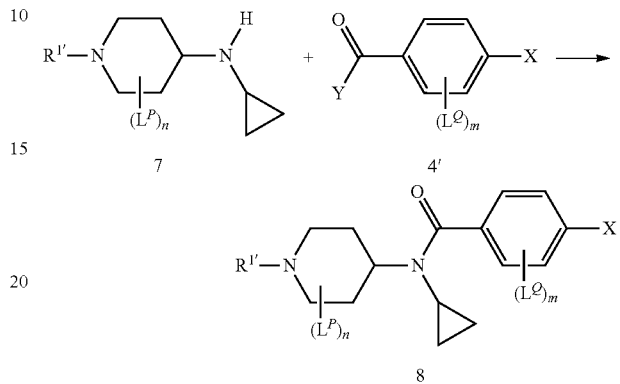

R$^{1'}$ = R$^1$ or protective group, e.g., tBuOC(=O), BnOC(=O), F$_3$CC(=O)
X = Ar or leaving group, e.g., Cl, Br, I, OSO$_2$CF$_3$, OSO$_2$Me
Y = leaving group, e.g., F, Cl, imidazolide, tBuOC(=O), iPrC(=O)O, benzotriazol-1-yl-O, pentafluorophenoxy, 4-nitrophenoxy Attaching Ar to the benzamide moiety in I or an intermediate towards I, e.g. compound 9, may be accomplished as depicted in Scheme 5; L$^Q$, m, and Ar have the meanings as defined hereinbefore and hereinafter. Compound 9 is preferably employed as the electrophilic component bearing a leaving group, such as Cl, Br, I, F$_3$CSO$_3$, H$_3$CSO$_3$, and PhSO$_3$, and Ar as the nucleophilic partner bearing a metal or pseudo metal group, e.g. B(OH)$_2$, BF$_3$K, B(OCMe$_2$CMe$_2$O), ZnCl, ZnBr, and ZnI. The coupling of the two components is preferably mediated by a transition metal species derived from Fe, Cu, Ni, or Pd. The active catalyst may be a complex of the transition metal with ligands, such as phosphines, e.g. tri-tert-butylphosphine, tricyclohexyl-phosphine, optionally substituted biphenyl-dicyclohexylphosphines or biphenyl-di-tert-butylphosphines, 1,1'-bis(diphenylphosphino)-ferrocene, triphenylphosphine, tritolylphosphine, or trifurylphosphine, phosphites, 1,3-disubstituted imdiazole or imidazolidine carbenes, dibenzylideneacetone, allyl, or nitriles, an elemental form of the transition metal, such as Pd on carbon or nanoparticles of Fe or Pd, a salt, such as fluoride, chloride, bromide, acetate, triflate, or trifluoroacetate, or a combination of the different species mentioned. Depending on the nature of the electrophile and nucleophile additives, such as halide salts, e.g. LiCl, KF, and nBu$_4$NF, hydroxide sources, e.g. KOH, K$_2$CO$_3$, silver salts, such as Ag$_2$O and Ag(O$_3$SCF$_3$)$_2$, and/or Cu salts, such as copper thiophene-2-carboxylate, may be advantageous or even essential. The coupling is preferably conducted in benzene, toluene, ether, tetrahydrofuran, 1,2-dimethoxyethane, 1,4-dioxane, N,N-dimethylformamide, N,N-dimethylacetamide, N-methylpyrrolidinone, alcohol, water, or mixtures thereof, at −10 to 180° C. The reactivity of the two building blocks may be reversed, i.e. compound 9 is the nucleophile bearing the metal or pseudo metal residue and Ar is the electrophile bearing the leaving group, to access the same products under analogous reaction conditions.

Scheme 5

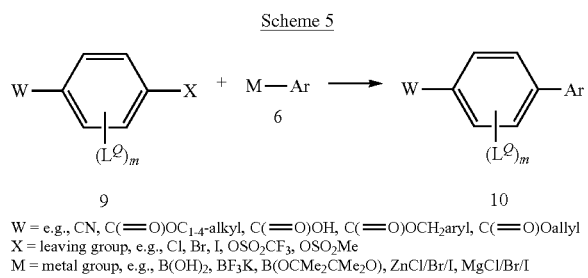

W = e.g., CN, C(=O)OC$_{1-4}$-alkyl, C(=O)OH, C(=O)OCH$_2$aryl, C(=O)Oallyl
X = leaving group, e.g., Cl, Br, I, OSO$_2$CF$_3$, OSO$_2$Me
M = metal group, e.g., B(OH)$_2$, BF$_3$K, B(OCMe$_2$CMe$_2$O), ZnCl/Br/I, MgCl/Br/I The synthetic routes presented may rely on the use of protecting groups. For example reactive groups present, such as hydroxy, carbonyl, carboxy, amino, alkylamino, or imino, may be protected during the reaction by conventional protecting groups which are cleaved again after the reaction. Suitable protecting groups for the respective functionalities and their removal are well known to the one skilled in the art and are described in the literature of organic synthesis.

The compounds of general formula I may be resolved into their enantiomers and/or diastereomers as mentioned before. Thus, for example, cis/trans mixtures may be resolved into their cis and trans isomers and racemic compounds may be separated into their enantiomers.

The cis/trans mixtures may be resolved, for example, by chromatography into the cis and trans isomers thereof. The compounds of general formula I which occur as racemates may be separated by methods known per se into their optical antipodes and diastereomeric mixtures of compounds of general formula I may be resolved into their diastereomers by taking advantage of their different physico-chemical properties using methods known per se, e.g. chromatography and/or fractional crystallization; if the compounds obtained thereafter are racemates, they may be resolved into the enantiomers as mentioned above.

The racemates are preferably resolved by column chromatography on chiral phases or by crystallization from an optically active solvent or by reacting with an optically active substance which forms salts or derivatives such as esters or amides with the racemic compound. Salts may be formed with enantiomerically pure acids for basic compounds and with enantiomerically pure bases for acidic compounds. Diastereomeric derivatives are formed with enantiomerically pure auxiliary compounds, e.g. acids, their activated derivatives, or alcohols. Separation of the diastereomeric mixture of salts or derivatives thus obtained may be achieved by taking advantage of their different physico-chemical properties, e.g. differences in solubility; the free antipodes may be released from the pure diastereomeric salts or derivatives by the action of suitable agents. Optically active acids in common use for such a purpose are e.g. the D- and L-forms of tartaric acid, dibenzoyltartaric acid, ditoloyltartaric acid, malic acid, mandelic acid, camphorsulfonic acid, glutamic acid, aspartic acid, or quinic acid. Optically active alcohols applicable as auxiliary residues may be, for example, (+) or (−)-menthol and optically active acyl groups in amides may be, for example, (+)- or (−)-menthyloxycarbonyl.

As mentioned above, the compounds of formula I may be converted into salts, particularly for pharmaceutical use into the pharmaceutically acceptable salts. As used herein, "pharmaceutically acceptable salts" refer to derivatives of the disclosed compounds wherein the parent compound is modified by making acid or base salts thereof.

Terms and Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to.

The terms "compound(s) according to this invention", "compound(s) of formula I", "compound(s) of the invention" and the like denote the compounds of the formula I according to the present invention including their tautomers, stereoisomers and mixtures thereof and the salts thereof, in particular the pharmaceutically acceptable salts thereof, and the solvates and hydrates of such compounds, including the solvates and hydrates of such tautomers, stereoisomers and salts thereof.

The terms "treatment" and "treating" embraces both preventative, i.e. prophylactic, or therapeutic, i.e. curative and/or palliative, treatment. Thus the terms "treatment" and "treating" comprise therapeutic treatment of patients having already developed said condition, in particular in manifest form. Therapeutic treatment may be symptomatic treatment in order to relieve the symptoms of the specific indication or causal treatment in order to reverse or partially reverse the conditions of the indication or to stop or slow down progression of the disease. Thus the compositions and methods of the present invention may be used for instance as therapeutic treatment over a period of time as well as for chronic therapy. In addition the terms "treatment" and "treating" comprise prophylactic treatment, i.e. a treatment of patients at risk to develop a condition mentioned hereinbefore, thus reducing said risk.

When this invention refers to patients requiring treatment, it relates primarily to treatment in mammals, in particular humans.

The term "therapeutically effective amount" means an amount of a compound of the present invention that (i) treats or prevents the particular disease or condition, (ii) attenuates, ameliorates, or eliminates one or more symptoms of the particular disease or condition, or (iii) prevents or delays the onset of one or more symptoms of the particular disease or condition described herein.

The terms "modulated" or "modulating", or "modulate(s)", as used herein, unless otherwise indicated, refers to the activation of the G-protein-coupled receptor GPR119 with one or more compounds of the present invention.

The terms "mediated" or "mediating" or "mediate", as used herein, unless otherwise indicated, refers to the (i) treatment, including prevention of the particular disease or condition, (ii) attenuation, amelioration, or elimination of one or more symptoms of the particular disease or condition, or (iii) prevention or delay of the onset of one or more symptoms of the particular disease or condition described herein.

The term "substituted" as used herein, means that any one or more hydrogens on the designated atom, radical or moiety is replaced with a selection from the indicated group, provided that the atom's normal valence is not exceeded, and that the substitution results in an acceptably stable compound.

In the groups, radicals, or moieties defined below, the number of carbon atoms is often specified preceding the group, for example, $C_{1-6}$-alkyl means an alkyl group or radical having 1 to 6 carbon atoms. In general, for groups comprising two or more subgroups, the last named subgroup is the radical attachment point, for example, the substituent "aryl-$C_{1-3}$-alkyl-" means an aryl group which is bound to a $C_{1-3}$-alkyl-group, the latter of which is bound to the core or to the group to which the substituent is attached.

In case a compound of the present invention is depicted in form of a chemical name and as a formula in case of any discrepancy the formula shall prevail.

An asterisk may be used in sub-formulas to indicate the bond which is connected to the core molecule as defined.

The numeration of the atoms of a substituent starts with the atom which is closest to the core or the group to which the substituent is attached.

For example, the term "3-carboxypropyl-group" represents the following substituent:

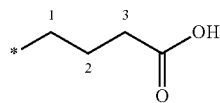

wherein the carboxy group is attached to the third carbon atom of the propyl group. The terms "1-methylpropyl-", "2,2-dimethylpropyl-" or "cyclopropylmethyl-" group represent the following groups:

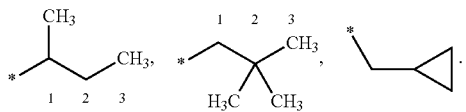

The asterisk may be used in sub-formulas to indicate the bond which is connected to the core molecule as defined.

In a definition of a group the term "wherein each X, Y and Z group is optionally substituted with" and the like denotes that each group X, each group Y and each group Z either each as a separate group or each as part of a composed group may be substituted as defined. For example a definition "$R^{ex}$ denotes H, $C_{1-3}$-alkyl, $C_{3-6}$-cycloalkyl, $C_{3-6}$-cycloalkyl-$C_{1-3}$-alkyl or $C_{1-3}$-alkyl-O—, wherein each alkyl group is optionally substituted with one or more $L^{ex}$" or the like means that in each of the beforementioned groups which comprise the term alkyl, i.e. in each of the groups $C_{1-3}$-alkyl, $C_{3-6}$-cycloalkyl-$C_{1-3}$-alkyl and $C_{1-3}$-alkyl-O—, the alkyl moiety may be substituted with $L^{ex}$ as defined.

Unless specifically indicated, throughout the specification and the appended claims, a given chemical formula or name shall encompass tautomers and all stereo, optical and geometrical isomers (e.g. enantiomers, diastereomers, E/Z isomers etc. . . . ) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof.

Salts of acids which for example are useful for purifying or isolating the compounds of the present invention (e.g. trifluoro acetate salts) also comprise a part of the invention.

The term halogen generally denotes fluorine, chlorine, bromine and iodine.

The term "$C_{1-n}$-alkyl", wherein n is an integer from 1 to n, either alone or in combination with another radical denotes an acyclic, saturated, branched or linear hydrocarbon radical with 1 to n C atoms. For example, the term $C_{1-5}$-alkyl embraces the radicals $H_3C$—, $H_3C$—$CH_2$—, $H_3C$—$CH_2$—$CH_2$—, $H_3C$—$CH(CH_3)$—, $H_3C$—$CH_2$—$CH_2$—$CH_2$—, $H_3C$—$CH_2$—$CH(CH_3)$—, $H_3C$—$CH(CH_3)$—$CH_2$—, $H_3C$—$C(CH_3)_2$—, $H_3C$—$CH_2$—$CH_2$—$CH_2$—$CH_2$—, $H_3C$—$CH_2$—$CH_2$—$CH(CH_3)$—, $H_3C$—$CH_2$—$CH(CH_3)$—$CH_2$—, $H_3C$—$CH(CH_3)$—$CH_2$—$CH_2$—, $H_3C$—$CH_2$—$C(CH_3)_2$—, $H_3C$—$C(CH_3)_2$—$CH_2$—, $H_3C$—$CH(CH_3)$—$CH(CH_3)$— and $H_3C$—$CH_2$—$CH(CH_2CH_3)$—.

The term "$C_{1-n}$-alkylene" wherein n is an integer 1 to n, either alone or in combination with another radical, denotes an acyclic, straight or branched chain divalent alkyl radical containing from 1 to n carbon atoms. For example, the term $C_{1-4}$-alkylene includes —$(CH_2)$—, —$(CH_2$—$CH_2)$—, —$(CH(CH_3))$—, —$(CH_2$—$CH_2$—$CH_2)$—, —$(C(CH_3)_2)$—, —$(CH(CH_2CH_3))$—, —$(CH(CH_3)$—$CH_2)$—, —$(CH_2$—$CH(CH_3))$—, —$(CH_2$—$CH_2$—$CH_2$—$CH_2)$—, —$(CH_2$—$CH_2$—$CH(CH_3))$—, —$(CH(CH_3)$—$CH_2$—$CH_2)$—, —$(CH_2$—$CH(CH_3)$—$CH_2)$—, —$(CH_2$—$C(CH_3)_2)$—, —$(C(CH_3)_2$—$CH_2)$—, —$(CH(CH_3)$—$CH(CH_3))$—, —$(CH_2$—$CH(CH_2CH_3))$—, —$(CH(CH_2CH_3)$—$CH_2)$—, —$(CH(CH_2CH_3))$—, —$(CHCH(CH_3)_2)$— and —$C(CH_3)(CH_2CH_3)$—.

The term "$C_{2-n}$-alkenyl", is used for a group as defined in the definition for "$C_{1-n}$-alkyl" with at least two carbon atoms, if at least two of those carbon atoms of said group are bonded to each other by a double bond. For example the term $C_{2-3}$-alkenyl includes —$CH$=$CH_2$, —$CH$=$CH$—$CH_3$, —$CH_2$—$CH$=$CH_2$.

The term "$C_{2-n}$-alkenylene" is used for a group as defined in the definition for "$C_{1-n}$-alkylene" with at least two carbon atoms, if at least two of those carbon atoms of said group are bonded to each other by a double bond. For example the term $C_{2-3}$-alkenylene includes —$CH$=$CH$—, —$CH$=$CH$—$CH_2$—, —$CH_2$—$CH$=$CH$—.

The term "$C_{2-n}$-alkynyl", is used for a group as defined in the definition for "$C_{1-n}$-alkyl" with at least two carbon atoms, if at least two of those carbon atoms of said group are bonded to each other by a triple bond. For example the term $C_{2-3}$-alkynyl includes —$C$≡$CH$, —$C$≡$C$—$CH_3$, —$CH_2$—$C$≡$CH$.

The term "$C_{2-n}$-alkynylene" is used for a group as defined in the definition for "$C_{1-n}$-alkylene" with at least two carbon atoms, if at least two of those carbon atoms of said group are bonded to each other by a triple bond. For example the term $C_{2-3}$-alkynylene includes —$C$≡$C$—, —$C$≡$C$—$CH_2$—, —$CH_2$—$C$≡$C$—.

The term "$C_{3-n}$-carbocyclyl" as used either alone or in combination with another radical, denotes a monocyclic, bicyclic or tricyclic, saturated or unsaturated hydrocarbon radical with 3 to n C atoms. The hydrocarbon radical is preferably nonaromatic. Preferably the 3 to n C atoms form one or two rings. In case of a bicyclic or tricyclic ring system the rings may be attached to each other via a single bond or may be fused or may form a spirocyclic or bridged ring system. For example the term $C_{3-10}$-carbocyclyl includes $C_{3-10}$-cycloalkyl, $C_{3-10}$-cycloalkenyl, octahydropentalenyl, octahydroindenyl, decahydronaphthyl, indanyl, tetrahydronaphthyl. Most preferably the term $C_{3-n}$-carbocyclyl denotes $C_{3-n}$-cycloalkyl, in particular $C_{3-7}$-cycloalkyl.

The term "$C_{3-n}$-cycloalkyl", wherein n is an integer 4 to n, either alone or in combination with another radical denotes a cyclic, saturated, unbranched hydrocarbon radical with 3 to n C atoms. The cyclic group may be mono-, bi-, tri- or spirocyclic, most preferably monocyclic. Examples of such cycloalkyl groups include cyclopropyl, cyclobutyl, cyclopentyl, cyclohexyl, cycloheptyl, cyclooctyl, cyclononyl, cyclododecyl, bicyclo[3.2.1]octyl, spiro[4.5]decyl, norpinyl, norbonyl, norcaryl, adamantyl, etc.

The term bicyclic includes spirocyclic.

The term "$C_{3-n}$-cycloalkenyl", wherein n is an integer 3 to n, either alone or in combination with another radical, denotes a cyclic, unsaturated but nonaromatic, unbranched hydrocarbon radical with 3 to n C atoms, at least two of which are bonded to each other by a double bond. For example the term $C_{3-7}$-cycloalkenyl includes cyclobutenyl, cyclopentenyl, cyclopentadienyl, cyclohexenyl, cyclohexadienyl, cycloheptenyl, cycloheptadienyl and cycloheptatrienyl.

The term "aryl" as used herein, either alone or in combination with another radical, denotes a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, indanyl, indenyl, naphthyl, anthracenyl, phenanthrenyl, tetrahydronaphthyl and dihydronaphthyl. More preferably the term "aryl" as used herein, either alone or in combination with another radical, denotes phenyl or naphthyl, most preferably phenyl.

The term "heterocyclyl" means a saturated or unsaturated mono-, bi-, tri- or spirocarbocyclic, preferably mono-, bi- or spirocyclic-ring system containing one or more heteroatoms selected from N, O or S(O)$_r$ with r=0, 1 or 2, which in addition may have a carbonyl group. More preferably the term "heterocyclyl" as used herein, either alone or in combination with another radical, means a saturated or unsaturated, even more preferably a saturated mono-, bi- or spirocyclic-ring system containing 1, 2, 3 or 4 heteroatoms selected from N, O or S(O)$_r$ with r=0, 1 or 2 which in addition may have a carbonyl group. The term "heterocyclyl" is intended to include all the possible isomeric forms. Examples of such groups include aziridinyl, oxiranyl, azetidinyl, oxetanyl, pyrrolidinyl, tetrahydrofuranyl, piperidinyl, tetrahydropyranyl, azepanyl, piperazinyl, morpholinyl, tetrahydrofuranonyl, tetrahydropyranonyl, pyrrolidinonyl, piperidinonyl, piperazinonyl, morpholinonyl.

Thus, the term "heterocyclyl" includes the following exemplary structures which are not depicted as radicals as each form may be attached through a covalent bond to any atom so long as appropriate valences are maintained:

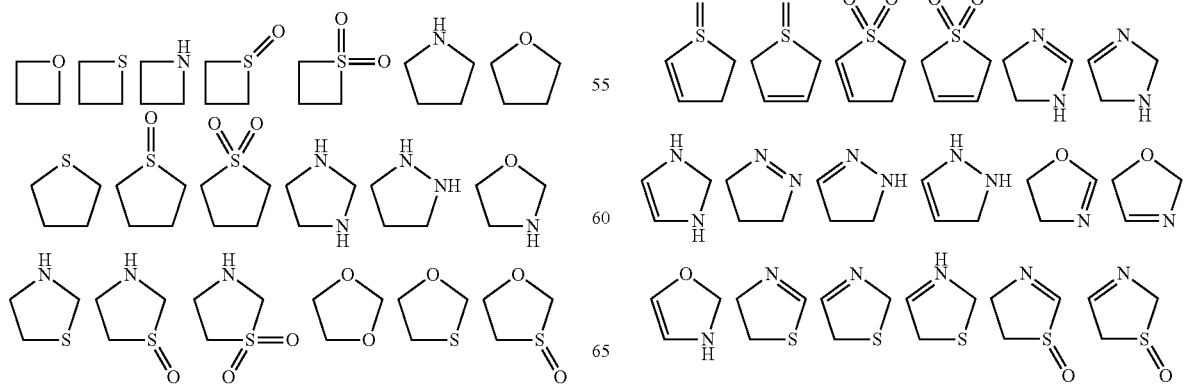

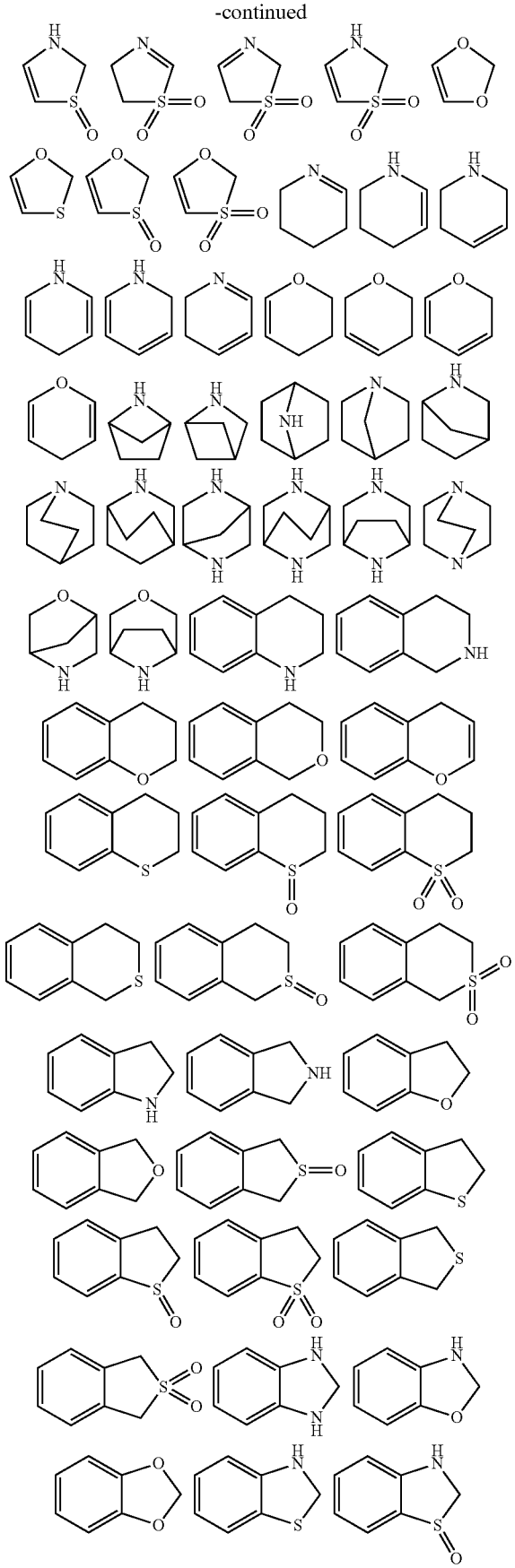
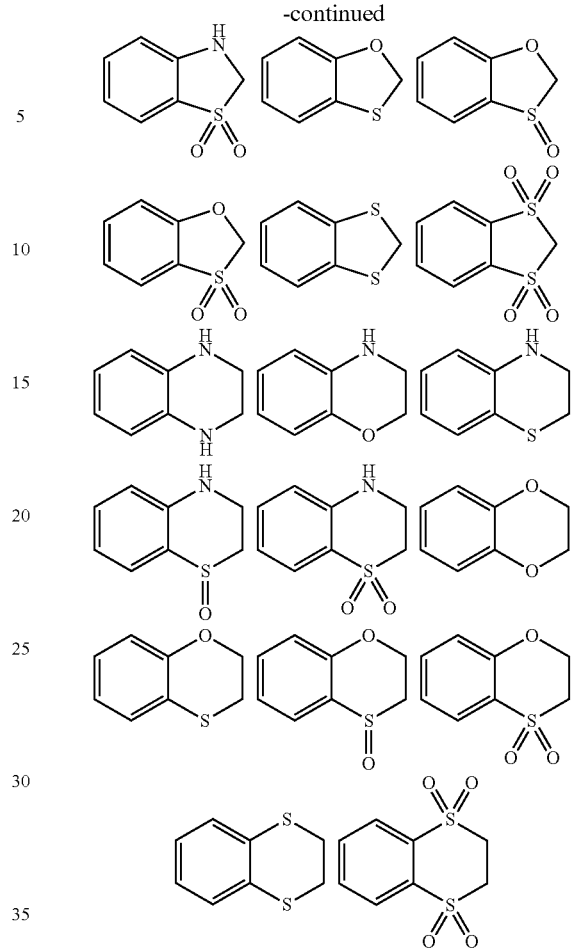

The term "heteroaryl" means a mono- or polycyclic, preferably mono- or bicyclic ring system containing one or more heteroatoms selected from N, O or S(O)$_r$ with r=0, 1 or 2 wherein at least one of the heteroatoms is part of an aromatic ring, and wherein said ring system may have a carbonyl group. More preferably the term "heteroaryl" as used herein, either alone or in combination with another radical, means a mono- or bicyclic ring system containing 1, 2, 3 or 4 heteroatoms selected from N, O or S(O)$_r$ with r=0, 1 or 2 wherein at least one of the heteroatoms is part of an aromatic ring, and wherein said ring system may have a carbonyl group. The term "heteroaryl" is intended to include all the possible isomeric forms.

Thus, the term "heteroaryl" includes the following exemplary structures which are not depicted as radicals as each form may be attached through a covalent bond to any atom so long as appropriate valences are maintained:

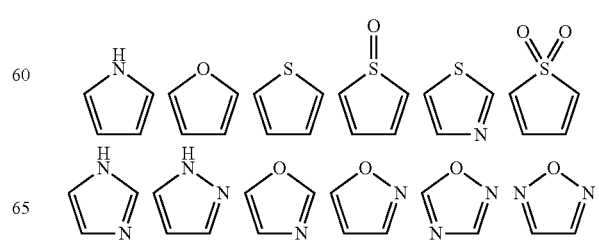

-continued

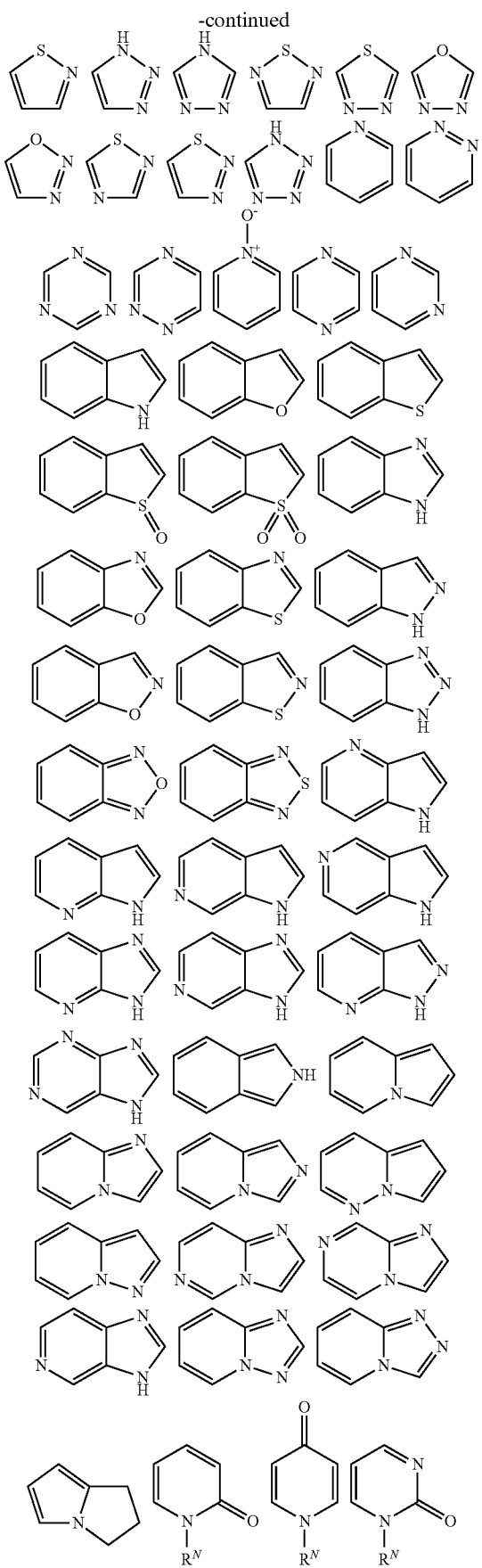

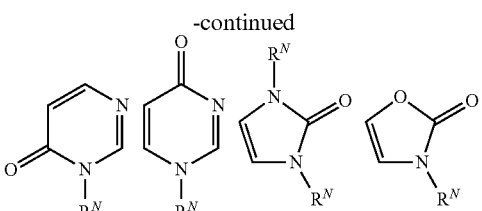

$R^N$ = H or residue attached via a C atom

Many of the terms given above may be used repeatedly in the definition of a formula or group and in each case have one of the meanings given above, independently of one another.

Pharmacological Activity

The activity of the compounds of the invention may be demonstrated using the following assay:

The compounds of formula I according to the invention modulate the activity of the G-protein-coupled receptor GPR119. The effect of the compounds on the activation of GPR119 and on the stimulation of intracellular cAMP concentration is determined using the AlphaScreen cAMP Assay Kit (Cat. No. #6760625R) made by PerkinElmer.

MIN6 cells [Miyazaki J et al. Endocrinology. 1990 July; 127(1):126-32] are stably transfected with an expression vector for human GPR119 cDNA (Acc. No. NP_848566). Min-6/hGPR119 cells are cultured in DMEM, 10% FBS, 50 µM β-mercaptoethanol, 0.3 mg/mL Geniticin, 2 mM GlutaMAX at 37° C. 5% CO2. For the assay, the cells are seeded in Optiplates (white, 384-well, 160 W-barcoded, TC, sterile with lid, Cat. No. #6007688 (Perkin Elmer); 10000 cells/well; 50 µl). The plates covered with lids are then incubated for 24 hours at 37° C./5% $CO_2$. After the medium is aspirated from the wells completely, 10 µl of the test compound are added, the compounds are diluted using stimulating buffer (140 mM NaCl, 3.6 mM KCl, 0.5 mM $NaH_2PO_4$, 0.5 mM $MgSO_4$, 1.5 mM $CaCl_2$, 10 mM Hepes, 5 mM $NaHCO_3$; pH 7.4. 0.5 mM IBMX and 0.1% BSA, the final DMSO concentration is 1%). After 45 minutes incubation at room temperature (approx. 20° C.), the cAMP concentrations are determined using the AlphaScreen cAMP Assay Kit (Cat. No. #6760625R from PerkinElmer). 10 µl of Biotin-cAMP (final concentration 1 U/well in lysing buffer (5 mM Hepes (pH 7.4), 0.1% BSA, 0.5% Tween) and 10 µL Bead solution (final concentration 1 U/well in lysing buffer) are added. The plates are incubated for another 2 hours at room temperature. The cAMP concentrations are calculated using a cAMP standard curve from the Alpha Screen Counts. The data analysis is carried out by calculating the $EC_{50}$ value and the maximum value based on a positive control, using suitable software (Graphpad Prism). The compounds according to the invention increase the intracellular cAMP level in the range of 3-5.

The compounds according to the invention typically have $EC_{50}$ values in the range from about 1 nM to about 10 µM, preferably from 1 nM to 1 µM, preferably less than 1 µM, particularly preferably less than 500 nM, most particularly preferably less than 100 nM.

$EC_{50}$ values (cAMP assay) for compounds according to the invention are shown in the following table. The number of the compound corresponds to the number of the Example in the experimental section.

| Example No. | EC$_{50}$ [nM] | Example No. | EC$_{50}$ [nM] | Example No. | EC$_{50}$ [nM] | Example No. | EC$_{50}$ [nM] |
|---|---|---|---|---|---|---|---|
| 1 | 15 | 16 | 206 | 31 | 38 | 46 | 731 |
| 2 | 15 | 17 | 23 | 32 | 38 | 47 | 37 |
| 3 | 19 | 18 | 275 | 33 | 276 | 48 | 47 |
| 4 | 160 | 19 | 32 | 34 | 85 | 49 | 14 |
| 5 | 14 | 20 | 393 | 35 | 53 | 50 | 277 |
| 6 | 23 | 21 | 143 | 36 | 83 | 51 | 56 |
| 7 | 69 | 22 | 60 | 37 | 55 | 52 | 17 |
| 8 | 36 | 23 | 44 | 38 | 204 | 53 | 99 |
| 9 | 80 | 24 | 232 | 39 | 87 | 54 | 43 |
| 10 | 13 | 25 | 17 | 40 | 11 | 55 | 1146 |
| 11 | 97 | 26 | 47 | 41 | 38 | 56 | 159 |
| 12 | 51 | 27 | 71 | 42 | 17 | 57 | 22 |
| 13 | 26 | 28 | 676 | 43 | 46 | 58 | 629 |
| 14 | 27 | 29 | 78 | 44 | 31 | 59 | 23 |
| 15 | 153 | 30 | 19 | 45 | 259 | 60 | 50 |
| 61 | 52 | 69 | 198 | 77 | 115 | 85 | 449 |
| 62 | 16 | 70 | 191 | 78 | 43 | 86 | 139 |
| 63 | 3 | 71 | 11 | 79 | 75 | 87 | 25 |
| 64 | 4 | 72 | 864 | 80 | 179 | 88 | 71 |
| 65 | 7 | 73 | 38 | 81 | 498 | 89 | 34 |
| 66 | 210 | 74 | 8 | 82 | 116 | | |
| 67 | 188 | 75 | 87 | 83 | 10 | | |
| 68 | 211 | 76 | 165 | 84 | 116 | | |

Alternatively, the effect of the compounds on the activation of GPR119 are determined as follows:

Quantitative detection of cAMP accumulation from cells expressing human GPR119 receptor is achieved using Perkin Elmer's LANCE cAMP-384 Kit (Cat#AD0264) according to the manufacturer's protocol. Briefly, HEK293 cells stably expressing a mutant form of the human GPR119 receptor as assay tool (Methionine 1 replaced with the amino acid sequence MKTIIALSYIFCLVFADYKDDDDA, and T327 & S329 changed to alanines; SEQ ID No. 1) are grown to 50-70% confluency in cell culture media (DMEM, 10% heat inactivated Fetal Bovine Serum, 50 I.U./mL penicillin, 50 µg/mL streptomycin, 10 mM HEPES, 20 µg/mL G418 Sulfate). On the day of the assay, GPR119 stable HEK293 cells are lifted from the tissue culture plate and 1000 cells/well are incubated along with various concentrations of test compounds for 20 min at 37° C. Detection Buffer (50 mM HEPES, 10 mM calcium chloride, 0.35% Triton X-100, 1 mg/mL BSA) containing cAMP-specific antibody is then added to all wells and allowed to equilibrate in the dark for 10 minutes at room temperature. Upon equilibration, Detection Buffer containing europium-labeled cAMP tracer complex is added to all wells and allowed to react for 1 hour at room temperature. After 1 hour, bound europium-labeled cAMP tracer is measured using a PerkinElmer Envision plate reader. The quantity of cAMP generated in each well is derived from a standard curve. EC$_{50}$ is determined using nonlinear regression analysis of the cAMP values over a range of agonist concentration (12 points spanning the range from 30 µM to 100 pM).

EC$_{50}$ values (determined as described above) for compounds according to the invention are shown in the following table. The number of the compound corresponds to the number of the Example in the experimental section.

| Example No. | EC$_{50}$ [nM] | Example No. | EC$_{50}$ [nM] | Example No. | EC$_{50}$ [nM] | Example No. | EC$_{50}$ [nM] |
|---|---|---|---|---|---|---|---|
| 90 | 149 | 99 | 1735 | 107 | 549 | 116 | 294 |
| 91 | 48 | 100 | 45 | 108 | 552 | 117 | 53 |
| 92 | 265 | 101 | 1130 | 109 | 1740 | 118 | 101 |
| 93 | 168 | 102 | 1092 | 110 | 360 | 119 | 117 |
| 94 | 10 | 103 | 1592 | 111 | 407 | 120 | 745 |
| 95 | 595 | 104 | 1948 | 112 | 1498 | 121 | 134 |
| 96 | 1632 | 105 | 53 | 113 | 47 | | |
| 97 | 170 | 106 | 885 | 115 | 54 | | |

In view of their ability to modulate the activity of the G-protein-coupled receptor GPR119, in particular an agonistic activity, the compounds of general formula I according to the invention, including the corresponding salts thereof, are theoretically suitable for the treatment of all those diseases or conditions which may be affected or which are mediated by the activation of the G-protein-coupled receptor GPR119.

Accordingly, the present invention relates to a compound of general formula I as a medicament.

Furthermore, the present invention relates to the use of a compound of general formula I or a pharmaceutical composition according to this invention for the treatment and/or prevention of diseases or conditions which are mediated by the activation of the G-protein-coupled receptor GPR119 in a patient, preferably in a human.

In yet another aspect the present invention relates to a method for treating a disease or condition mediated by the activation of the G-protein-coupled receptor GPR119 in a mammal that includes the step of administering to a patient, preferably a human, in need of such treatment a therapeutically effective amount of a compound or a pharmaceutical composition of the present invention.

Diseases and conditions mediated by agonists of the G-protein-coupled receptor GPR119 embrace metabolic diseases or conditions.

According to one aspect the compounds and pharmaceutical compositions of the present invention are particularly suitable for treating diabetes mellitus, in particular Type 2 diabetes, Type 1 diabetes, complications of diabetes (such as e.g. retinopathy, nephropathy or neuropathies, diabetic foot, ulcers or macro-angiopathies), metabolic acidosis or ketosis, reactive hypoglycaemia, hyperinsulinaemia, glucose metabolic disorder, insulin resistance, metabolic syndrome, dyslipidaemias of different origins, atherosclerosis and related diseases, obesity, high blood pressure, chronic heart failure, oedema and hyperuricaemia.

The compounds and pharmaceutical compositions of the present invention are also suitable for preventing beta-cell degeneration such as e.g. apoptosis or necrosis of pancreatic beta cells. The compounds and pharmaceutical compositions of the present invention are also suitable for improving or restoring the functionality of pancreatic cells, and also for increasing the number and size of pancreatic beta cells.

Therefore according to another aspect the invention relates to compounds of formula I and pharmaceutical compositions according to the invention for use in preventing, delaying, slowing the progression of and/or treating metabolic diseases, particularly in improving the glycaemic control and/or beta cell function in the patient.

In another aspect the invention relates to compounds of formula I and pharmacuetical compositions according to the invention for use in preventing, delaying, slowing the progression of and/or treating type 2 diabetes, overweight, obesity, complications of diabetes and associated pathological conditions.

In addition the compounds and pharmaceutical compositions according to the invention are suitable for use in one or more of the following therapeutic processes:

for preventing, delaying, slowing the progression of or treating metabolic diseases, such as for example type 1 diabetes, type 2 diabetes, insufficient glucose tolerance, insulin resistance, hyperglycaemia, hyperlipidaemia, hypercholesterolaemia, dyslipidaemia, syndrome X, metabolic syndrome, obesity, high blood pressure, chronic systemic inflammation, retinopathy, neuropathy, nephropathy, atherosclerosis, endothelial dysfunction or bone-related diseases (such as osteoporosis, rheumatoid arthritis or osteoarthritis);

for improving glycaemic control and/or reducing fasting plasma glucose, postprandial plasma glucose and/or the glycosylated haemoglobin HbA1c;

for preventing, delaying, slowing or reversing the progression of disrupted glucose tolerance, insulin resistance and/or metabolic syndrome to type 2 diabetes;

for preventing, delaying, slowing the progression of or treating a condition or a disease selected from among the complications of diabetes, such as for example retinopathy, nephropathy or neuropathies, diabetic foot, ulcers or macroangiopathies;

for reducing weight or preventing weight gain or assisting weight loss;

for preventing or treating the degradation of pancreatic beta cells and/or improving and/or restoring the functionality of pancreatic beta cells and/or restoring the functionality of pancreatic insulin secretion;

for maintaining and/or improving insulin sensitivity and/or preventing or treating hyperinsulinaemia and/or insulin resistance.

In particular, the compounds and pharmaceutical compositions according to the invention are suitable for the treatment of obesity, diabetes (comprising type 1 and type 2 diabetes, preferably type 2 diabetes mellitus) and/or complications of diabetes (such as for example retinopathy, nephropathy or neuropathies, diabetic foot, ulcers or macroangiopathies).

The compounds according to the invention are most particularly suitable for treating type 2 diabetes mellitus.

The dose range of the compounds of general formula I applicable per day is usually from 0.001 to 10 mg, for example from 0.01 to 8 mg per kg body weight of the patient. Each dosage unit may conveniently contain from 0.1 to 1000 mg, for example 0.5 to 500 mg.

The actual therapeutically effective amount or therapeutic dosage will of course depend on factors known by those skilled in the art such as age and weight of the patient, route of administration and severity of disease. In any case the compound or composition will be administered at dosages and in a manner which allows a therapeutically effective amount to be delivered based upon patient's unique condition.

The compounds, compositions, including any combinations with one or more additional therapeutic agents, according to the invention may be administered by oral, transdermal, inhalative, parenteral or sublingual route. Of the possible methods of administration, oral or intravenous administration is preferred.

Pharmaceutical Compositions

Suitable preparations for administering the compounds of formula I, optionally in combination with one or more further therapeutic agents, will be apparent to those with ordinary skill in the art and include for example tablets, pills, capsules, suppositories, lozenges, troches, solutions, syrups, elixirs, sachets, injectables, inhalatives and powders etc. Oral formulations, particularly solid forms such as e.g. tablets or capsules are preferred. The content of the pharmaceutically active compound(s) is advantageously in the range from 0.1 to 90 wt.-%, for example from 1 to 70 wt.-% of the composition as a whole.

Suitable tablets may be obtained, for example, by mixing one or more compounds according to formula I with known excipients, for example inert diluents, carriers, disintegrants, adjuvants, surfactants, binders and/or lubricants. The tablets may also consist of several layers. The particular excipients, carriers and/or diluents that are suitable for the desired preparations will be familiar to the skilled man on the basis of his specialist knowledge. The preferred ones are those that are suitable for the particular formulation and method of administration that are desired. The preparations or formulations according to the invention may be prepared using methods known per se that are familiar to the skilled man, such as for example by mixing or combining at least one compound of formula I according to the invention, or a pharmaceutically acceptable salt of such a compound, and one or more excipients, carriers and/or diluents.

Combination Therapy

The compounds of the invention may further be combined with one or more, preferably one additional therapeutic agent. According to one embodiment the additional therapeutic agent is selected from the group of therapeutic agents useful in the treatment of diseases or conditions described hereinbefore, in particular associated with metabolic diseases or conditions such as for example diabetes mellitus, obesity, diabetic complications, hypertension, hyperlipidemia. Additional therapeutic agents which are suitable for such combinations include in particular those which for example potentiate the therapeutic effect of one or more active substances with respect to one of the indications mentioned and/or which allow the dosage of one or more active substances to be reduced.

Therefore a compound of the invention may be combined with one or more additional therapeutic agents selected from the group consisting of antidiabetic agents, agents for the treatment of overweight and/or obesity and agents for the treatment of high blood pressure, heart failure and/or atherosclerosis.

Antidiabetic agents are for example metformin, sulphonylureas, nateglinide, repaglinide, thiazolidinediones, PPAR-(alpha, gamma or alpha/gamma) agonists or modulators, alpha-glucosidase inhibitors, DPPIV inhibitors, SGLT2-inhibitors, insulin and insulin analogues, GLP-1 and GLP-1 analogues or amylin and amylin analogues, cycloset, 11β-HSD1 inhibitors. Other suitable combination partners are inhibitors of protein tyrosinephosphatase 1, substances that affect deregulated glucose production in the liver, such as e.g. inhibitors of glucose-6-phosphatase, or fructose-1,6-bisphosphatase, glycogen phosphorylase, glucagon receptor antagonists and inhibitors of phosphoenol pyruvate carboxykinase, glycogen synthase kinase or pyruvate dehydrokinase, alpha2-antagonists, CCR-2 antagonists or glucokinase activators. One or more lipid lowering agents are also suitable as combination partners, such as for example HMG-CoA-reductase inhibitors, fibrates, nicotinic acid and the derivatives thereof, PPAR-(alpha, gamma or alpha/gamma) agonists or modulators, PPAR-delta agonists, ACAT inhibitors or cholesterol absorption inhibitors such as, bile acid-binding substances such as, inhibitors of ileac bile acid transport, MTP inhibitors, or HDL-raising compounds such as CETP inhibitors or ABC1 regulators.

Therapeutic agents for the treatment of overweight and/or obesity are for example antagonists of the cannabinoid1 receptor, MCH-1 receptor antagonists, MC4 receptor agonists, NPY5 or NPY2 antagonists, β3-agonists, leptin or leptin mimetics, agonists of the 5HT2c receptor.

Therapeutic agents for the treatment of high blood pressure, chronic heart failure and/or atherosclerosis are for example A-II antagonists or ACE inhibitors, ECE inhibitors, diuretics, β-blockers, Ca-antagonists, centrally acting antihypertensives, antagonists of the alpha-2-adrenergic receptor, inhibitors of neutral endopeptidase, thrombocyte aggregation inhibitors and others or combinations thereof are suitable. Angiotensin II receptor antagonists are preferably used for the treatment or prevention of high blood pressure and complications of diabetes, often combined with a diuretic such as hydrochlorothiazide.

The dosage for the combination partners mentioned above is usually 1/5 of the lowest dose normally recommended up to 1/1 of the normally recommended dose.

Preferably, compounds of the present invention and/or pharmaceutical compositions comprising a compound of the present invention optionally in combination with one or more additional therapeutic agents are administered in conjunction with exercise and/or a diet.

Therefore, in another aspect, this invention relates to the use of a compound according to the invention in combination with one or more additional therapeutic agents described hereinbefore and hereinafter for the treatment of diseases or conditions which may be affected or which are mediated by the activation of the G-protein-coupled receptor GPR119, in particular diseases or conditions as described hereinbefore and hereinafter.

In yet another aspect the present invention relates to a method for treating a disease or condition mediated by the activation of the G-protein-coupled receptor GPR119 in a patient that includes the step of administering to the patient, preferably a human, in need of such treatment a therapeutically effective amount of a compound of the present invention in combination with a therapeutically effective amount of one or more additional therapeutic agents described in hereinbefore and hereinafter, The use of the compound according to the invention in combination with the additional therapeutic agent may take place simultaneously or at staggered times.

The compound according to the invention and the one or more additional therapeutic agents may both be present together in one formulation, for example a tablet or capsule, or separately in two identical or different formulations, for example as a so-called kit-of-parts.

Consequently, in another aspect, this invention relates to a pharmaceutical composition which comprises a compound according to the invention and one or more additional therapeutic agents described hereinbefore and hereinafter, optionally together with one or more inert carriers and/or diluents.

Other features and advantages of the present invention will become apparent from the following more detailed Examples which illustrate, by way of example, the principles of the invention.

EXAMPLES

The terms "ambient temperature" and "room temperature" are used interchangeably and designate a temperature of about 20° C.

Preliminary Remarks:

As a rule, $^1$H-NMR and/or mass spectra have been obtained for the compounds prepared. The $R_f$ values are determined using Merck silica gel 60 $F_{254}$ plates and UV light at 254 nm.

Analytical HPLC and TLC parameters employed for characterization of products (TFA denotes trifluoroacetic acid):

| method 1 column | Waters XBridge C18, 3 × 30 mm, 2.5 μm<br>A: water + 0.2% TFA<br>B: methanol | | | method 2 column | Waters XBridge C18, 3 × 30 mm, 2.5 μm<br>A: water + 0.1% TFA<br>B: methanol | | |
|---|---|---|---|---|---|---|---|
| | TIME (min) | A % | B % | | TIME (min) | A % | B % |
| | 0.00 | 95 | 5 | | 0.00 | 95 | 5 |
| | 0.05 | 95 | 5 | | 0.30 | 95 | 5 |
| | 1.40 | 0 | 100 | | 1.50 | 0 | 100 |
| | 1.80 | 0 | 100 | | 1.55 | 0 | 100 |
| | | | | | 1.65 | 0 | 100 |
| flow rate | 2.2 mL/min | | | flow rate | 2.2 mL/min | | |
| wavelength | UV 220, 230, or 254 nm | | | wavelength | UV 220, 230, or 254 nm | | |
| method 3 column | Waters XBridge C18, 4.6 × 30 mm, 2.5 μm<br>A: water + 0.1% TFA<br>B: methanol + 0.1% TFA | | | method 4 column | Waters Sunfire C18, 4.6 × 30 mm, 2.5 μm<br>A: water + 0.1% TFA<br>B: methanol + 0.1% TFA | | |
| | TIME (min) | A % | B % | | TIME (min) | A % | B % |
| | 0.00 | 95 | 5 | | 0.00 | 95 | 5 |
| | 0.05 | 95 | 5 | | 0.05 | 95 | 5 |
| | 2.05 | 0 | 100 | | 2.05 | 0 | 100 |
| | 2.10 | 0 | 100 | | 2.10 | 0 | 100 |
| | 2.35 | 0 | 100 | | 2.35 | 0 | 100 |
| flow rate | 3-4 mL/min | | | flow rate | 3-4 mL/min | | |
| wavelength | UV 220, 230, or 254 nm | | | wavelength | UV 220, 230, or 254 nm | | |
| method 5 column | Waters Sunfire C18, 4.6 × 50 mm, 3.5 μm<br>A: water + 0.1% TFA<br>B: methanol | | | method 6 column | Waters X-terra MS C18 2.5 μm 4.6 mm × 30 mm<br>A: water + 0.1% HCO$_2$H<br>B: H$_3$CCN + 0.1% HCO$_2$H | | |
| | TIME (min) | A % | B % | | TIME (min) | A % | B % |
| | 0.00 | 80 | 20 | | 0.00 | 95 | 5 |
| | 1.70 | 0 | 100 | | 2.00 | 0 | 100 |
| | 2.50 | 0 | 100 | | 2.50 | 0 | 100 |
| | 2.60 | 80 | 20 | | 2.60 | 95 | 5 |

-continued

|  |  |  |  |  |  |  |  |
|---|---|---|---|---|---|---|---|
|  | 0.00 | 80 | 20 |  |  |  |  |
| flow rate | 2 mL/min |  |  | flow rate | 1.5 mL/min |  |  |
| wavelength | 210-500 nm |  |  | wavelength | 210-420 nm |  |  |

| method 7 |  |  |  | method 8 |  |  |  |
|---|---|---|---|---|---|---|---|
| column | Waters XBridge C18, 4.6 × 30 mm, 3.5 μm<br>A: water + 0.1% TFA<br>B: methanol + 0.1% TFA |  |  | column | Waters XBridge C18, 4.6 × 30 mm, 3.5 μm<br>A: water + 0.1% TFA<br>B: methanol |  |  |
|  | TIME (min) | A % | B % |  | TIME (min) | A % | B % |
|  | 0.00 | 95 | 5 |  | 0.00 | 95 | 5 |
|  | 0.20 | 95 | 5 |  | 1.60 | 0 | 100 |
|  | 1.50 | 0 | 100 |  | 1.85 | 0 | 100 |
|  | 1.75 | 0 | 100 |  | 1.90 | 95 | 5 |
|  | 1.85 | 95 | 5 |  |  |  |  |
| flow rate | 4 mL/min |  |  | flow rate | 4.8 mL/min |  |  |
| wavelength | UV 220, 230, or 254 nm |  |  | wavelength | UV 220, 230, or 254 nm |  |  |

| method 9 |  |  |  | method 10 |  |  |  |
|---|---|---|---|---|---|---|---|
| column | Waters Sunfire C18, 4.6 × 50 mm, 3.5 μm<br>A: water + 0.1% TFA<br>B: acetonitrile + 0.08% TFA |  |  | column | Waters Sunfire C18, 4.6 × 50 mm, 3.5 μm<br>A: water + 0.1% TFA<br>B: methanol |  |  |
|  | TIME (min) | A % | B % |  | TIME (min) | A % | B % |
|  | 0.00 | 95 | 5 |  | 0.00 | 95 | 5 |
|  | 2.00 | 0 | 100 |  | 2.00 | 0 | 100 |
|  | 2.50 | 0 | 100 |  | 2.50 | 0 | 100 |
|  | 2.60 | 95 | 5 |  | 2.60 | 95 | 5 |
| flow rate | 1.50 mL/min |  |  | flow rate | 2.0 mL/min |  |  |
| wavelength | 210-500 nm |  |  | wavelength | 210-500 nm |  |  |

| method 11 |  |  |  | method 12 |  |  |  |
|---|---|---|---|---|---|---|---|
| column | Waters X-terra MS C18 2.5 μm 4.6 mm × 30 mm<br>A: water + 0.1% $HCO_2H$<br>B: $H_3CCN$ + 0.1% $HCO_2H$ |  |  | column | Waters Xbridge C18 4.6 × 20 mm, 3.5 μm,<br>A: water + 0.1% TFA<br>B: methanol |  |  |
|  | TIME (min) | A % | B % |  | TIME (min) | A % | B % |
|  | 0.00 | 95 | 5 |  | 0.00 | 95 | 5 |
|  | 0.10 | 95 | 5 |  | 0.20 | 95 | 5 |
|  | 3.10 | 2 | 98 |  | 1.60 | 0 | 100 |
|  | 4.50 | 2 | 98 |  | 2.10 | 0 | 100 |
|  | 5.00 | 95 | 5 |  |  |  |  |
| flow rate | 1.0 mL/min |  |  | flow rate | 4.0 mL/min |  |  |
| wavelength | 210-420 nm |  |  | wavelength | UV 220, 230, or 254 nm |  |  |

| method 13 |  |  |  | method 14 |  |  |  |
|---|---|---|---|---|---|---|---|
| column | Waters XBridge C18, 4.6 × 30 mm, 3.5 μm<br>A: water + 0.1% TFA<br>B: methanol |  |  | column | Waters XBridge C18, 4.6 × 30 mm, 3.5 μm<br>A: water + 0.1% $HCO_2H$<br>B: methanol |  |  |
|  | TIME (min) | A % | B % |  | TIME (min) | A % | B % |
|  | 0.00 | 95 | 5 |  | 0.00 | 95 | 5 |
|  | 1.60 | 0 | 100 |  | 0.15 | 95 | 5 |
|  | 1.85 | 0 | 100 |  | 1.70 | 0 | 100 |
|  | 1.90 | 95 | 5 |  | 2.25 | 0 | 100 |
| flow rate | 4.0 mL/min |  |  | flow rate | 4.0 mL/min |  |  |
| wavelength | UV 220, 230, or 254 nm |  |  | wavelength | UV 220, 230, or 254 nm |  |  |

| method 15 |  |  |  | method 16 |  |  |  |
|---|---|---|---|---|---|---|---|
| column | Waters XBridge C18, 4.6 × 30 mm, 3.5 μm<br>A: water + 0.1% $NH_3$<br>B: methanol |  |  | column | Ascentis Express C18, 2.1 × 50 mm, 2.7 μm<br>A: water + 0.1% TFA<br>B: $CH_3CN$ + 0.08% TFA |  |  |
|  | TIME (min) | A % | B % |  | TIME (min) | A % | B % |
|  | 0.00 | 95 | 5 |  | 0.00 | 95 | 5 |
|  | 0.15 | 95 | 5 |  | 0.70 | 1 | 99 |
|  | 1.70 | 0 | 100 |  | 0.80 | 1 | 99 |
|  | 2.25 | 0 | 100 |  | 0.81 | 95 | 5 |
| flow rate | 4.0 mL/min |  |  | flow rate | 1.5 mL/min |  |  |
| wavelength | UV 220, 230, or 254 nm |  |  | wavelength | UV 220, 230, or 254 nm |  |  |

| method 17 |  |  |  | method 18 |  |  |  |
|---|---|---|---|---|---|---|---|
| column | Waters Sunfire C18_3.0 × 30 mm, 2.5 μm<br>A: methanol + 0.1% TFA<br>B: methanol |  |  | column | Waters Sunfire C18_3 × 30 mm, 2.5 μm<br>A: water + 0.1% TFA<br>B: methanol |  |  |
|  | TIME (min) | A % | B % |  | TIME (min) | A % | B % |
|  | 0.00 | 95 | 5 |  | 0.00 | 95 | 5 |
|  | 0.25 | 95 | 5 |  | 0.05 | 95 | 5 |

-continued

```
           1.70        0      100               1.40       0     100
           1.75        0      100               1.80       0     100
           1.90        0      100
flow rate  1.8-2.5 mL/min               flow rate  2.2 mL/min
wavelength UV 220, 230, or 254 nm       wavelength UV 220, 230, or 254 nm method 19  Phenomenex Gemini NX C18,
column     5 µm, 110 A, 3.0 × 100 mm
           A: water + 0.04% NH4OH
           B: acetonitrile + 0.04% NH4OH
              TIME (min)    A %    B %

0.00          95      5
              5.20           5     95
           linear gradient from 0 to 5.2 min
flow rate  2.0 mL/min
wavelength UV 220, 230, or 254 nm
```

Intermediate 1

N-Cyclopropyl-4-oxazol-5-yl-N-piperidin-4-yl-benzamide

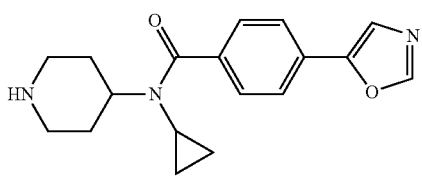 [SMILES: O=C(c1ccc(-c2cnco2)cc1)N(C1CCNCC1)C1CC1]

2-(1H-Benzotriazol-1-yl)-1,1,3,3-tetramethyluronium tetrafluoroborate (6.10 g) is added to a solution of 4-oxazol-5-yl-benzoic acid (3.00 g) and ethyldiisopropylamine (5.56 mL) in N,N-dimethylformamide (50 mL) at room temperature. The solution is stirred for 10 min prior to the addition of 4-cyclopropylamino-piperidine-1-carboxylic acid tert-butyl ester (4.57 g). The resulting mixture is kept at room temperature over night. The mixture is treated with activated charcoal and filtered through a pad of basic aluminum oxide. The pad is washed with N,N-dimethylformamide/methanol (9:1) and the combined filtrates are concentrated in vacuo. The residue is dissolved in 1,4-dioxane (35 mL), a 4 M solution of hydrogen chloride in 1,4-dioxane (20 mL) is added and the resulting mixture is stirred at room temperature for 2 h. The solvent is evaporated and the residue is taken up in water. The resulting mixture is washed with dichloromethane, basified with NaOH solution and extracted with dichloromethane. The combined extracts are dried over $Na_2SO_4$ and concentrated in vacuo. The residue is triturated with diethyl ether to afford the title compound. LC (method 1): $t_R$=0.70 min; Mass spectrum (ESI$^+$): m/z=312 [M+H]$^+$.

Intermediate 2

N-(1-Cyano-piperidin-4-yl)-N-cyclopropyl-4-oxazol-5-yl-benzamide

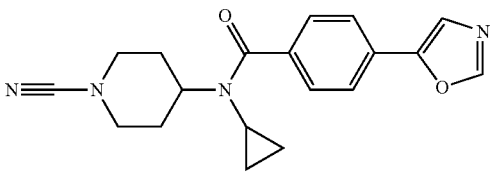 [SMILES: N#CN1CCC(N(C(=O)c2ccc(-c3cnco3)cc2)C2CC2)CC1]

Bromonitirile (1.96 g) is added to a solution of N-cyclopropyl-4-oxazol-5-yl-N-piperidin-4-yl-benzamide (3.50 g) and ethyldiisopropylamine (9.60 mL) in dichloromethane (125 mL) and tetrahydrofuran (125 mL) and the reaction mixture is stirred over night at room temperature. The reaction mixture is washed with water and the organic phase is dried over $Na_2SO_4$ and concentrated in vacuo. The residue is triturated with diethyl ether to afford the title compound. LC (method 3): $t_R$=1.55 min; Mass spectrum (ESI$^+$): m/z=337 [M+H]$^+$.

Intermediate 3

N-Hydroxy-but-3-enamidine

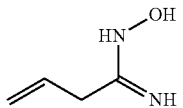

But-3-enenitrile (500 mg) is heated under reflux in a 2 M solution of hydroxylamine in methanol (4.10 mL) for 5 h. The reaction mixture is cooled to room temperature over night and concentrated in vacuo. The residue is taken up in diethyl ether and filtered. The solvent is evaporated to afford the title compound, which is used for the next reaction step without further purification. Mass spectrum (ESI$^+$): m/z=101 [M+H]$^+$.

Intermediate 4

1,4-Dioxa-8-aza-spiro[4.5]decane-8-carbonitrile

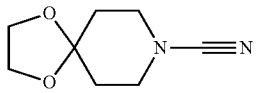

The title compound is prepared from 1,4-dioxa-8-aza-spiro[4.5]decane and bromonitrile following a procedure analogous to that described in Intermediate 2. TLC: $r_f$=0.80 (aluminum oxide, ethyl acetate/petrol ether 3:1); Mass spectrum (ESI$^+$): m/z=169 [M+H]$^+$.

Intermediate 5

8-(3-Phenyl-[1,2,4]oxadiazol-5-yl)-1,4-dioxa-8-aza-spiro[4.5]decane

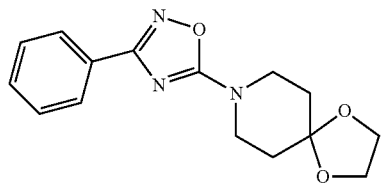 [SMILES: c1ccc(-c2noc(N3CCC4(CC3)OCCO4)n2)cc1]

A 0.5 M solution of zinc chloride in tetrahydrofuran (18.00 mL) is added dropwise at room temperature to a mixture of N-hydroxy-benzamidine (817 mg) and 1,4-dioxa-8-aza-spiro[4.5]decane-8-carbonitrile (1.00 g) in ethyl acetate (20 mL). The reaction mixture is stirred at 50° C. for 3 h and cooled to room temperature. The precipitate is filtered off and heated to 100° C. for 1 h in a mixture of ethanol (10 mL) and glacial acetic acid (5 mL). The solvents are evaporated and the crude product is purified by HPLC. TLC: $r_f$=0.88 (silica gel, CH$_2$Cl$_2$/MeOH 9:1); Mass spectrum (ESI$^+$): m/z=288 [M+H]$^+$.

Intermediate 6

1-(3-Phenyl-[1,2,4]oxadiazol-5-yl)-piperidin-4-one

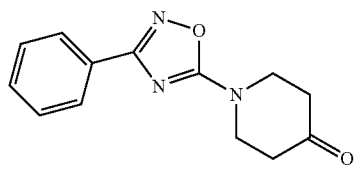 [SMILES: O=C1CCN(c2nc(-c3ccccc3)no2)CC1]

A mixture of 8-(3-phenyl-[1,2,4]oxadiazol-5-yl)-1,4-dioxa-8-aza-spiro[4.5]decane (660 mg), conc. aqueous HCl (5 mL) and water (5 mL) is kept at room temperature overnight. The mixture is basified with conc. aqueous ammonia and the precipitate is filtered off and dissolved in dichloromethane. The resulting solution is dried over Na$_2$SO$_4$ and concentrated in vacuo to give the title compound. TLC: $r_f$=0.33 (silica gel, hexane/ethyl acetate 2:1); Mass spectrum (ESI$^+$): m/z=244 [M+H]$^+$.

Intermediate 7

Cyclopropyl-[1-(3-phenyl-[1,2,4]oxadiazol-5-yl)-piperidin-4-yl]-amine

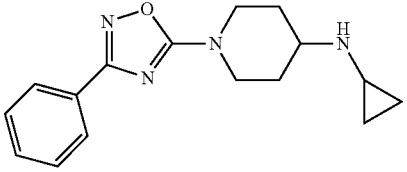 [SMILES: c1ccc(-c2noc(N3CCC(NC4CC4)CC3)n2)cc1]

A mixture of 1-(3-phenyl-[1,2,4]oxadiazol-5-yl)-piperidin-4-one (400 mg), cyclopropylamine (120 µL), sodium triacetoxyborohydride (420 mg) and glacial acetic acid (0.20 mL) in dichloromethane (7 mL) is stirred for two days at room temperature. Dichloromethane is added and the mixture is washed with aqueous K$_2$CO$_3$ solution. The organic phase is dried over Na$_2$SO$_4$ and concentrated in vacuo to afford the title compound. TLC: $r_f$=0.30 (silica gel, CH$_2$Cl$_2$/MeOH 95:5); Mass spectrum (ESI$^+$): m/z=285 [M+H]$^+$.

Intermediate 8

4-[Cyclopropyl-(4-iodo-benzoyl)-amino]-piperidine-1-carboxylic acid tert-butyl ester

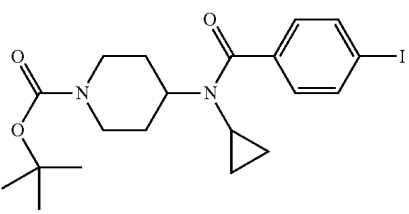 [SMILES: CC(C)(C)OC(=O)N1CCC(N(C(=O)c2ccc(I)cc2)C2CC2)CC1]

2-(1H-Benzotriazol-1-yl)-1,1,3,3-tetramethyluronium tetrafluoroborate (2.67 g) is added to a solution of 4-iodo-benzoic acid (2.06 g) and ethyldiisopropylamine (2.88 mL) in N,N-dimethylformamide (15 mL) at room temperature. The solution is stirred for 10 min prior to the addition of 4-cyclopropylamino-piperidine-1-carboxylic acid tert-butyl ester (2.00 g). The resulting mixture stirred at room temperature overnight. The mixture is concentrated in vacuo and the residue is mixed with water and ethyl acetate. The organic phase is separated, washed with water and aqueous NaHCO$_3$ solution, dried, and the solvent is evaporated. The crude product is used for the next reaction step without further purification. LC (method 5): $t_R$=2.32 min; Mass spectrum (ESI$^+$): m/z=471 [M+H]$^+$.

Intermediate 9

Biphenyl-4,4'-dicarboxylic acid 4-amide 4'-(cyclopropyl-piperidin-4-yl-amide)

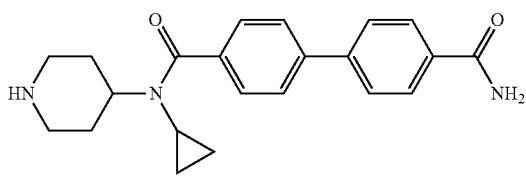 [SMILES: NC(=O)c1ccc(-c2ccc(C(=O)N(C3CCNCC3)C3CC3)cc2)cc1]

Aqueous Na$_2$CO$_3$ solution (532 μL) and Pd(PPh$_3$)$_2$Cl$_2$ (69 mg) are added to a mixture of 4-[cyclopropyl-(4-iodo-benzoyl)-amino]-piperidine-1-carboxylic acid tert-butyl ester (250 mg) and 4-aminocarbonylphenylboronic acid (263 mg) in 1,4-dioxane (10 mL) and methanol (5 mL) under an argon atmosphere. The reaction mixture is stirred overnight at 80° C. After cooling to room temperature, the solvents are evaporated and the residue is mixed with dichloromethane and water. The aqueous phase is extracted with dichloromethane and the combined organic phases are dried and concentrated in vacuo. The crude product is dissolved in dichloromethane and trifluoroacetic acid is added. The mixture is stirred for 1 h at room temperature and concentrated in vacuo. The crude product is purified by HPLC (MeOH/H$_2$O/TFA) to give the title compound as trifluoroacetic acid salt. LC (method 4): $t_R$=1.19 min; Mass spectrum (ESI$^+$): m/z=364 [M+H]$^+$.

Intermediate 10

Biphenyl-4,4'-dicarboxylic acid 4-amide 4'-[(1-cyano-piperidin-4-yl)-cyclopropyl-amide]

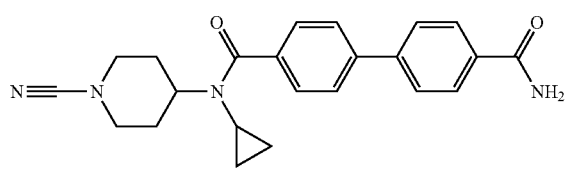 [SMILES: N#CN1CCC(N(C(=O)c2ccc(-c3ccc(C(N)=O)cc3)cc2)C2CC2)CC1]

The title compound is prepared from biphenyl-4,4'-dicarboxylic acid 4-amide 4'-(cyclopropyl-piperidin-4-yl-amide) and bromonitrile following a procedure analogous to that described in Intermediate 2. LC (method 4): $t_R$=1.65 min; Mass spectrum (ESI$^+$): m/z=389 [M+H]$^+$.

Intermediate 11

4-(4-Methyl-oxazol-5-yl)-benzoic acid methyl ester

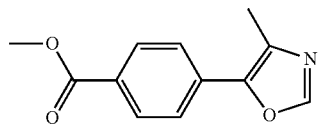 [SMILES: COC(=O)c1ccc(-c2ocnc2C)cc1]

A mixture of 4-formyl-benzoic acid methyl ester (2.50 g), 1-(1-isocyano-ethanesulfonyl)-4-methyl-benzene (3.19 g), and potassium carbonate (2.76 g) in methanol (50 mL) is heated to reflux for 2 h. After cooling to room temperature, the mixture is poured onto water and extracted with dichloromethane. The organic phase is washed with water, dried over Na$_2$SO$_4$ and concentrated in vacuo. The residue is chromatographed on silica gel (dichloromethane/methanol 40:1) to afford the title compound. LC (method 6): $t_R$=2.68 min; Mass spectrum (ESI$^+$): m/z=218 [M+H]$^+$.

Intermediate 12

4-(4-Methyl-oxazol-5-yl)-benzoic acid

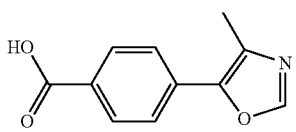

A mixture of 4-(4-methyl-oxazol-5-yl)-benzoic acid methyl ester (1.50 g), 1 M aqueous NaOH solution (7.00 mL) and methanol (20 mL) is kept at room temperature overnight. The precipitate is filtered off, dissolved in water and neutralized with 4 M HCl. The precipitate is filtered off, dissolved in dichloromethane and a small amount of methanol, and the solution is dried over Na$_2$SO$_4$ and concentrated in vacuo. The residue is triturated with diethylether to afford the title compound. Mass spectrum (ESI$^+$): m/z=204 [M+H]$^+$.

Intermediate 13

4-(4-Methyl-oxazol-5-yl)-benzoyl chloride

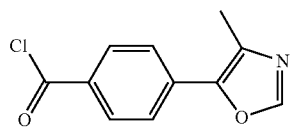

Thionyl chloride (2.00 mL) is added to 4-(4-methyl-oxazol-5-yl)-benzoic acid (400 mg) in dichloromethane (5 mL) and the mixture is stirred for two days at room temperature. The solvent is evaporated to give the title compound, which is used without further purification for the next reaction step.

Intermediate 14

1-(3-Isopropyl-[1,2,4]oxadiazol-5-yl)-piperidin-4-one

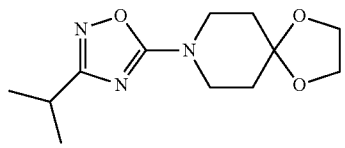 [SMILES: CC(C)c1noc(N2CCC3(CC2)OCCO3)n1]

The title compound is prepared from 1,4-dioxa-8-aza-spiro[4.5]decane-8-carbonitrile and N-hydroxy-isobutyramidine following a procedure analogous to that described in Intermediate 5. LC (method 6): $t_R$=1.56 min; Mass spectrum (ESI$^+$): m/z=254 [M+H]$^+$.

Intermediate 15

1-(3-Isopropyl-[1,2,4]oxadiazol-5-yl)-piperidin-4-one

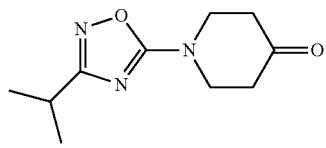

The title compound is prepared from 8-(3-isopropyl-[1,2,4]oxadiazol-5-yl)-1,4-dioxa-8-aza-spiro[4.5]decane following a procedure analogous to that described in Intermediate 6. Mass spectrum (ESI$^+$): m/z=210 [M+H]$^+$.

Intermediate 16

Cyclopropyl-[1-(3-isopropyl-[1,2,4]oxadiazol-5-yl)-piperidin-4-yl]-amine

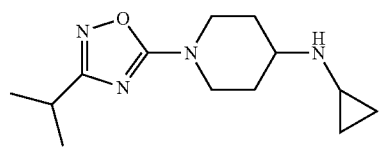 [SMILES: CC(C)c1noc(N2CCC(NC3CC3)CC2)n1]

The title compound is prepared from 1-(3-isopropyl-[1,2,4]oxadiazol-5-yl)-piperidin-4-one and cyclopropylamine following a procedure analogous to that described in Intermediate 7. Mass spectrum (ESI$^+$): m/z=251 [M+H]$^+$.

Intermediate 17

4-{Cyclopropyl-[4-(4-methyl-oxazol-5-yl)-benzoyl]-amino}-piperidine-1-carboxylic acid tert-butyl ester

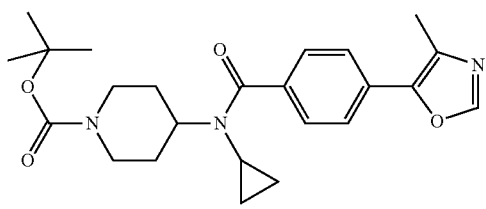 [SMILES: Cc1ncoc1-c1ccc(C(=O)N(C2CC2)C2CCN(C(=O)OC(C)(C)C)CC2)cc1]

4-(4-Methyl-oxazol-5-yl)-benzoyl chloride (340 mg) is added portionwise to a mixture of 4-cyclopropylamino-piperidine-1-carboxylic acid tert-butyl ester (369 mg) and ethyldiisopropylamine (274 µL) in dichloromethane (10 mL). The mixture is stirred for 1 h at room temperature, washed with water, aqueous citric acid solution and 0.5 M NaOH, dried over Na$_2$SO$_4$ and concentrated in vacuo. The residue is chromatographed on silica gel (dichloromethane/methanol 50:1) to afford the title compound. Mass spectrum (ESI$^+$): m/z=426 [M+H]$^+$.

Intermediate 18

N-Cyclopropyl-4-(4-methyl-oxazol-5-yl)-N-piperidin-4-yl-benzamide

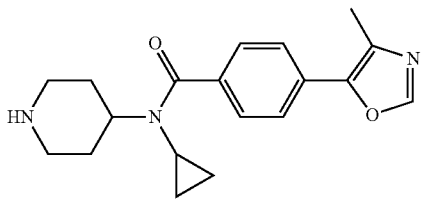 [SMILES: Cc1ncoc1-c1ccc(C(=O)N(C2CCNCC2)C2CC2)cc1]

A mixture of 4-{cyclopropyl-[4-(4-methyl-oxazol-5-yl)-benzoyl]-amino}-piperidine-1-carboxylic acid tert-butyl ester (180 mg) and trifluoroacetic acid (20% in dichloromethane) is stirred for 1 h at room temperature. The solvent is evaporated to give the title compound as its trifluoroacetic acid salt. Mass spectrum (ESI$^+$): m/z=326 [M+H]$^+$.

Intermediate 19

N-Cyclopropyl-N-[1-(N-hydroxycarbamimidoyl)-piperidin-4-yl]-4-oxazol-5-yl-benzamide

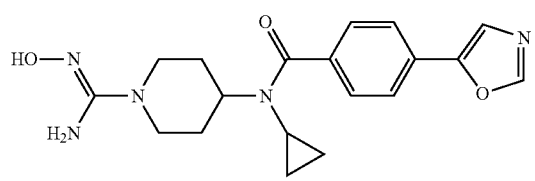 [SMILES: N/C(=N\O)N1CCC(N(C(=O)c2ccc(-c3cnco3)cc2)C2CC2)CC1]

A mixture of N-(1-cyano-piperidin-4-yl)-N-cyclopropyl-4-oxazol-5-yl-benzamide (200 mg), hydroxylamine hydrochloride (70 mg), and potassium carbonate (82 mg) in ethanol (0.70 mL) and water (1.00 mL) is heated under reflux for 5 h. The reaction mixture is cooled to room temperature, stirred at this temperature for two days and concentrated in vacuo. The residue is mixed with water and ethyl acetate and the organic phase is separated, dried and concentrated in vacuo. The crude product is purified by HPLC (MeOH/H$_2$O/TFA). LC (method 3): t$_R$=1.35 min; Mass spectrum (ESI$^+$): m/z=370 [M+H]$^+$.

Intermediate 20

4-Cyclopropylamino-3-methyl-piperidine-1-carboxylic acid tert-butyl ester

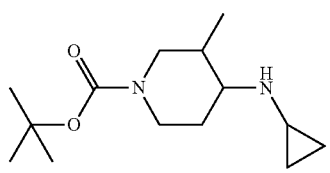 [SMILES: CC1CN(C(=O)OC(C)(C)C)CCC1NC1CC1]

The title compound is prepared from 3-methyl-4-oxo-piperidine-1-carboxylic acid tert-butyl ester and cyclopropylamine following a procedure analogous to that described in Intermediate 7. LC (method 3): $t_R$=1.30 min; Mass spectrum (ESI$^+$): m/z=255 [M+H]$^+$.

Intermediate 21

N-Cyclopropyl-N-(3-methyl-piperidin-4-yl)-4-ox-azol-5-yl-benzamide

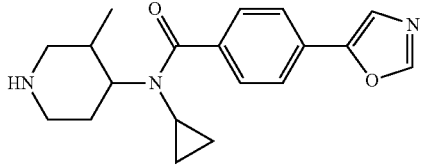

The title compound is prepared from 4-cyclopropylamino-3-methyl-piperidine-1-carboxylic acid tert-butyl ester and 4-oxazol-5-yl-benzoic acid following a procedure analogous to that described in Intermediate 1. LC (method 2): $t_R$=0.84 min; Mass spectrum (ESI$^+$): m/z=326 [M+H]$^+$.

Intermediate 22

N-Hydroxy-2-(tetrahydro-pyran-4-yl)-acetamidine

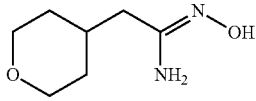 [SMILES: N/C(CC1CCOCC1)=N\O]

The title compound is prepared from (tetrahydro-pyran-4-yl)-acetonitrile following a procedure analogous to that described in Intermediate 3. LC (method 1): $t_R$=0.15 min; Mass spectrum (ESI$^+$): m/z=159 [M+H]$^+$.

Intermediate 23

N-Hydroxy-tetrahydro-pyran-4-carboxamidine

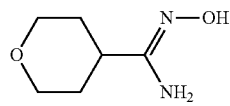

The title compound is prepared from tetrahydro-pyran-4-carbonitrile following a procedure analogous to that described in Intermediate 3. LC (method 1): $t_R$=0.13 min; Mass spectrum (ESI$^+$): m/z=145 [M+H]$^+$.

Intermediate 24

N-Hydroxy-pent-4-enamidine

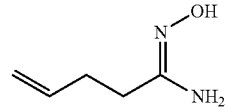

The title compound is prepared from pent-4-enenitrile following a procedure analogous to that described in Intermediate 3. Mass spectrum (ESI$^+$): m/z=115 [M+H]$^+$.

Intermediate 25

3,N-Dihydroxy-2,2-dimethyl-propionamidine

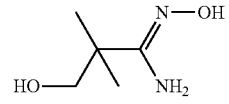

The title compound is prepared from 3-hydroxy-2,2-dimethyl-propionitrile following a procedure analogous to that described in Intermediate 3. LC (method 7): $t_R$=0.12 min; Mass spectrum (ESI$^+$): m/z=133 [M+H]$^+$.

Intermediate 26

4,4,4-Trifluoro-N-hydroxy-butyramidine

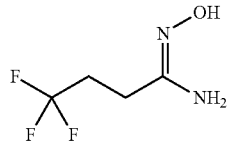

The title compound is prepared from 4,4,4-trifluoro-butyronitrile following a procedure analogous to that described in Intermediate 3. Mass spectrum (ESI$^+$): m/z=157 [M+H]$^+$.

Intermediate 27

3-Fluoro-4-oxazol-5-yl-benzoic acid

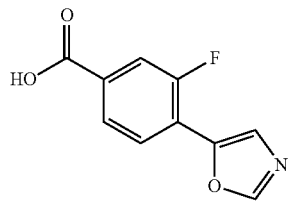 [SMILES: O=C(O)c1ccc(-c2cnco2)c(F)c1]

A mixture of 4-bromo-3-fluoro-benzoic acid (1.00 g), 5-(4,4,5,5-tetramethyl-[1,3,2]dioxaborolan-2-yl)-2-triisopropyl-silanyl-oxazole (1.90 g), PdCl$_2$ [1,1'-bis(diphenylphos-phino)-ferrocene]*CH$_2$Cl$_2$ complex (400 mg), and aqueous Na₂CO₃ solution (2 M; 5.70 mL) in N,N-dimethylformamide (6 mL) is stirred overnight at 80° C. under an argon atmosphere. After cooling to room temperature the reaction mixture is concentrated in vacuo and water is added. The resulting mixture is acidified with hydrochloric acid (4 M; 6 mL) and extracted with ethyl acetate. The combined extracts are washed with brine, dried over MgSO₄ and concentrated in vacuo. The residue is triturated with diethyl ether, filtered off and dried to give the title product. LC (method 1): $t_R$=0.87 min; Mass spectrum (ESI⁺): m/z=208 [M+H]⁺.

Intermediate 28

N-Cyclopropyl-3-fluoro-4-oxazol-5-yl-N-piperidin-4-yl-benzamide

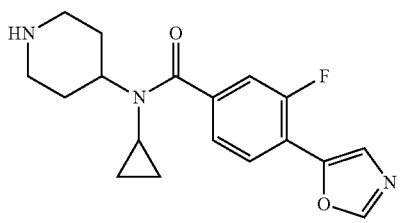 [SMILES: O=C(c1ccc(-c2cnco2)c(F)c1)N(C1CCNCC1)C1CC1]

The title compound is prepared from 4-cyclopropylamino-piperidine-1-carboxylic acid tert-butyl ester and 3-fluoro-4-oxazol-5-yl-benzoic acid following a procedure analogous to that described in Intermediate 1. The cleavage of the BOC group is accomplished by using trifluoroacetic acid in dichloromethane. LC (method 14): $t_R$=0.98 min; Mass spectrum (ESI⁺): m/z=330 [M+H]⁺.

Intermediate 29

1-(3-Propyl-[1,2,4]oxadiazol-5-yl)-piperidin-4-one

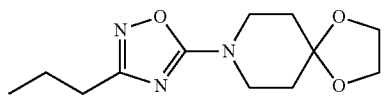

The title compound is prepared from 1,4-dioxa-8-aza-spiro [4.5]decane-8-carbonitrile and N-hydroxy-butyramidine following a procedure analogous to that described in Intermediate 5. LC (method 13): $t_R$=1.16 min; Mass spectrum (ESI⁺): m/z=254 [M+H]⁺.

Intermediate 30

1-(3-Propyl-[1,2,4]oxadiazol-5-yl)-piperidin-4-one

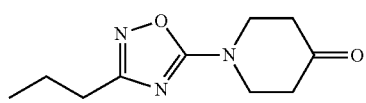

The title compound is prepared from 8-(3-propyl-[1,2,4] oxadiazol-5-yl)-1,4-dioxa-8-aza-spiro[4.5]decane following a procedure analogous to that described in Intermediate 6. LC (method 13): $t_R$=0.96 min; Mass spectrum (ESI⁺): m/z=210 [M+H]⁺.

Intermediate 31

Cyclopropyl-[1-(3-propyl-[1,2,4]oxadiazol-5-yl)-piperidin-4-yl]-amine

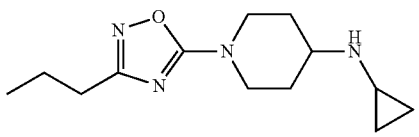 [SMILES: CCCc1noc(N2CCC(NC3CC3)CC2)n1]

The title compound is prepared as its hydrochloride salt from 1-(3-propyl-[1,2,4]oxadiazol-5-yl)-piperidin-4-one and cyclopropylamine following a procedure analogous to that described in Intermediate 7. LC (method 13): $t_R$=0.79 min; Mass spectrum (ESI⁺): m/z=251 [M+H]⁺.

Intermediate 32

1-(5-Methyl-pyrazin-2-yl)-piperidin-4-one

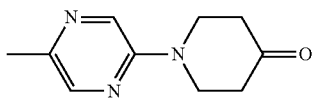

A mixture of 1-(5-methyl-pyrazin-2-yl)-piperidin-4-ol (500 mg) and Dess-Martin periodinane (1.30 g) in dichloromethane (20 mL) is stirred at room temperature for 4 h. Aqueous Na₂S₂O₃ solution and NaHCO₃ solution are added and the organic phase is separated, washed with brine, dried over MgSO₄ and concentrated in vacuo. The residue is triturated with a small amount of methanol. The mixture is filtered and the filtrate is concentrated in vacuo to give the title compound. LC (method 1): $t_R$=0.56 min; Mass spectrum (ESI⁺): m/z=192 [M+H]⁺.

Intermediate 33

Cyclopropyl-[1-(5-methyl-pyrazin-2-yl)-piperidin-4-yl]amine

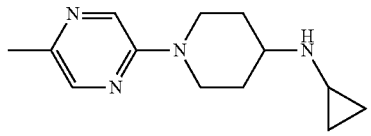 [SMILES: Cc1cnc(N2CCC(NC3CC3)CC2)cn1]

The title compound is prepared from 1-(5-methyl-pyrazin-2-yl)-piperidin-4-one and cyclopropylamine following a procedure analogous to that described in Intermediate 7. LC (method 1): $t_R$=0.68 min; Mass spectrum (ESI⁺): m/z=233 [M+H]⁺.

Intermediate 34

8-(3-tert-Butyl-[1,2,4]oxadiazol-5-yl)-1,4-dioxa-8-aza-spiro[4.5]decane

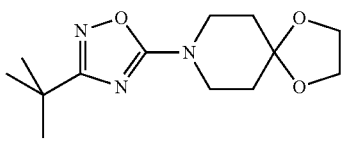 [SMILES: CC(C)(C)c1noc(N2CCC3(CC2)OCCO3)n1]

The title compound is prepared from 1,4-dioxa-8-aza-spiro[4.5]decane-8-carbonitrile and N-Hydroxy-2,2-dimethyl-propionamidine following a procedure analogous to that described in Intermediate 5. LC (method 14): $t_R$=1.53 min; Mass spectrum (ESI$^+$): m/z=268 [M+H]$^+$.

Intermediate 35

1-(3-tert-Butyl-[1,2,4]oxadiazol-5-yl)-piperidin-4-one

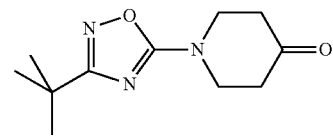 [SMILES: CC(C)(C)c1noc(N2CCC(=O)CC2)n1]

The title compound is prepared from 8-(3-tert-butyl-[1,2,4]oxadiazol-5-yl)-1,4-dioxa-8-aza-spiro[4.5]decane following a procedure analogous to that described in Intermediate 6. LC (method 14): $t_R$=1.31 min; Mass spectrum (ESI$^+$): m/z=224 [M+H]$^+$.

Intermediate 36

[1-(3-tert-Butyl-[1,2,4]oxadiazol-5-yl)-piperidin-4-yl]-cyclopropyl-amine

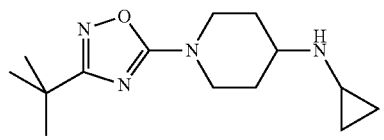 [SMILES: CC(C)(C)c1noc(N2CCC(NC3CC3)CC2)n1]

The title compound is prepared as its hydrochloride salt from 1-(3-propyl-[1,2,4]oxadiazol-5-yl)-piperidin-4-one and cyclopropylamine following a procedure analogous to that described in Intermediate 7. LC (method 14): $t_R$=0.95 min; Mass spectrum (ESI$^+$): m/z=265 [M+H]$^+$.

Intermediate 37

1-(5-Ethyl-pyrazin-2-yl)-piperidin-4-ol

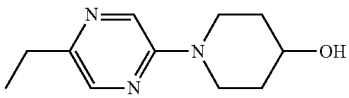

A mixture of 2-bromo-5-ethyl-pyrazine (1.66 g) and 4-hydroxy-piperidine (2.24 g) in isopropanol (15 mL) is heated to 150° C. overnight in an autoclave. After cooling to room temperature the solvent is evaporated in vacuo and water and dichloromethane are added. The aqueous phase is extracted with dichloromethane and the combined organic phases are washed with brine, dried over MgSO$_4$ and concentrated in vacuo to give the title compound. LC (method 1): $t_R$=0.66 min; Mass spectrum (ESI$^+$): m/z=208 [M+H]$^+$.

Intermediate 38

1-(5-Ethyl-pyrazin-2-yl)-piperidin-4-one

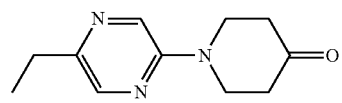

The title compound is prepared from 1-(5-ethyl-pyrazin-2-yl)-piperidin-4-ol following a procedure analogous to that described in Intermediate 32. LC (method 1): $t_R$=0.73 min; Mass spectrum (ESI$^+$): m/z=206 [M+H]$^+$.

Intermediate 39

Cyclopropyl-[1-(5-ethyl-pyrazin-2-yl)-piperidin-4-yl]amine

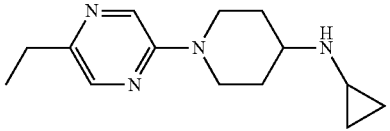 [SMILES: CCc1cnc(N2CCC(NC3CC3)CC2)cn1]

The title compound is prepared from 1-(5-ethyl-pyrazin-2-yl)-piperidin-4-one and cyclopropylamine following a procedure analogous to that described in Intermediate 7. LC (method 1): $t_R$=0.65 min; Mass spectrum (ESI$^+$): m/z=247 [M+H]$^+$.

Intermediate 40

5-(4-Bromo-2,6-difluoro-phenyl)-oxazole

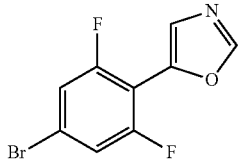 [SMILES: Fc1cc(Br)cc(F)c1-c1cnco1]

The title compound is prepared from 5-bromo-1,3-difluoro-2-iodo-benzene and 5-(4,4,5,5-tetramethyl-[1,3,2]dioxaborolan-2-yl)-2-triisopropylsilanyl-oxazole following a procedure analogous to that described in Intermediate 27. LC (method 1): $t_R$=1.18 min; Mass spectrum (ESI$^+$): m/z=260 [M+H]$^+$.

Intermediate 41

3,5-Difluoro-4-oxazol-5-yl-benzoic acid methyl ester

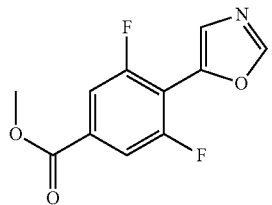 [SMILES: COC(=O)c1cc(F)c(-c2cnco2)c(F)c1]

A mixture of 5-(4-bromo-2,6-difluoro-phenyl)-oxazole (280 mg), 1,1'-bis-(diphenylphosphino)-ferrocene (60 mg), palladium acetate (24 mg), and triethylamine (225 µL) in methanol (4 mL) and N,N-dimethylformamide (3 mL) is reacted with carbon monoxide in an autoclave at 70° C. overnight. After cooling to room temperature the catalyst is filtered off and the filtrate is concentrated in vacuo. The residue is dissolved in ethyl acetate, washed with hydrochloric acid (1 M), water, and brine, dried over MgSO$_4$, and concentrated in vacuo. The crude product is used for the next step without further purification. LC (method 1): $t_R$=1.07 min; Mass spectrum (ESI$^+$): m/z=240 [M+H]$^+$.

Intermediate 42

3,5-Difluoro-4-oxazol-5-yl-benzoic acid

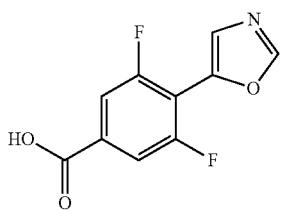 [SMILES: O=C(O)c1cc(F)c(-c2cnco2)c(F)c1]

The title compound is prepared from 3,5-difluoro-4-oxazol-5-yl-benzoic acid methyl ester following a procedure analogous to that described in Intermediate 12. LC (method 1): $t_R$=0.90 min; Mass spectrum (ESI$^+$): m/z=226 [M+H]$^+$.

Intermediate 43

1-(5-Methyl-pyrimidin-2-yl)-piperidin-4-ol

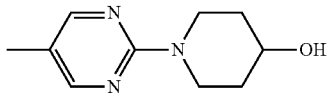

The title compound is prepared from 2-chloro-5-methyl-pyrimidine and 4-hydroxy-piperidine following a procedure analogous to that described in Intermediate 37. LC (method 1): $t_R$=0.48 min; Mass spectrum (ESI$^+$): m/z=194 [M+H]$^+$.

Intermediate 44

1-(5-Methyl-pyrimidin-2-yl)-piperidin-4-one

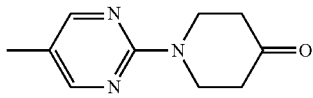

The title compound is prepared from 1-(5-methyl-pyrimidin-2-yl)-piperidin-4-ol following a procedure analogous to that described in Intermediate 32. LC (method 1): $t_R$=0.54 min; Mass spectrum (ESI$^+$): m/z=192 [M+H]$^+$.

Intermediate 45

Cyclopropyl-[1-(5-methyl-pyrimidin-2-yl)-piperidin-4-yl]amine

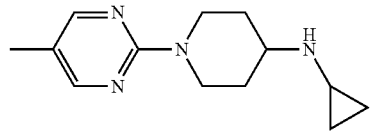 [SMILES: Cc1cnc(N2CCC(NC3CC3)CC2)nc1]

The title compound is prepared from 1-(5-methyl-pyrimidin-2-yl)-piperidin-4-one and cyclopropylamine following a procedure analogous to that described in Intermediate 7. LC (method 1): $t_R$=0.55 min; Mass spectrum (ESI$^+$): m/z=233 [M+H]$^+$.

Intermediate 46

4-(2-Methyl-imidazol-1-yl)-benzoic acid

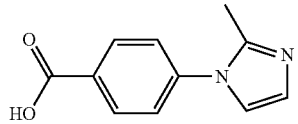

To a solution of ethyl 4-fluorobenzoate (1.68 g) in N-methyl-pyrrolidinone (10 mL) is added 2-methyl-imidazole (2.85 g) and K$_2$CO$_3$ (1.5 g) and the mixture is heated at 190°

C. in a microwave oven for 30 min. After cooling to room temperature, water and ethyl acetate are added and the organic layer is washed with water, dried (MgSO$_4$) and concentrated. Purification by chromatography on silica gel (methanol/dichloromethane 0:1→1:9) yields the ester. The ester is dissolved in methanol (50 mL) and 4 M aqueous NaOH solution (3 mL) is added. The mixture is stirred at room temperature for 1 h. The mixture is neutralized with 6 M aqueous HCl, concentrated, and then acidified to pH 2 with 6 M aqueous HCl. The precipitate is filtered off, washed with a small amount of water and dried by suction to give the acid.

Intermediate 47

4-(1H-1,2,4-triazol-1-yl)-benzoic acid

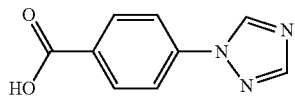 [SMILES: O=C(O)c1ccc(-n2cncn2)cc1]

To a solution of ethyl 4-fluoro-benzoate (1.68 g) in N-methyl-pyrrolidinone (10 mL) is added 1,2,4-triazole (2.5 g) and K$_2$CO$_3$ (1.5 g) and the mixture is heated at 190° C. in a microwave oven for 30 min. After cooling to room temperature, the mixture is acidified with 2 M aqueous HCl and the precipitate is filtered off, washed with a small amount of water and methanol/dichloromethane and dried by suction to give the acid.

Intermediate 48

4-(5-Methyl-1H-1,2,4-triazol-1-yl)-benzoic acid

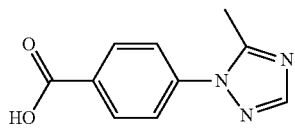

A mixture of 4-cyano-phenyl-hydrazine (1.5 g) and N-[(dimethylamino)methylene]-acetamide [made from acetamide and N,N-dimethylformamide dimethylacetal by procedure in US2007/0111984A1; (1.0 g)], and acetic acid (3 mL) is heated in a microwave oven at 90° C. for 30 min. After cooling and concentrating, the residue is purified by chromatography on silica gel (ethyl acetate/hexane 0:1→1:0) to give the ester. The ester is dissolved in methanol (30 mL) and 4 M aqueous NaOH solution (5 mL) is added and the solution is heated at 65° C. for 20 h. The mixture is neutralized with 6 M aqueous HCl, concentrated, and then acidified to pH 2 with 6 M aqueous HCl. The precipitate is filtered off washing with water and dried by suction to give the title compound.

Intermediate 49

3-Fluoro-4-(5-methyl-1H-1,2,4-triazol-1-yl)-benzoic acid

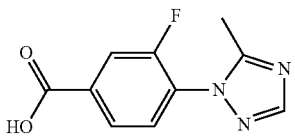 [SMILES: Cc1ncnn1-c1ccc(C(=O)O)cc1F]

3,4-Difluorobenzonitrile (1.5 g) is combined with hydrazine (8 mL) at room temperature. A strongly exothermic reaction occurs as the nitrile slowly dissolves. After ca. 30 min a white solid forms and the reaction is complete. The solid product is filtered off washing with water and dried by suction to give the hydrazine as a solid. The hydrazine is dissolved in acetic acid (6 mL) and N-[(dimethylamino)methylene]-acetamide [made from acetamide and N,N-dimethylformamide dimethylacetal by procedure in US2007/0111984A1; (1.0 g)] is added and the solution is heated in a microwave oven at 90° C. for 30 min. After cooling and concentrating, the residue is purified by chromatography on silica gel (ethyl acetate/hexane 0:1→1:0) to give the triazole. The triazole is dissolved in methanol (10 mL) and 4 M aqueous NaOH solution (2 mL) is added and the solution is heated at 65° C. for 16 h. The mixture is neutralized with 6 M aqueous HCl, concentrated, and then acidified to pH 2 with 6 M aqueous HCl. The precipitate is filtered off washing with water and dried by suction to give the title compound.

Intermediate 50

3-Fluoro-4-(1H-1,2,4-triazol-1-yl)-benzoic acid

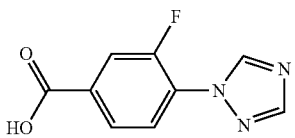 [SMILES: O=C(O)c1ccc(-n2cncn2)c(F)c1]

To a solution of ethyl 3,4-difluoro-benzoate (1.5 g) in N,N-dimethylformamide (15 mL) is added 1,2,4-triazole (1.1 g) and K$_2$CO$_3$ (2.3 g) and the mixture is heated at 150° C. in a microwave oven for 30 min. After cooling to room temperature, water and ethyl acetate are added and the organic layer is dried (MgSO$_4$) and concentrated. The residue is purified by chromatography on silica gel (ethyl acetate/hexane 0:1→1:0). The ester is dissolved in methanol (30 mL) and 4 M aqueous NaOH (3 mL) is added and the mixture is stirred at room temperature for 1 h. The mixture is neutralized with 6 M aqueous HCl, concentrated and then acidified with 6 M aqueous HCl. The precipitate is filtered off washing with a small amount of water and dried by suction to give the title compound.

Intermediate 51

3-Fluoro-4-(2-methyl-1H-imidazol-1-yl)-benzoic acid

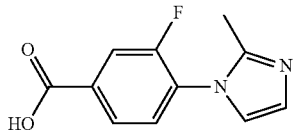 [SMILES: Cc1nccn1-c1ccc(C(=O)O)cc1F]

To a solution of ethyl 3,4-difluorobenzoate (1.5 g) in N,N-dimethylformamide (12 mL) is added 2-methylimidazole (1.3 g) and $K_2CO_3$ (2.2 g) and the mixture is heated at 140° C. in a microwave oven for 1 h. After cooling to room temperature, water and ethyl acetate are added and the organic layer is dried ($MgSO_4$) and concentrated. The residue is purified by chromatography (ethyl acetate/hexane 0:1→1:0). The ester is dissolved in methanol (30 mL) and 4 M aqueous NaOH (3 mL) is added and the mixture is stirred at room temperature for 1 h. The mixture is neutralized with 6 M aqueous HCl, concentrated and then acidified with 6 M aqueous HCl. The precipitate is filtered off washing with a small amount of water and dried by suction to give the title compound.

Intermediate 52

4-(1H-1,2,3,4-tetrazol-1-yl)-benzoic acid

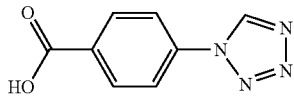

To a solution of ethyl 4-aminobenzoate (1.65 g) in acetic acid (20 mL) is added triethylorthoformate (8 mL) and sodium azide (1.17 g) and the solution is heated at reflux for 4 h. After cooling and removing acetic acid in vacuo, water and dichloromethane are added and the organic layer is separated and dried ($MgSO_4$) and concentrated. The crude ester is dissolved in methanol (30 mL) and 4 M aqueous NaOH solution (3 mL) is added and the solution is stirred at room temperature for 2 h. The mixture is neutralized with 6 M aqueous HCl, concentrated and then acidified with 6 M aqueous HCl. The precipitate is filtered off washing with water and dried by suction to give the title compound.

Intermediate 53

3-Fluoro-4-(1H-1,2,3,4-tetrazol-1-yl)-benzoic acid

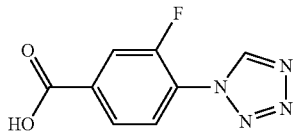 [SMILES: O=C(O)c1ccc(-n2cnnn2)c(F)c1]

The title compound is prepared from ethyl 4-amino-3-fluoro-benzoate following a procedure analogous to that described for Intermediate 52.

Intermediate 54

4-(5-Methyl-1H-1,2,3,4-tetrazol-1-yl)-benzoic acid

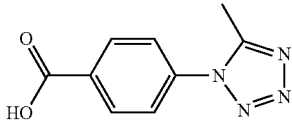

To a solution of ethyl 4-amino-benzoate (1.65 g) in dichloromethane (10 mL) and pyridine (3 mL) is added acetic anhydride (2 g) and the solution is stirred at room temperature overnight. Water is added and the organic layer is separated, washed with saturated aqueous $CuSO_4$ solution and water, dried ($MgSO_4$) and concentrated. The intermediate is dissolved in acetonitrile (30 mL) and sodium azide (6 g) and $SiCl_4$ (6 mL) are added and the mixture is stirred at room temperature overnight. The reaction is quenched by slow addition to an ice/$NaHCO_3$ mixture and the mixture is extracted with ethyl acetate. The combined organic extracts are dried ($MgSO_4$) and concentrated. The crude ester is dissolved in methanol (30 mL) and 4 M aqueous NaOH solution (3 mL) is added and the mixture is stirred at room temperature for 2 h. The mixture is neutralized with 6 M aqueous HCl, concentrated and then acidified with 6 M aqueous HCl. The precipitate is filtered off washing with water and dried by suction to give the title compound.

Intermediate 55

3-Fluoro-4-(5-methyl-1H-1,2,3,4-tetrazol-1-yl)-benzoic acid

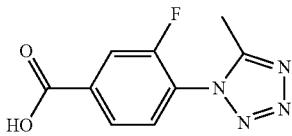 [SMILES: Cc1nnnn1-c1ccc(C(=O)O)cc1F]

The title compound is prepared from ethyl 4-amino-3-fluoro-benzoate following a procedure analogous to that described for Intermediate 54.

Intermediate 56

4-Hydroxypiperidine-1-carbonitrile

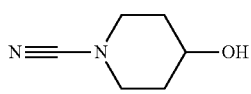

4-Hydroxypiperidine (10 g) dissolved in dichloromethane (20 ml) is added dropwise to a solution of $NaHCO_3$ (16.6 g) in $H_2O$ (10 ml) at 0° C. The mixture is stirred at 0° C. for 30 min and then 3 M cyanogen bromide (36.3 ml) is added. The mixture is stirred at 0° C. for 30 min and then at room temperature for 12 h. The mixture is extracted with dichloromethane. The combined organic layer is washed with brine (15 ml), dried ($MgSO_4$), filtered and concentrated. The crude product is purified by chromatography on silica gel (ethyl acetate/hexane 0:1→1:0) to afford the title compound.

Intermediate 57

N-Hydroxy-2-methylpropanimidamide

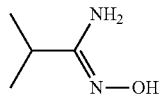

Isobutyronitrile (5 ml) and 50% hydroxylamine in H$_2$O (15 ml) combined in a sealed tube are heated to 80° C. for 4 h. The mixture is concentrated and dried under high vacuum overnight to yield the crude title compound which is used without further purification.

Intermediate 58

1-[3-(Propan-2-yl)-1,2,4-oxadiazol-5-yl]piperidin-4-ol

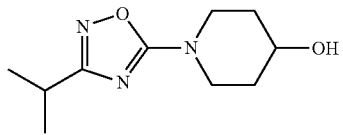

4-Hydroxypiperidine-1-carbonitrile (3.0 g) and N-hydroxy-2-methylpropanimidamide (2.9 g) are dissolved in ethyl acetate (20 ml) and 1 M ZnCl$_2$ in Et$_2$O (29 ml) is added. A precipitate forms and the solvent is decanted off. Additional Et$_2$O (20 ml) is added to wash the precipitate and again is decanted off. Ethanol (20 ml) is added followed by concentrated aqueous HCl (7.5 ml) and the mixture is heated to 100° C. for 3.5 h.

The mixture is concentrated, redissolved in H$_2$O (5 ml) and made basic by addition of concentrated aqueous NaHCO$_3$ solution. The aqueous layer is extracted with dichloromethane (2×50 mL) and the combined organic layer is dried over MgSO$_4$, filtered and concentrated. The crude product is purified by chromatography on silica gel (ethyl acetate/hexane 0:1→1:0) to afford the title compound.

Intermediate 59

1-[3-(Propan-2-yl)-1,2,4-oxadiazol-5-yl]piperidin-4-one

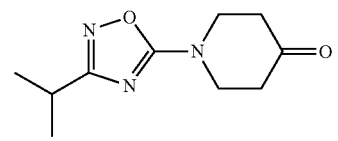

1-[3-(Propan-2-yl)-1,2,4-oxadiazol-5-yl]piperidin-4-ol (0.5 g) is dissolved in dichloromethane (75 mL) and 4 A molecular sieves (4 g) is added followed by N-methylmorpholine-N-oxide (1.52 g) and tetrapropylammonium perrhutenate (0.018 g) and the mixture is stirred at room temperature for 1 h. The reaction is filtered through celite and the filtrate is washed with water (2×50 mL). The combined aqueous layers are extracted with dichloromethane (100 mL). The organic layers are combined, dried over Na$_2$SO$_4$, filtered and concentrated to a dark liquid which crystallized upon standing to yield the title compound.

Intermediate 60

8-(5-Chloropyrimidin-2-yl)-1,4-dioxa-8-azaspiro[4.5]decane

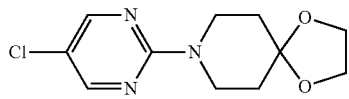 [SMILES: Clc1cnc(N2CCC3(CC2)OCCO3)nc1]

1,4-Dioxa-8-azaspiro[4.5]decane (2.39 g) is combined with 2,5-dichloropyrimidine (2.44 g) in N,N-dimethylformamide (50 mL), 1,4-dioxane (75 mL) and triethylamine (6.7 mL) in a glass pressure reaction vessel. The mixture is heated with stirring at 120° C. for 16 h. After cooling to room temperature, the solution is concentrated and partitioned between dichloromethane (100 mL) and water (100 mL). The aqueous layer is extracted with dichloromethane (100 mL). The dichloromethane layers are combined, washed with water (2×100 mL), dried over Na$_2$SO$_4$, filtered and concentrated to yield the title compound.

Intermediate 61

8-[3-Fluoro-5-(trifluoromethyl)-pyridin-2-yl]-1,4-dioxa-8-azaspiro[4.5]decane

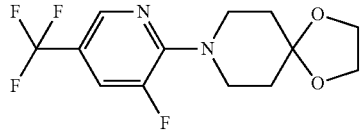 [SMILES: Fc1cc(C(F)(F)F)cnc1N1CCC2(CC1)OCCO2]

A mixture of 1,4-dioxa-8-azaspiro[4.5]decane (1.76 g), 2-bromo-3-fluoro-5-(trifluoromethyl)-pyridine (2.95 g), N,N-dimethylformamide (50 mL), 1,4-dioxane (75 mL) and triethylamine (5.07 ml) is stirred in a sealed vessel at 120° C. for 1 h. After cooling to room temperature, the mixture is concentrated and partitioned between ethyl acetate (100 mL) and water (100 mL). The water layer is extracted with ethyl acetate (100 mL) and the combined organic layers are dried over Na$_2$SO$_4$, filtered and concentrated to yield the title compound.

Intermediate 62

8-(5-Ethylpyrimidin-2-yl)-1,4-dioxa-8-azaspiro[4.5]decane

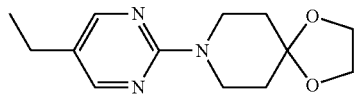

The title compound is prepared from 1,4-dioxa-8-azaspiro[4.5]decane and 2-chloro-5-ethyl-pyrimidine following a procedure analogous to that described for Intermediate 61.

Intermediate 63

1-(5-Chloropyrimidin-2-yl)piperidin-4-one

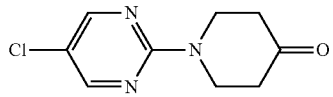

A solution of 8-(5-chloropyrimidin-2-yl)-1,4-dioxa-8-azaspiro[4.5]decane (4.2 g) in 6 M aqueous HCl (50 mL) is stirred at room temperature for 60 h. The solution is cooled in ice bath and 4 M aqueous NaOH solution (90 mL) is added in portions to make the solution strongly basic (pH~14). The mixture is extracted with dichloromethane (2×200 mL) and the combined organic layers are dried over $Na_2SO_4$, filtered and concentrated to yield the title compound.

Intermediate 64

1-[3-Fluoro-5-(trifluoromethyl)pyridin-2-yl]piperidin-4-one

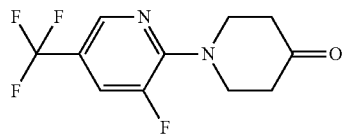 [SMILES: O=C1CCN(c2ncc(C(F)(F)F)cc2F)CC1]

The title compound is prepared from 8-[3-fluoro-5-(trifluoromethyl)-pyridin-2-yl]-1,4-dioxa-8-azaspiro[4.5]decane following a procedure analogous to that described for Intermediate 63.

Intermediate 65

1-(5-Ethyl-pyrimidin-2-yl)piperidin-4-one

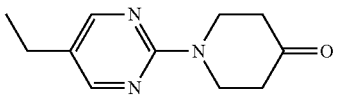

The title compound is prepared from (8-(5-ethylpyrimidin-2-yl)-1,4-dioxa-8-azaspiro[4.5]decane following a procedure analogous to that described for Intermediate 63.

Intermediate 66

[1-(5-Chloro-pyrimidin-2-yl)-piperidin-4-yl]-cyclopropyl-amine

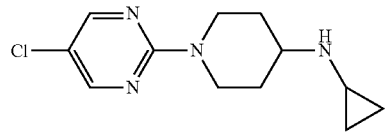

1-(5-Chloropyrimidin-2-yl)piperidin-4-one (1.5 g) is dissolved in anhydrous dichloromethane (25 mL) and cyclopropylamine (0.42 g) is added followed by glacial acetic acid (0.80 mL). Sodium triacetoxyborohydride (1.8 g) is added in one portion under nitrogen atmosphere and the resulting mixture is stirred at room temperature for 17 h. The mixture is diluted with dichloromethane (25 mL) and extracted with 3 M aqueous HCl (75 mL and 50 mL). The combined HCl layers are cooled on ice and 4 M aqueous NaOH solution (100 mL) is added in portions until the mixture is strongly basic (pH~14). The mixture is extracted with dichloromethane (150 mL and 100 mL) and the combined organic layers are dried over $Na_2SO_4$, filtered and concentrated to yield the title compound.

Intermediate 67

Cyclopropyl-(3'-fluoro-5'-trifluoromethyl-3,4,5,6-tetrahydro-2H-[1,2']bipyridinyl-4-yl)-amine

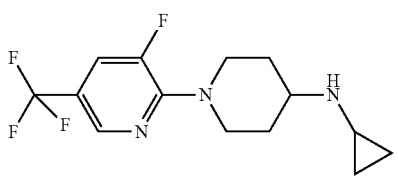 [SMILES: Fc1cc(C(F)(F)F)cnc1N1CCC(NC2CC2)CC1]

The title compound is prepared from 1-(3-fluoro-5-trifluoromethyl-pyridin-2-yl)-piperidin-4-one and cyclopropylamine following a procedure analogous to that described for Intermediate 66.

Intermediate 68

Cyclopropyl-[1-(5-ethyl-pyrimidin-2-yl)-piperidin-4-yl]-amine

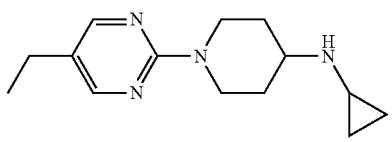 [SMILES: CCc1cnc(N2CCC(NC3CC3)CC2)nc1]

The title compound is prepared from 1-(5-ethyl-pyrimidin-2-yl)-piperidin-4-one and cyclopropylamine following a procedure analogous to that described for Intermediate 66.

Intermediate 69

Cyclopropyl-[1-(3-isopropyl-[1,2,4]oxadiazol-5-yl)-piperidin-4-yl]-amine

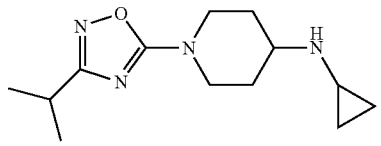 [SMILES: CC(C)c1noc(N2CCC(NC3CC3)CC2)n1]

The title compound is prepared from 1-(3-isopropyl-[1,2,4]oxadiazol-5-yl)-piperidin-2-one and cyclopropylamine following a procedure analogous to that described for Intermediate 66.

Intermediates 70

(3S,4R)-4-Cyclopropylamino-3-fluoro-piperidine-1-carboxylic acid benzyl ester (Isomer 1) and (3R,4S)-4-Cyclopropylamino-3-fluoro-piperidine-1-carboxylic acid benzyl ester (Isomer 2)

Isomer 1

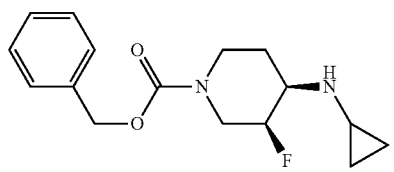

Isomer 2

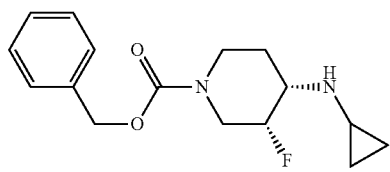

To a solution of 3-fluoro-4-oxo-piperidine-1-carboxylic acid benzyl ester (10.0 g) and cyclopropylamine (2.5 g) in dichloromethane (100 mL) are added sodium triacetoxyborohydride (10.1 g) and glacial acetic acid (5.0 g). The mixture is stirred at room temperature for 20 h. 2 N aqueous NaOH solution (60 mL) is added to reach pH 10 and the mixture is extracted with dichloromethane (2×50 mL). The combined organic phases are dried over sodium sulfate and concentrated in vacuo. The residue is purified by silica gel chromatography (dichloromethane/methanol 9:1) to afford the tilte compound as a mixture of isomers. Chiral SFC separation (Berger/Thar/Waters Multi-gram II prep SFC system with UV detection; column: Chiral Technologies Chiralcel AD-H, 5 um, 21×250 mm; gradient: 65 mL/min, 10% ethanol with 0.5% dimethyl-ethylamine) gives the separated cis isomers of unknown absolute stereochemistry arbitrarily assigned as Isomer 1 (first eluting) and Isomer 2 (second eluting).

Intermediate 71

Cyclopropyl-[(3S,4R)-3-fluoro-piperidin-4-yl]-carbamic acid tert-butyl ester (Absolute Configurations Arbitrarily Assigned)

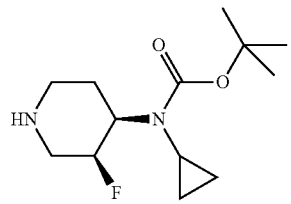 [SMILES: CC(C)(C)OC(=O)N(C1CC1)[C@@H]1CCNC[C@@H]1F]

(3S,4R)-4-Cyclopropylamino-3-fluoro-piperidine-1-carboxylic acid benzyl ester (Isomer 1 of Intermediates 70, 3 g) is dissolved in tetrahydrofuran/water 1:1 (100 mL). NaOH (800 mg) is added followed by di-tert-butyl dicarbonate (2.6 g) and the mixture is stirred rapidly at room temperature overnight. The mixture is heated to reflux and additional portions of di-tert-butyl dicarbonate are added over 2 d (3×2.6 g). The mixture is extracted with ethyl acetate and the organic extracts are washed with brine, dried over MgSO$_4$ and concentrated. The residue is chromatographed on silica gel (ethyl acetate/hexane) to give the intermediate. The intermediate is dissolved in ethyl acetate (30 mL) and 10% Pd/C (200 mg) is added and the mixture is stirred under an atmosphere of H$_2$ (1 bar) at room temperature for 2 h. The mixture is filtered through celite and concentrated to give the title compound.

Intermediate 72

Cyclopropyl-[(3R,4S)-3-fluoro-piperidin-4-yl]-carbamic acid tert-butyl ester (Absolute Configurations Arbitrarily Assigned)

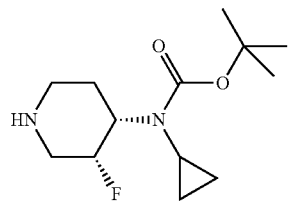 [SMILES: CC(C)(C)OC(=O)N(C1CC1)[C@H]1CCNC[C@H]1F]

The title compound is prepared from (3R,4S)-4-cyclopropylamino-3-fluoro-piperidine-1-carboxylic acid benzyl ester (Isomer 2 of Intermediates 70) following a procedure analogous to that described for Intermediate 71.

Intermediate 73

(3S,4R)-Cyclopropyl-(3-fluoro-5'-trifluoromethyl-3,4,5,6-tetrahydro-2H-[1,2']bipyridinyl-4-yl)-amine (Absolute Configurations Arbitrarily Assigned)

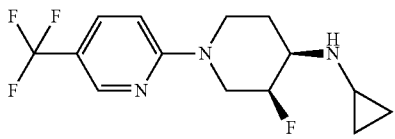 [SMILES: F[C@H]1CN(c2ccc(C(F)(F)F)cn2)CC[C@H]1NC1CC1]

A solution of cyclopropyl-[(3S,4R)-3-fluoro-piperidin-4-yl]-carbamic acid tert-butyl ester (100 mg), 2-chloro-5-trifluoromethyl-pyridine (141 mg) and triethylamine (78 mg) in N,N-dimethylformamide (2 mL) is heated in a microwave reactor at 130° C. for 3 h. After concentration the residue is purified by chromatography on silica gel (ethyl acetate/hexane 0:1→3:7) to give the tert-butoxycarbonyl protected product. The protected product is dissolved in dichloromethane (3 mL) and trifluoroacetic acid (0.5 mL) is added and the solution is stirred at room temperature for 1 h. After concentration dichloromethane (3 mL) and 2 M aqueous NaOH solution (2 mL) are added and the organic layer is separated, dried over $MgSO_4$ and concentrated to give the title compound.

Intermediate 74

(3R,4S)-Cyclopropyl-(3-fluoro-5'-trifluoromethyl-3,4,5,6-tetrahydro-2H-[1,2']bipyridinyl-4-yl)-amine (Absolute Configurations Arbitrarily Assigned)

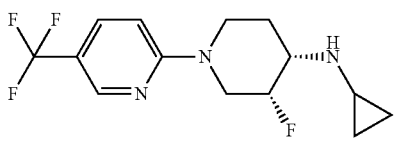 [SMILES: F[C@@H]1CN(c2ccc(C(F)(F)F)cn2)CC[C@@H]1NC1CC1]

The title compound is prepared from cyclopropyl-[(3R,4S)-3-fluoro-piperidin-4-yl]-carbamic acid tert-butyl ester and 2-chloro-5-trifluoromethyl-pyridine following a procedure analogous to that described for Intermediate 73.

Intermediate 75

(3S,4R)-Cyclopropyl-[1-(5-ethyl-pyrimidin-2-yl)-3-fluoro-piperidin-4-yl]-amine (Absolute Configurations Arbitrarily Assigned)

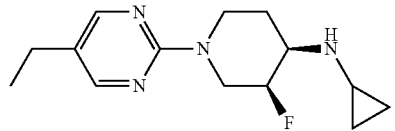 [SMILES: CCc1cnc(N2CC[C@@H](NC3CC3)[C@@H](F)C2)nc1]

The title compound is prepared from cyclopropyl-[(3S,4R)-3-fluoro-piperidin-4-yl]-carbamic acid tert-butyl ester and 2-chloro-5-ethyl-pyrimidine following a procedure analogous to that described for Intermediate 73.

Intermediate 76

(3R,4S)-Cyclopropyl-[1-(5-ethyl-pyrimidin-2-yl)-3-fluoro-piperidin-4-yl]-amine (Absolute Configurations Arbitrarily Assigned)

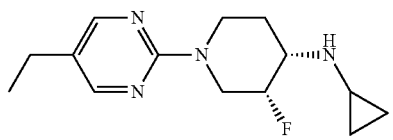 [SMILES: CCc1cnc(N2CC[C@H](NC3CC3)[C@H](F)C2)nc1]

The title compound is prepared from cyclopropyl-[(3R,4S)-3-fluoro-piperidin-4-yl]-carbamic acid tert-butyl ester and 2-chloro-5-ethyl-pyrimidine following a procedure analogous to that described for Intermediate 73.

Example 1

N-Cyclopropyl-N-[1-(3-isopropyl-[1,2,4]oxadiazol-5-yl)-piperidin-4-yl]-4-oxazol-5-yl-benzamide

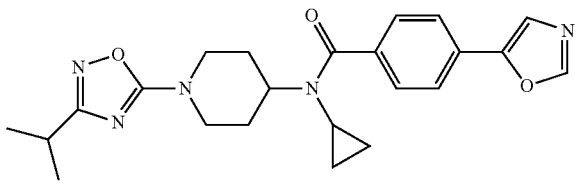 [SMILES: CC(C)c1noc(N2CCC(N(C(=O)c3ccc(-c4cnco4)cc3)C3CC3)CC2)n1]

A 0.5 M solution of zinc chloride in tetrahydrofuran (5.20 mL) is added dropwise at room temperature to a mixture of N-hydroxy-isobutyramidine (266 mg) and N-(1-cyano-piperidin-4-yl)-N-cyclopropyl-4-oxazol-5-yl-benzamide (600 mg) in ethyl acetate (25 mL). The reaction mixture is stirred at 50° C. for 3 h and cooled to room temperature. The precipitate is filtered off and heated to 100° C. for 2 h in a mixture of ethanol (10 mL) and glacial acetic acid (5 mL). The solvents are evaporated and the residue is chromatographed on silica gel [ethyl acetate/cyclohexane/methanol 9:9:2] to give the title compound. LC (method 6): $t_R$=1.66 min; Mass spectrum (ESI$^+$): m/z=422 [M+H]$^+$.

Example 2

N-Cyclopropyl-N-[1-(3-isobutyl-[1,2,4]oxadiazol-5-yl)-piperidin-4-yl]-4-oxazol-5-yl-benzamide

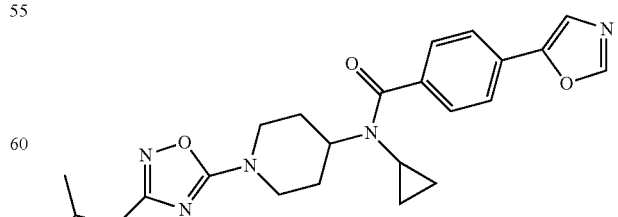

The title compound is prepared from N-(1-cyano-piperidin-4-yl)-N-cyclopropyl-4-oxazol-5-yl-benzamide and N-hydroxy-3-methyl-butyramidine following a procedure analogous to that described in Example 1. LC (method 6): $t_R$=1.76 min; Mass spectrum (ESI$^+$): m/z=436 [M+H]$^+$.

Example 3

N-[1-(3-tert-Butyl-[1,2,4]oxadiazol-5-yl)-piperidin-4-yl]-N-cyclopropyl-4-oxazol-5-yl-benzamide

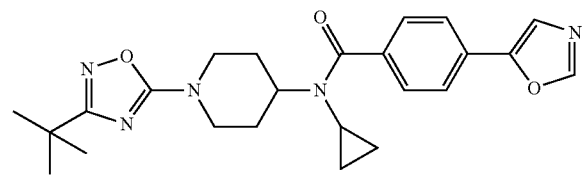 [SMILES: CC(C)(C)c1noc(N2CCC(N(C(=O)c3ccc(-c4cnco4)cc3)C3CC3)CC2)n1]

The title compound is prepared from N-(1-cyano-piperidin-4-yl)-N-cyclopropyl-4-oxazol-5-yl-benzamide and N-hydroxy-2,2-dimethyl-propionamidine following a procedure analogous to that described in Example 1. LC (method 6): $t_R$=1.68 min; Mass spectrum (ESI$^+$): m/z=436 [M+H]$^+$.

Example 4

N-Cyclopropyl-N-[1-(3-methoxymethyl-[1,2,4]oxadiazol-5-yl)-piperidin-4-yl]-4-oxazol-5-yl-benzamide

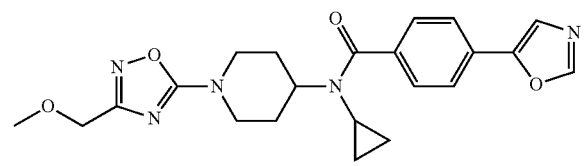 [SMILES: COCc1noc(N2CCC(N(C(=O)c3ccc(-c4cnco4)cc3)C3CC3)CC2)n1]

The title compound is prepared from N-(1-cyano-piperidin-4-yl)-N-cyclopropyl-4-oxazol-5-yl-benzamide and N-hydroxy-2-methoxy-acetamidine following a procedure analogous to that described in Example 1. LC (method 6): $t_R$=1.61 min; Mass spectrum (ESI$^+$): m/z=424 [M+H]$^+$.

Example 5

N-Cyclopropyl-N-{1-[3-(4-iodo-phenyl)-[1,2,4]oxadiazol-5-yl]-piperidin-4-yl}-4-oxazol-5-yl-benzamide

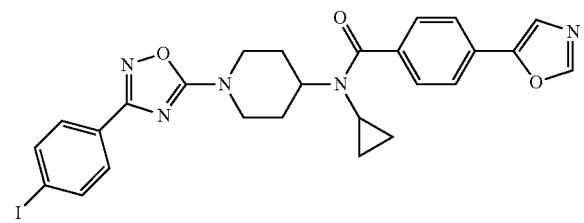 [SMILES: O=C(c1ccc(-c2cnco2)cc1)N(C1CC1)C1CCN(c2nc(-c3ccc(I)cc3)no2)CC1]

The title compound is prepared from N-(1-cyano-piperidin-4-yl)-N-cyclopropyl-4-oxazol-5-yl-benzamide and N-hydroxy-4-iodo-benzamidine following a procedure analogous to that described in Example 1. LC (method 6): $t_R$=1.88 min; Mass spectrum (ESI$^+$): m/z=582 [M+H]$^+$.

Example 6

N-Cyclopropyl-4-oxazol-5-yl-N-[1-(3-phenyl-[1,2,4]oxadiazol-5-yl)-piperidin-4-yl]-benzamide

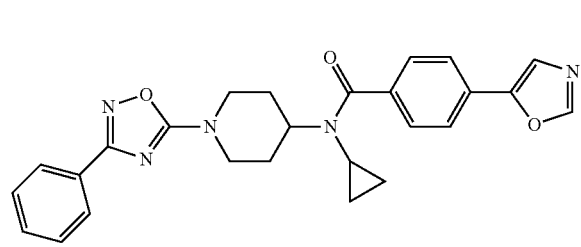 [SMILES: O=C(c1ccc(-c2cnco2)cc1)N(C1CC1)C1CCN(c2nc(-c3ccccc3)no2)CC1]

The title compound is prepared from N-(1-cyano-piperidin-4-yl)-N-cyclopropyl-4-oxazol-5-yl-benzamide and N-hydroxy-benzamidine following a procedure analogous to that described in Example 1. LC (method 6): $t_R$=1.85 min; Mass spectrum (ESI$^+$): m/z=456 [M+H]$^+$.

Example 7

N-[1-(3-Benzyl-[1,2,4]oxadiazol-5-yl)-piperidin-4-yl]-N-cyclopropyl-4-oxazol-5-yl-benzamide

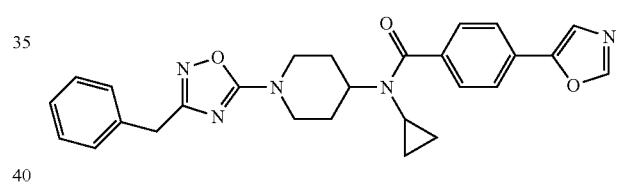

The title compound is prepared from N-(1-cyano-piperidin-4-yl)-N-cyclopropyl-4-oxazol-5-yl-benzamide and N-hydroxy-2-phenyl-acetamidine following a procedure analogous to that described in Example 1. LC (method 6): $t_R$=1.69 min; Mass spectrum (ESI$^+$): m/z=470 [M+H]$^+$.

Example 8

N-Cyclopropyl-4-oxazol-5-yl-N-[1-(3-propyl-[1,2,4]oxadiazol-5-yl)-piperidin-4-yl]-benzamide

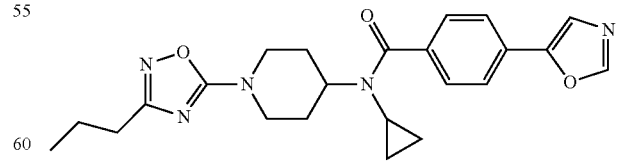

The title compound is prepared from N-(1-cyano-piperidin-4-yl)-N-cyclopropyl-4-oxazol-5-yl-benzamide and N-hydroxy-butyramidine following a procedure analogous to that described in Example 1. LC (method 6): $t_R$=1.15 min; Mass spectrum (ESI$^+$): m/z=422 [M+H]$^+$.

Example 9

N-Cyclopropyl-4-oxazol-5-yl-N-[1-(3-pyridin-4-yl-[1,2,4]oxadiazol-5-yl)-piperidin-4-yl]-benzamide

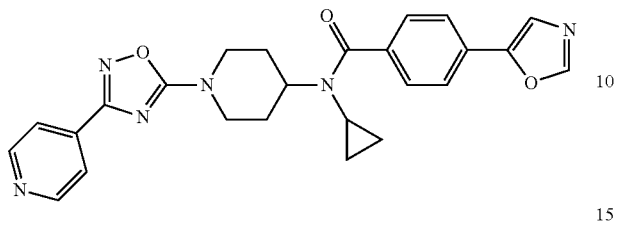

The title compound is prepared from N-(1-cyano-piperidin-4-yl)-N-cyclopropyl-4-oxazol-5-yl-benzamide and N-hydroxy-isonicotinamidine following a procedure analogous to that described in Example 1. LC (method 6): $t_R$=1.51 min; Mass spectrum (ESI$^+$): m/z=457 [M+H]$^+$.

Example 10

N-Cyclopropyl-N-{1-[3-(4-fluoro-phenyl)-[1,2,4]oxadiazol-5-yl]-piperidin-4-yl}-4-oxazol-5-yl-benzamide

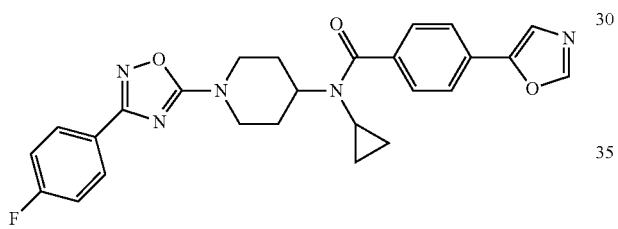

The title compound is prepared from N-(1-cyano-piperidin-4-yl)-N-cyclopropyl-4-oxazol-5-yl-benzamide and 4-fluoro-N-hydroxy-benzamidine following a procedure analogous to that described in Example 1. LC (method 6): $t_R$=1.87 min; Mass spectrum (ESI$^+$): m/z=474 [M+H]$^+$.

Example 11

N-{1-[3-(3-Bromo-phenyl)-[1,2,4]oxadiazol-5-yl]-piperidin-4-yl}-N-cyclopropyl-4-oxazol-5-yl-benzamide

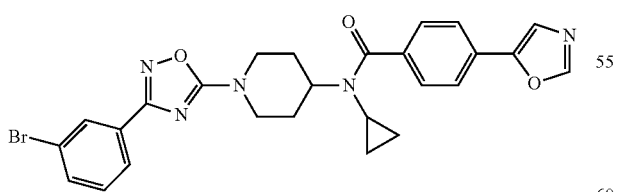

The title compound is prepared from N-(1-cyano-piperidin-4-yl)-N-cyclopropyl-4-oxazol-5-yl-benzamide and 3-bromo-N-hydroxy-benzamidine following a procedure analogous to that described in Example 1. LC (method 6): $t_R$=2.09 min; Mass spectrum (ESI$^+$): m/z=534/536 (Br) [M+H]$^+$.

Example 12

N-Cyclopropyl-N-[1-(3-ethyl-[1,2,4]oxadiazol-5-yl)-piperidin-4-yl]-4-oxazol-5-yl-benzamide

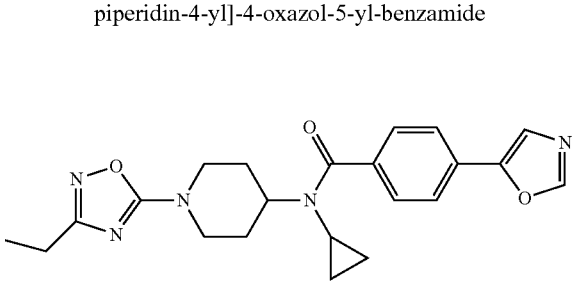

The title compound is prepared from N-(1-cyano-piperidin-4-yl)-N-cyclopropyl-4-oxazol-5-yl-benzamide and N-hydroxy-propionamidine following a procedure analogous to that described in Example 1. LC (method 6): $t_R$=1.56 min; Mass spectrum (ESI$^+$): m/z=408 [M+H]$^+$.

Example 13

N-[1-(3-Allyl-[1,2,4]oxadiazol-5-yl)-piperidin-4-yl]-N-cyclopropyl-4-oxazol-5-yl-benzamide

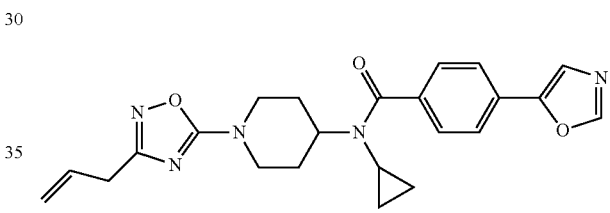

The title compound is prepared from N-(1-cyano-piperidin-4-yl)-N-cyclopropyl-4-oxazol-5-yl-benzamide and N-hydroxy-but-3-enamidine following a procedure analogous to that described in Example 1. LC (method 6): $t_R$=1.65 min; Mass spectrum (ESI$^+$): m/z=420 [M+H]$^+$.

Example 14

N-Cyclopropyl-4-oxazol-5-yl-N-[1-(3-thiophen-3-yl-[1,2,4]oxadiazol-5-yl)-piperidin-4-yl]-benzamide

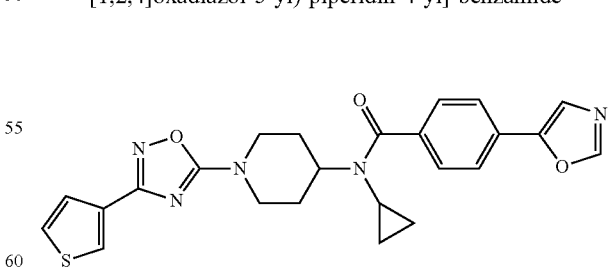

The title compound is prepared from N-(1-cyano-piperidin-4-yl)-N-cyclopropyl-4-oxazol-5-yl-benzamide and N-hydroxy-thiophene-3-carboxamidine following a procedure analogous to that described in Example 1. LC (method 6): $t_R$=1.78 min; Mass spectrum (ESI$^+$): m/z=462 [M+H]$^+$.

Example 15

N-Cyclopropyl-4-oxazol-5-yl-N-[1-(3-pyridin-3-yl-[1,2,4]oxadiazol-5-yl)-piperidin-4-yl]-benzamide

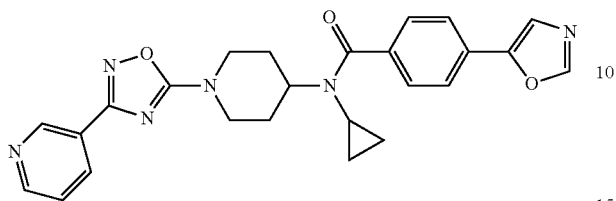

The title compound is prepared from N-(1-cyano-piperidin-4-yl)-N-cyclopropyl-4-oxazol-5-yl-benzamide and N-hydroxy-nicotinamidine following a procedure analogous to that described in Example 1. LC (method 6): $t_R$=1.57 min; Mass spectrum (ESI$^+$): m/z=457 [M+H]$^+$.

Example 16

N-Cyclopropyl-N-{1-[3-(2-methyl-thiazol-4-yl)-[1,2,4]oxadiazol-5-yl]-piperidin-4-yl}-4-oxazol-5-yl-benzamide

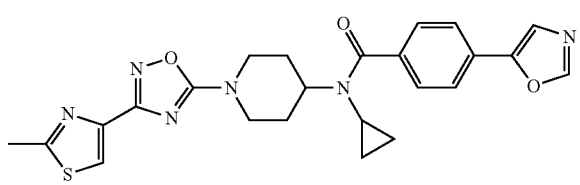 [SMILES: Cc1nc(-c2noc(N3CCC(N(C(=O)c4ccc(-c5cnco5)cc4)C4CC4)CC3)n2)cs1]

The title compound is prepared from N-(1-cyano-piperidin-4-yl)-N-cyclopropyl-4-oxazol-5-yl-benzamide and N-hydroxy-2-methyl-thiazole-4-carboxamidine following a procedure analogous to that described in Example 1. LC (method 6): $t_R$=1.64 min; Mass spectrum (ESI$^+$): m/z=477 [M+H]$^+$.

Example 17

N-Cyclopropyl-N-[1-(3-phenyl-[1,2,4]oxadiazol-5-yl)-piperidin-4-yl]-4-pyridin-4-yl-benzamide

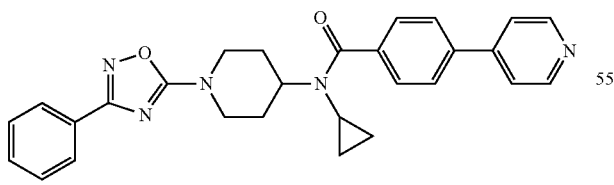

2-(1H-Benzotriazol-1-yl)-1,1,3,3-tetramethyluronium tetrafluoroborate (75 mg) and ethyldiisopropylamine (74 µL) are added to a solution of 4-pyridin-4-yl-benzoic acid (42 mg) in N,N-dimethylformamide (5 mL) at room temperature. The solution is stirred for 10 min prior to the addition of cyclopropyl-[1-(3-phenyl-[1,2,4]oxadiazol-5-yl)-piperidin-4-yl]-amine (60 mg). The resulting mixture is stirred at 60° C. for 5 h, cooled to room temperature and concentrated in vacuo. The crude product is purified by HPLC (H$_2$O/MeOH/TFA). LC (method 6): $t_R$=1.44 min; Mass spectrum (ESI$^+$): m/z=466 [M+H]$^+$.

Example 18

N-Cyclopropyl-4-oxazol-5-yl-N-[1-(3-pyridin-2-yl-[1,2,4]oxadiazol-5-yl)-piperidin-4-yl]-benzamide

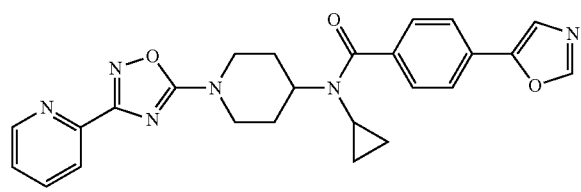 [SMILES: O=C(c1ccc(-c2cnco2)cc1)N(C1CC1)C1CCN(c2nc(-c3ccccn3)no2)CC1]

The title compound is prepared from N-(1-cyano-piperidin-4-yl)-N-cyclopropyl-4-oxazol-5-yl-benzamide and N-hydroxy-pyridine-2-carboxamidine following a procedure analogous to that described in Example 1. LC (method 6): $t_R$=1.60 min; Mass spectrum (ESI$^+$): m/z=457 [M+H]$^+$.

Example 19

N-Cyclopropyl-N-[1-(5-ethyl-pyrimidin-2-yl)-piperidin-4-yl]-4-oxazol-5-yl-benzamide

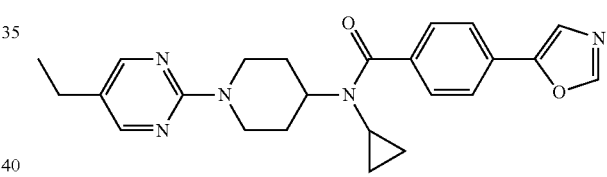

A mixture of N-cyclopropyl-4-oxazol-5-yl-N-piperidin-4-yl-benzamide hydrogen chloride salt (52 mg), ethyldiisopropylamine (59 mg), and 2-chloro-5-ethylpyrimidine (21 mg) in N,N-dimethylformamide (1.0 mL) and 1,4-dioxane (1.5 mL) is stirred over night at 120° C. After cooling to room temperature, the solvents are evaporated and the residue is purified by HPLC (H$_2$O/MeOH/TFA) to give the title compound. LC (method 9): $t_R$=1.74 min; Mass spectrum (ESI$^+$): m/z=418 [M+H]$^+$.

Example 20

N-Cyclopropyl-4-oxazol-5-yl-N-(1-pyrimidin-2-yl-piperidin-4-yl)-benzamide

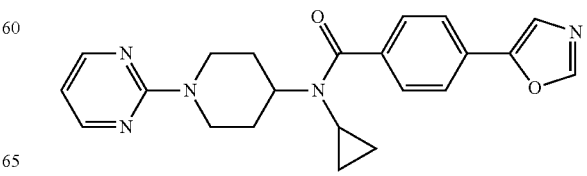

The title compound is prepared from N-cyclopropyl-4-oxazol-5-yl-N-piperidin-4-yl-benzamide and 2-chloro-pyrimidine following a procedure analogous to that described in Example 19. LC (method 5): $t_R$=1.89 min; Mass spectrum (ESI$^+$): m/z=390 [M+H]$^+$.

Example 21

N-[1-(5-Cyano-pyridin-2-yl)-piperidin-4-yl]-N-cyclopropyl-4-oxazol-5-yl-benzamide

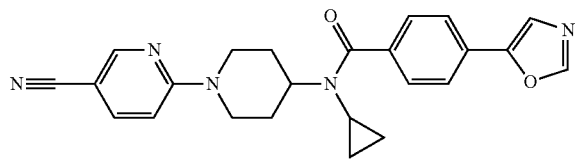 [SMILES: N#Cc1ccc(N2CCC(N(C(=O)c3ccc(-c4cnco4)cc3)C3CC3)CC2)nc1]

The title compound is prepared from N-cyclopropyl-4-oxazol-5-yl-N-piperidin-4-yl-benzamide and 6-chloro-nicotinonitrile following a procedure analogous to that described in Example 19. LC (method 9): $t_R$=2.02 min; Mass spectrum (ESI$^+$): m/z=414 [M+H]$^+$.

Example 22

N-(1-Benzooxazol-2-yl-piperidin-4-yl)-N-cyclopropyl-4-oxazol-5-yl-benzamide

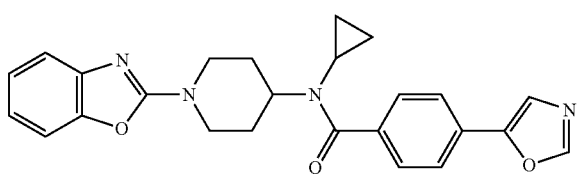 [SMILES: O=C(c1ccc(-c2cnco2)cc1)N(C1CC1)C1CCN(c2nc3ccccc3o2)CC1]

The title compound is prepared from N-cyclopropyl-4-oxazol-5-yl-N-piperidin-4-yl-benzamide and 2-chloro-benzooxazole following a procedure analogous to that described in Example 19. LC (method 9): $t_R$=1.85 min; Mass spectrum (ESI$^+$): m/z=429 [M+H]$^+$.

Example 23

N-Cyclopropyl-4-oxazol-5-yl-N-[1-(5-propyl-pyrimidin-2-yl)-piperidin-4-yl]-benzamide

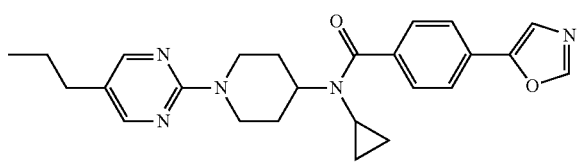 [SMILES: CCCc1cnc(N2CCC(N(C(=O)c3ccc(-c4cnco4)cc3)C3CC3)CC2)nc1]

The title compound is prepared from N-cyclopropyl-4-oxazol-5-yl-N-piperidin-4-yl-benzamide and 2-chloro-5-propyl-pyrimidine following a procedure analogous to that described in Example 19. LC (method 9): $t_R$=1.86 min; Mass spectrum (ESI$^+$): m/z=432 [M+H]$^+$.

Example 24

N-{1-[5-(4-Chloro-phenyl)-pyrimidin-2-yl]-piperidin-4-yl}-N-cyclopropyl-4-oxazol-5-yl-benzamide

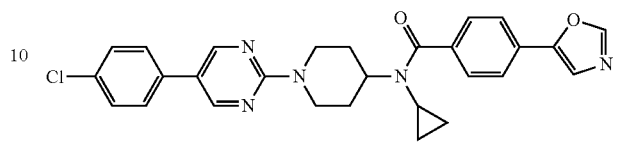

The title compound is prepared from N-cyclopropyl-4-oxazol-5-yl-N-piperidin-4-yl-benzamide and 2-chloro-5-(4-chloro-phenyl)-pyrimidine following a procedure analogous to that described in Example 19. LC (method 9): $t_R$=2.42 min; Mass spectrum (ESI$^+$): m/z=500/502 (Cl) [M+H]$^+$.

Example 25

N-[1-(5-Bromo-pyrimidin-2-yl)-piperidin-4-yl]-N-cyclopropyl-4-oxazol-5-yl-benzamide

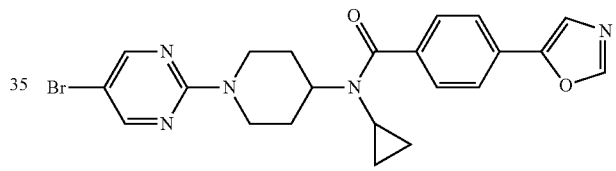

The title compound is prepared from N-cyclopropyl-4-oxazol-5-yl-N-piperidin-4-yl-benzamide and 5-bromo-2-fluoro-pyrimidine following a procedure analogous to that described in Example 19. LC (method 9): $t_R$=2.32 min; Mass spectrum (ESI$^+$): m/z=468/470 (Br) [M+H]$^+$.

Example 26

N-Cyclopropyl-N-[1-(5-methoxy-pyrimidin-2-yl)-piperidin-4-yl]-4-oxazol-5-yl-benzamide

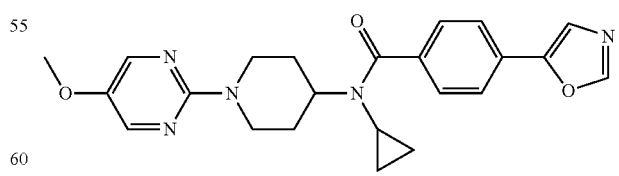

The title compound is prepared from N-cyclopropyl-4-oxazol-5-yl-N-piperidin-4-yl-benzamide and 2-chloro-5-methoxy-pyrimidine following a procedure analogous to that described in Example 19. LC (method 9): $t_R$=1.88 min; Mass spectrum (ESI$^+$): m/z=420 [M+H]$^+$.

Example 27

N-Cyclopropyl-N-{1-[5-(4-methoxy-phenyl)-pyrimidin-2-yl]-piperidin-4-yl}-4-oxazol-5-yl-benzamide

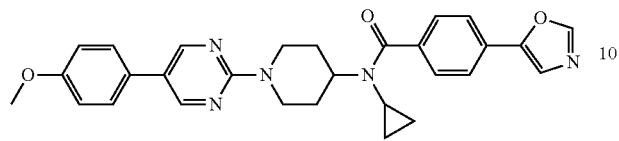

The title compound is prepared from N-cyclopropyl-4-oxazol-5-yl-N-piperidin-4-yl-benzamide and 2-chloro-5-(4-methoxy-phenyl)-pyrimidine following a procedure analogous to that described in Example 19. LC (method 9): $t_R$=2.33 min; Mass spectrum (ESI$^+$): m/z=496 [M+H]$^+$.

Example 28

N-Cyclopropyl-4-oxazol-5-yl-N-(1-pyridin-2-yl-piperidin-4-yl)-benzamide

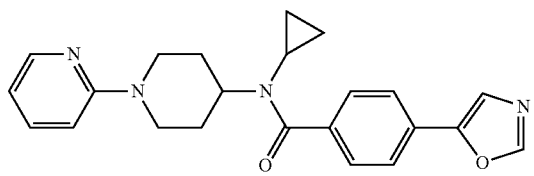 [SMILES: O=C(c1ccc(-c2cnco2)cc1)N(C1CC1)C1CCN(c2ccccn2)CC1]

The title compound is prepared from N-cyclopropyl-4-oxazol-5-yl-N-piperidin-4-yl-benzamide and 2-fluoro-pyridine following a procedure analogous to that described in Example 19. LC (method 9): $t_R$=1.46 min; Mass spectrum (ESI$^+$): m/z=389 [M+H]$^+$.

Example 29

N-Cyclopropyl-N-[1-(5-fluoro-pyrimidin-2-yl)-piperidin-4-yl]-4-oxazol-5-yl-benzamide

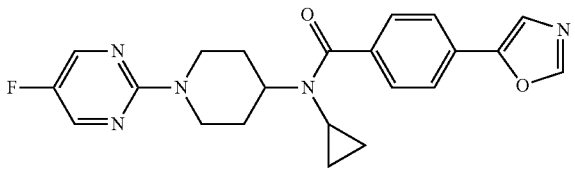 [SMILES: O=C(c1ccc(-c2cnco2)cc1)N(C1CC1)C1CCN(c2ncc(F)cn2)CC1]

The title compound is prepared from N-cyclopropyl-4-oxazol-5-yl-N-piperidin-4-yl-benzamide and 2-chloro-5-fluoro-pyrimidine following a procedure analogous to that described in Example 19. LC (method 5): $t_R$=2.14 min; Mass spectrum (ESI$^+$): m/z=408 [M+H]$^+$.

Example 30

N-[1-(5-Chloro-pyrimidin-2-yl)-piperidin-4-yl]-N-cyclopropyl-4-oxazol-5-yl-benzamide

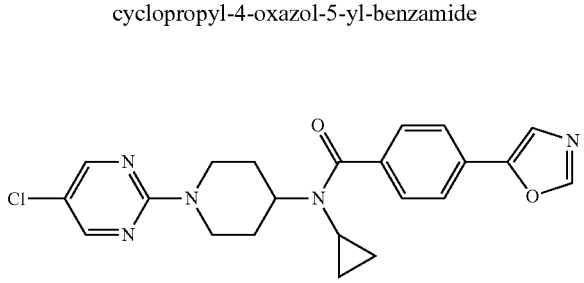

The title compound is prepared from N-cyclopropyl-4-oxazol-5-yl-N-piperidin-4-yl-benzamide and 2,5-dichloro-pyrimidine following a procedure analogous to that described in Example 19. LC (method 5): $t_R$=2.27 min; Mass spectrum (ESI$^+$): m/z=424/426 (Cl) [M+H]$^+$.

Example 31

N-Cyclopropyl-4-oxazol-5-yl-N-[1-(5-trifluoromethyl-pyridin-2-yl)-piperidin-4-yl]-benzamide

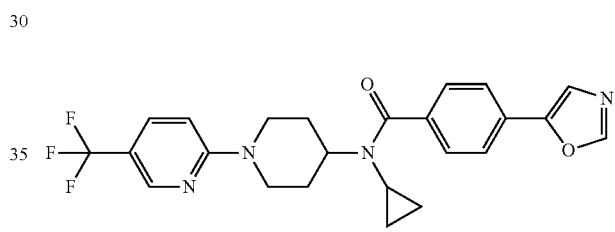

The title compound is prepared from N-cyclopropyl-4-oxazol-5-yl-N-piperidin-4-yl-benzamide and 2-chloro-5-trifluoromethyl-pyridine following a procedure analogous to that described in Example 19. LC (method 5): $t_R$=2.18 min; Mass spectrum (ESI$^+$): m/z=457 [M+H]$^+$.

Example 32

N-[1-(5-Bromo-pyridin-2-yl)-piperidin-4-yl]-N-cyclopropyl-4-oxazol-5-yl-benzamide

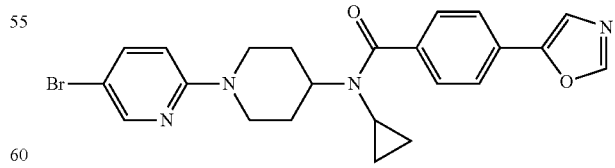

The title compound is prepared from N-cyclopropyl-4-oxazol-5-yl-N-piperidin-4-yl-benzamide and 5-bromo-2-fluoro-pyridine following a procedure analogous to that described in Example 19. LC (method 10): $t_R$=1.92 min; Mass spectrum (ESI$^+$): m/z=467/469 (Br) [m+H]$^+$.

Example 33

N-Cyclopropyl-N-[1-(5-fluoro-pyridin-2-yl)-piperidin-4-yl]-4-oxazol-5-yl-benzamide

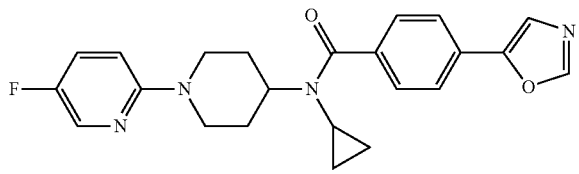 [SMILES: O=C(c1ccc(-c2cnco2)cc1)N(C1CC1)C1CCN(c2ccc(F)cn2)CC1]

The title compound is prepared from N-cyclopropyl-4-oxazol-5-yl-N-piperidin-4-yl-benzamide and 2-chloro-5-fluoro-pyridine following a procedure analogous to that described in Example 19. LC (method 5): $t_R$=1.79 min; Mass spectrum (ESI$^+$): m/z=407 [M+H]$^+$.

Example 34

N-Cyclopropyl-N-[1-(5-methyl-pyridin-2-yl)-piperidin-4-yl]-4-oxazol-5-yl-benzamide

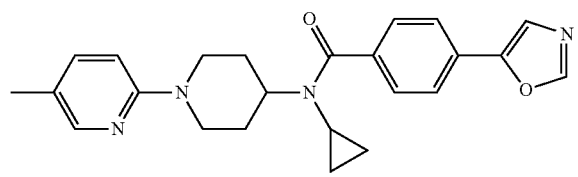 [SMILES: Cc1ccc(N2CCC(N(C(=O)c3ccc(-c4cnco4)cc3)C3CC3)CC2)nc1]

The title compound is prepared from N-cyclopropyl-4-oxazol-5-yl-N-piperidin-4-yl-benzamide and 2-fluoro-5-methyl-pyridine following a procedure analogous to that described in Example 19. LC (method 5): $t_R$=1.49 min; Mass spectrum (ESI$^+$): m/z=403 [M+H]$^+$.

Example 35

N-[1-(3-Chloro-[1,2,4]thiadiazol-5-yl)-piperidin-4-yl]-N-cyclopropyl-4-oxazol-5-yl-benzamide

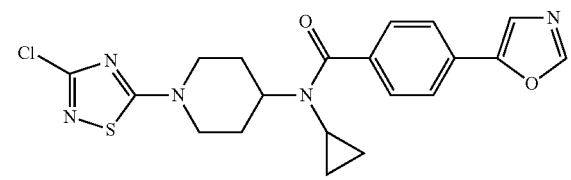 [SMILES: O=C(c1ccc(-c2cnco2)cc1)N(C1CC1)C1CCN(c2nc(Cl)ns2)CC1]

A mixture of N-cyclopropyl-4-oxazol-5-yl-N-piperidin-4-yl-benzamide hydrogen chloride salt (696 mg), 3,5-dichloro-1,2,4-thiadiazole (372 mg), and triethylamine (0.42 mL) in dichloromethane (30 mL) is stirred overnight at room temperature. More triethylamine (0.40 mL) is added and the mixture is stirred until the conversion is complete (1 h). The solvent is partly evaporated and the residue is triturated with water. The precipitate is filtered off, washed with dichloromethane and dried to yield the title compound. LC (method 5): $t_R$=2.08 min; Mass spectrum (ESI$^+$): m/z=430/432 (Cl) [m+H]$^+$.

Example 36

N-Cyclopropyl-N-[1-(3-isopropylamino-[1,2,4]thiadiazol-5-yl)-piperidin-4-yl]-4-oxazol-5-yl-benzamide

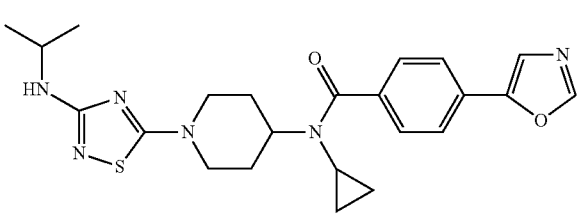 [SMILES: CC(C)Nc1nsc(N2CCC(N(C(=O)c3ccc(-c4cnco4)cc3)C3CC3)CC2)n1]

A mixture of N-[1-(3-chloro-[1,2,4]thiadiazol-5-yl)-piperidin-4-yl]-N-cyclopropyl-4-oxazol-5-yl-benzamide (43 mg) and isopropylamine (0.50 mL) in N-methyl-2-pyrrolidinon (1.50 mL) is stirred at 120° C. for two days. The mixture is concentrated in vacuo and the residue is purified by HPLC on reversed phase (MeOH/H$_2$O/NH$_4$OH). LC (method 5): $t_R$=1.95 min; Mass spectrum (ESI$^+$): m/z=453 [M+H]$^+$.

Example 37

N-Cyclopropyl-N-[1-(3-isopropoxy-[1,2,4]thiadiazol-5-yl)-piperidin-4-yl]-4-oxazol-5-yl-benzamide

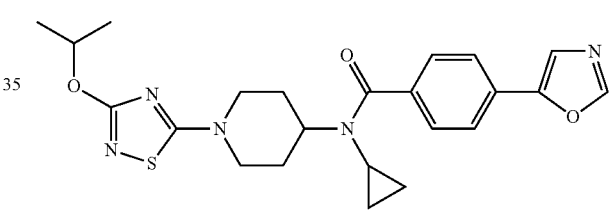

A mixture of N-[1-(3-chloro-[1,2,4]thiadiazol-5-yl)-piperidin-4-yl]-N-cyclopropyl-4-oxazol-5-yl-benzamide (43 mg), isopropanol (2.0 mL), and cesium carbonate (98 mg) in N-methyl-2-pyrrolidinon (2.0 mL) is stirred at 125° C. for three days. The mixture is separated by HPLC (MeOH/H$_2$O/TFA) to give the title compound. LC (method 5): $t_R$=2.14 min; Mass spectrum (ESI$^+$): m/z=454 [M+H]$^+$.

Example 38

Biphenyl-4,4'-dicarboxylic acid 4-amide 4'-{cyclopropyl-[1-(3-ethyl-[1,2,4]oxadiazol-5-yl)-piperidin-4-yl]-amide}

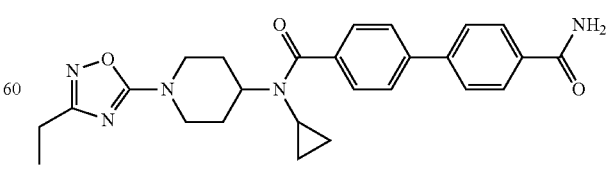

The title compound is prepared from biphenyl-4,4'-dicarboxylic acid 4-amide 4'-[(1-cyano-piperidin-4-yl)-cyclopropyl-amide] and N-hydroxy-propionamidine following a procedure analogous to that described in Example 1. LC (method 4): $t_R$=1.73 min; Mass spectrum (ESI$^+$): m/z=460 [M+H]$^+$.

Example 39

Biphenyl-4,4'-dicarboxylic acid 4'-amide 4-{cyclopropyl-[1-(3-phenyl-[1,2,4]oxadiazol-5-yl)-Piperidin-4-yl]-amide}

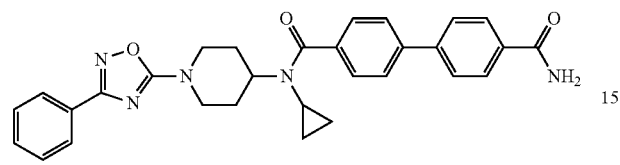

The title compound is prepared from biphenyl-4,4'-dicarboxylic acid 4-amide 4'-[(1-cyano-piperidin-4-yl)-cyclopropyl-amide] and N-hydroxy-benzamidine following a procedure analogous to that described in Example 1. LC (method 4): $t_R$=1.93 min; Mass spectrum (ESI$^+$): m/z=508 [M+H]$^+$.

Example 40

N-{1-[3-(4-Bromo-phenyl)-[1,2,4]oxadiazol-5-yl]-piperidin-4-yl}-N-cyclopropyl-4-oxazol-5-yl-benzamide

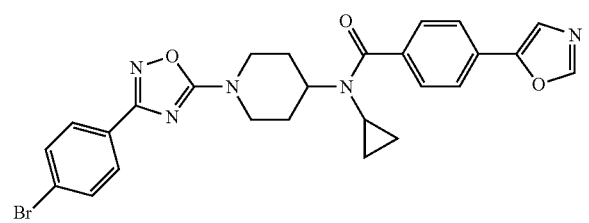 [SMILES: O=C(c1ccc(-c2cnco2)cc1)N(C1CC1)C1CCN(c2nc(-c3ccc(Br)cc3)no2)CC1]

The title compound is prepared from N-(1-cyano-piperidin-4-yl)-N-cyclopropyl-4-oxazol-5-yl-benzamide and 4-bromo-N-hydroxy-benzamidine following a procedure analogous to that described in Example 1. LC (method 6): $t_R$=2.08 min; Mass spectrum (ESI$^+$): m/z=534/536 (Br) [M+H]$^+$.

Example 41

N-Cyclopropyl-4-(4-methyl-oxazol-5-yl)-N-[1-(3-phenyl-[1,2,4]oxadiazol-5-yl)-piperidin-4-yl]-benzamide

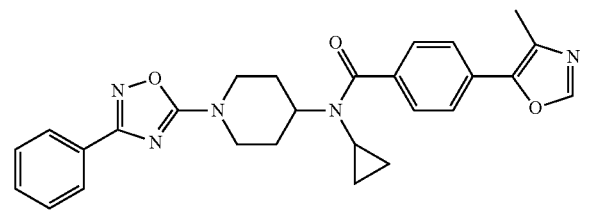 [SMILES: Cc1ncoc1-c1ccc(C(=O)N(C2CC2)C2CCN(c3nc(-c4ccccc4)no3)CC2)cc1]

The title compound is prepared from cyclopropyl-[1-(3-phenyl-[1,2,4]oxadiazol-5-yl)-piperidin-4-yl]-amine and 4-(4-methyl-oxazol-5-yl)-benzoic acid following a procedure analogous to that described in Example 17. LC (method 11): $t_R$=3.12 min; Mass spectrum (ESI$^+$): m/z=470 [M+H]$^+$.

Example 42

N-Cyclopropyl-N-[1-(3-isopropyl-[1,2,4]oxadiazol-5-yl)-piperidin-4-yl]-4-(4-methyl-oxazol-5-yl)-benzamide

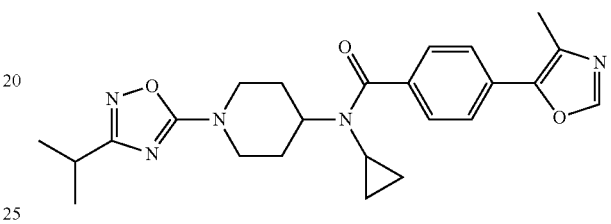

4-(4-Methyl-oxazol-5-yl)-benzoyl chloride (89 mg) is added portionwise to a mixture of cyclopropyl-[1-(3-isopropyl-[1,2,4]oxadiazol-5-yl)-piperidin-4-yl]-amine (100 mg) and ethyldiisopropylamine (100 µL) in dichloromethane (5 mL). The mixture is stirred for 1 h at room temperature, washed with water and 1 M HCl, dried over $Na_2SO_4$ and concentrated in vacuo. The residue is triturated with diethyl ether to give the title compound. LC (method 6): $t_R$=1.83 min; Mass spectrum (ESI$^+$): m/z=436 [M+H]$^+$.

Example 43

N-[1-(5-Chloro-pyrimidin-2-yl)-piperidin-4-yl]-N-cyclopropyl-4-(4-methyl-oxazol-5-yl)-benzamide

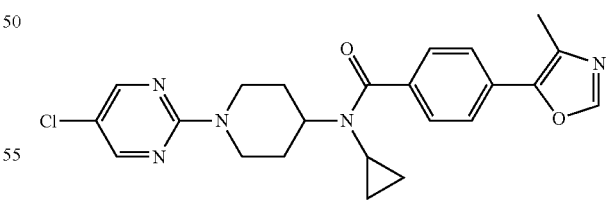

The title compound is prepared from N-cyclopropyl-4-(4-methyl-oxazol-5-yl)-N-piperidin-4-yl-benzamide trifluoroacetic acid salt and 2,5-dichloro-pyrimidine following a procedure analogous to that described in Example 19 using N-methylpyrrolidinone as solvent. LC (method 6): $t_R$=1.92 min; Mass spectrum (ESI$^+$): m/z=438/440 (Cl) [M+H]$^+$.

Example 44

N-Cyclopropyl-N-{1-[3-(4-methoxy-phenyl)-[1,2,4]oxadiazol-5-yl]-piperidin-4-yl}-4-oxazol-5-yl-benzamide

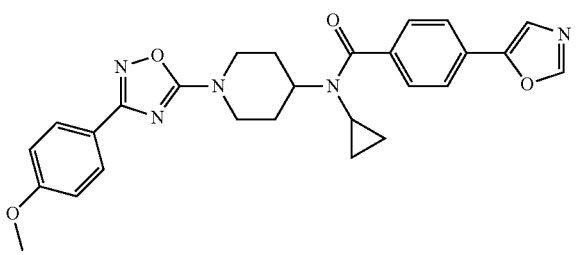 [SMILES: COc1ccc(-c2noc(N3CCC(N(C(=O)c4ccc(-c5cnco5)cc4)C4CC4)CC3)n2)cc1]

The title compound is prepared from N-cyclopropyl-4-oxazol-5-yl-N-piperidin-4-yl-benzamide and 5-chloro-3-(4-methoxy-phenyl)-[1,2,4]oxadiazole following a procedure analogous to that described in Example 19 using N-methylpyrrolidinone as solvent. LC (method 6): $t_R$=1.92 min; Mass spectrum (ESI$^+$): m/z=486 [M+H]$^+$.

Example 45

5-{4-[Cyclopropyl-(4-oxazol-5-yl-benzoyl)-amino]-piperidin-1-yl}-[1,2,4]oxadiazole-3-carboxylic acid ethyl ester

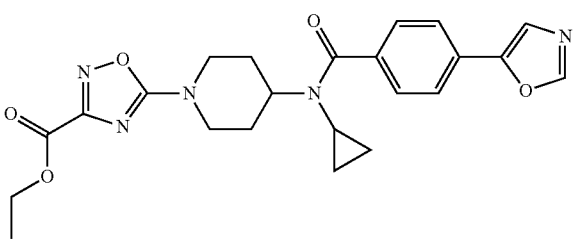 [SMILES: CCOC(=O)c1noc(N2CCC(N(C(=O)c3ccc(-c4cnco4)cc3)C3CC3)CC2)n1]

The title compound is prepared from N-(1-cyano-piperidin-4-yl)-N-cyclopropyl-4-oxazol-5-yl-benzamide and hydroxyamino-imino-acetic acid ethyl ester following a procedure analogous to that described in Example 1. LC (method 3): $t_R$=1.77 min; Mass spectrum (ESI$^+$): m/z=452 [M+H]$^+$.

Example 46

N-Cyclopropyl-N-{1-[3-(1-hydroxy-1-methyl-ethyl)-[1,2,4]oxadiazol-5-yl]-piperidin-4-yl}-4-oxazol-5-yl-benzamide

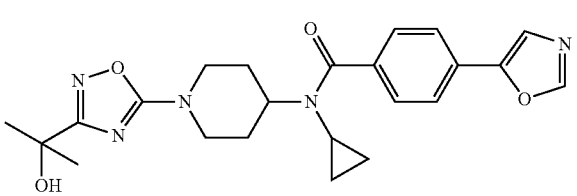 [SMILES: CC(C)(O)c1noc(N2CCC(N(C(=O)c3ccc(-c4cnco4)cc3)C3CC3)CC2)n1]

A 1.4 M solution of methyl magnesium bromide in toluene (1.20 mL) is added under argon atmosphere to a solution of 5-{4-[cyclopropyl-(4-oxazol-5-yl-benzoyl)-amino]-piperidin-1-yl}-[1,2,4]oxadiazole-3-carboxylic acid ethyl ester (230 mg) in tetrahydrofuran chilled in an ice bath and containing molecular sieves 3 Å (500 mg). The reaction mixture is stirred for 2 h at room temperature, quenched with aqueous NH$_4$Cl solution and extracted with dichloromethane. The organic phase is washed with brine and concentrated in vacuo. The residue is chromatographed on silica gel (dichloromethane/methanol 97:3) to afford the title compound. LC (method 12): $t_R$=1.23 min; Mass spectrum (ESI$^+$): m/z=438 [M+H]$^+$.

Example 47

N-Cyclopropyl-4-oxazol-5-yl-N-[1-(5-phenyl-[1,2,4]oxadiazol-3-yl)-piperidin-4-yl]-benzamide

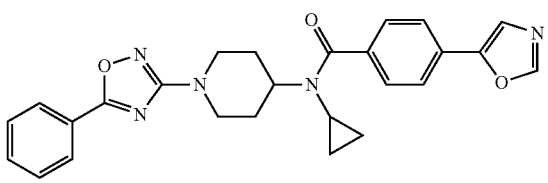

A mixture of N-cyclopropyl-N-[1-(N-hydroxycarbamimidoyl)-piperidin-4-yl]-4-oxazol-5-yl-benzamide (220 mg), benzoyl chloride (70 µL), and triethylamine (250 µL) in tetrahydrofuran (5 mL) is stirred for 30 min at room temperature before heating to 80° C. for 15 h. The solvent is evaporated and the residue is chromatographed on silica gel (dichloromethane/methanol 93:7) to afford the title compound. LC (method 3): $t_R$=2.09 min; Mass spectrum (ESI$^+$): m/z=456 [M+H]$^+$.

Example 48

N-Cyclopropyl-N-[1-(5-ethyl-[1,2,4]oxadiazol-3-yl)-piperidin-4-yl]-4-oxazol-5-yl-benzamide

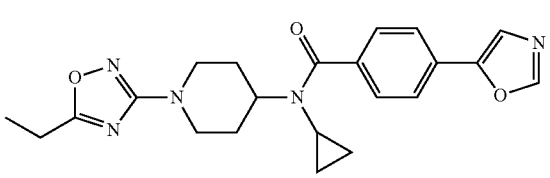 [SMILES: CCc1nc(N2CCC(N(C(=O)c3ccc(-c4cnco4)cc3)C3CC3)CC2)no1]

The title compound is prepared from N-cyclopropyl-N-[1-(N-hydroxycarbamimidoyl)-piperidin-4-yl]-4-oxazol-5-yl-benzamide and propionyl chloride following a procedure analogous to that described in Example 47. LC (method 3): $t_R$=1.83 min; Mass spectrum (ESI$^+$): m/z=408 [M+H]$^+$.

Example 49

N-Cyclopropyl-N-[1-(5-isopropyl-[1,2,4]oxadiazol-3-yl)-piperidin-4-yl]-4-oxazol-5-yl-benzamide

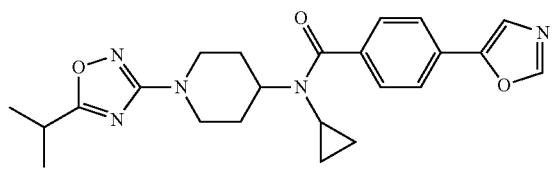 [SMILES: CC(C)c1nc(N2CCC(N(C(=O)c3ccc(-c4cnco4)cc3)C3CC3)CC2)no1]

The title compound is prepared from N-cyclopropyl-N-[1-(N-hydroxycarbamimidoyl)-piperidin-4-yl]-4-oxazol-5-yl-benzamide and propionyl chloride following a procedure analogous to that described in Example 47. LC (method 3): $t_R$=1.92 min; Mass spectrum (ESI$^+$): m/z=422 [M+H]$^+$.

Example 50

N-Cyclopropyl-4-oxazol-5-yl-N-[1-(5-pyrazin-2-yl-[1,2,4]oxadiazol-3-yl)-piperidin-4-yl]-benzamide

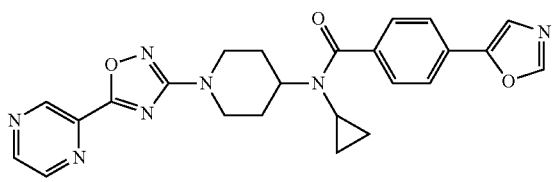 [SMILES: O=C(c1ccc(-c2cnco2)cc1)N(C1CC1)C1CCN(c2noc(-c3cnccn3)n2)CC1]

The title compound is prepared from N-cyclopropyl-N-[1-(N-hydroxycarbamimidoyl)-piperidin-4-yl]-4-oxazol-5-yl-benzamide and pyrazine-2-carbonyl chloride following a procedure analogous to that described in Example 47. LC (method 2): $t_R$=1.15 min; Mass spectrum (ESI$^+$): m/z=458 [M+H]$^+$.

Example 51

N-Cyclopropyl-N-[1-(5-cyclopropyl-[1,2,4]oxadiazol-3-yl)-piperidin-4-yl]-4-oxazol-5-yl-benzamide

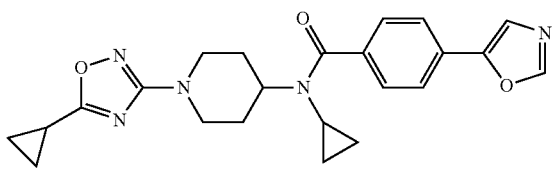 [SMILES: O=C(c1ccc(-c2cnco2)cc1)N(C1CC1)C1CCN(c2noc(C3CC3)n2)CC1]

The title compound is prepared from N-cyclopropyl-N-[1-(N-hydroxycarbamimidoyl)-piperidin-4-yl]-4-oxazol-5-yl-benzamide and cyclopropanecarbonyl chloride following a procedure analogous to that described in Example 47. LC (method 2): $t_R$=1.20 min; Mass spectrum (ESI$^+$): m/z=420 [M+H]$^+$.

Example 52

N-[1-(5-Cyclobutyl-[1,2,4]oxadiazol-3-yl)-piperidin-4-yl]-N-cyclopropyl-4-oxazol-5-yl-benzamide

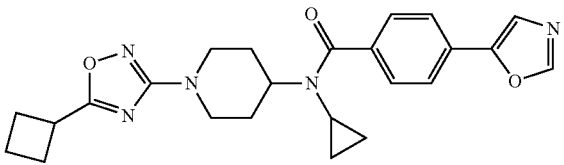 [SMILES: O=C(c1ccc(-c2cnco2)cc1)N(C1CC1)C1CCN(c2noc(C3CCC3)n2)CC1]

The title compound is prepared from N-cyclopropyl-N-[1-(N-hydroxycarbamimidoyl)-piperidin-4-yl]-4-oxazol-5-yl-benzamide and cyclobutanecarbonyl chloride following a procedure analogous to that described in Example 47. LC (method 2): $t_R$=1.27 min; Mass spectrum (ESI$^+$): m/z=434 [M+H]$^+$.

Example 53

N-Cyclopropyl-N-[1-(5-ethyl-pyrimidin-2-yl)-3-methyl-piperidin-4-yl]-4-oxazol-5-yl-benzamide

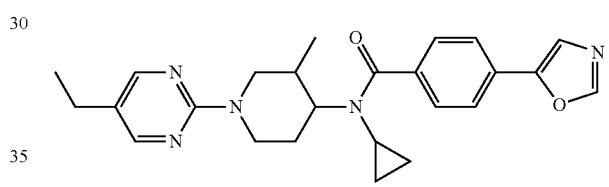

The title compound is prepared from N-cyclopropyl-N-(3-methyl-piperidin-4-yl)-4-oxazol-5-yl-benzamide and 2-chloro-5-ethyl-pyrimidine following a procedure analogous to that described in Example 19 using N-methylpyrrolidinone as solvent. LC (method 3): $t_R$=1.83 min; Mass spectrum (ESI$^+$): m/z=432 [M+H]$^+$.

Example 54

N-Cyclopropyl-N-[3-methyl-1-(3-phenyl-[1,2,4]oxadiazol-5-yl)-piperidin-4-yl]-4-oxazol-5-yl-benzamide

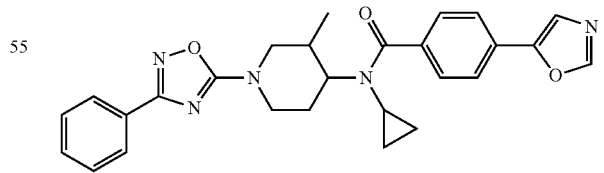

The title compound is prepared from N-cyclopropyl-N-(3-methyl-piperidin-4-yl)-4-oxazol-5-yl-benzamide and 5-chloro-3-phenyl-[1,2,4]oxadiazole following a procedure analogous to that described in Example 19 using N-methylpyrrolidinone as solvent. LC (method 3): $t_R$=2.01 min; Mass spectrum (ESI$^+$): m/z=470 [M+H]$^+$.

Example 55

N-Cyclopropyl-4-oxazol-5-yl-N-{1-[3-(tetrahydro-pyran-4-ylmethyl)-[1,2,4]oxadiazol-5-yl]-piperidin-4-yl}-benzamide

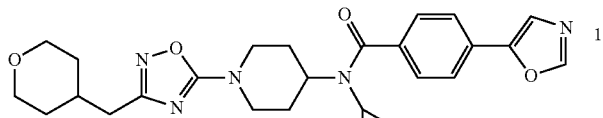

The title compound is prepared from N-(1-cyano-piperidin-4-yl)-N-cyclopropyl-4-oxazol-5-yl-benzamide and N-hydroxy-2-(tetrahydro-pyran-4-yl)-acetamidine following a procedure analogous to that described in Example 1. LC (method 1): $t_R$=1.13 min; Mass spectrum (ESI$^+$): m/z=478 [M+H]$^+$.

Example 56

N-Cyclopropyl-4-oxazol-5-yl-N-{1-[3-(tetrahydro-pyran-4-yl)-[1,2,4]oxadiazol-5-yl]-piperidin-4-yl}-benzamide

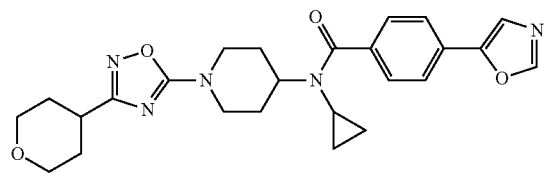 [SMILES: O=C(c1ccc(-c2cnco2)cc1)N(C1CC1)C1CCN(c2nc(C3CCOCC3)no2)CC1]

The title compound is prepared from N-(1-cyano-piperidin-4-yl)-N-cyclopropyl-4-oxazol-5-yl-benzamide and N-hydroxy-tetrahydro-pyran-4-carboxamidine following a procedure analogous to that described in Example 1. LC (method 1): $t_R$=1.10 min; Mass spectrum (ESI$^+$): m/z=464 [M+H]$^+$.

Example 57

N-[1-(3-But-3-enyl-[1,2,4]oxadiazol-5-yl)-piperidin-4-yl]-N-cyclopropyl-4-oxazol-5-yl-benzamide

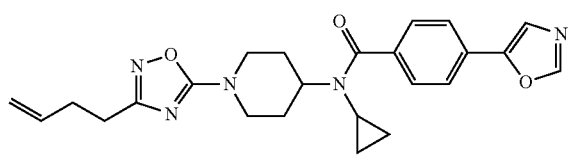 [SMILES: C=CCCc1noc(N2CCC(N(C(=O)c3ccc(-c4cnco4)cc3)C3CC3)CC2)n1]

The title compound is prepared from N-(1-cyano-piperidin-4-yl)-N-cyclopropyl-4-oxazol-5-yl-benzamide and N-hydroxy-pent-4-enamidine following a procedure analogous to that described in Example 1. LC (method 1): $t_R$=1.19 min; Mass spectrum (ESI$^+$): m/z=434 [M+H]$^+$.

Example 58

N-Cyclopropyl-N-{1-[3-(2-hydroxy-1,1-dimethyl-ethyl)-[1,2,4]oxadiazol-5-yl]-piperidin-4-yl}-4-oxazol-5-yl-benzamide

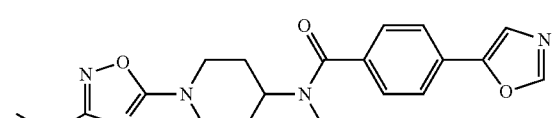

The title compound is prepared from N-(1-cyano-piperidin-4-yl)-N-cyclopropyl-4-oxazol-5-yl-benzamide and 3,N-dihydroxy-2,2-dimethyl-propionamidine following a procedure analogous to that described in Example 1. LC (method 1): $t_R$=1.08 min; Mass spectrum (ESI$^+$): m/z=452 [M+H]$^+$.

Example 59

N-Cyclopropyl-4-oxazol-5-yl-N-[1-(5-propyl-[1,2,4]oxadiazol-3-yl)-piperidin-4-yl]-benzamide

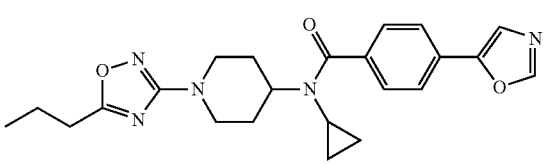 [SMILES: CCCc1nc(N2CCC(N(C(=O)c3ccc(-c4cnco4)cc3)C3CC3)CC2)no1]

The title compound is prepared from N-cyclopropyl-N-[1-(N-hydroxycarbamimidoyl)-piperidin-4-yl]-4-oxazol-5-yl-benzamide and butyryl chloride following a procedure analogous to that described in Example 47. LC (method 8): $t_R$=1.33 min; Mass spectrum (ESI$^+$): m/z=422 [M+H]$^+$.

Example 60

N-Cyclopropyl-4-oxazol-5-yl-N-{1-[3-(3,3,3-trifluoro-propyl)-[1,2,4]oxadiazol-5-yl]-piperidin-4-yl}-benzamide

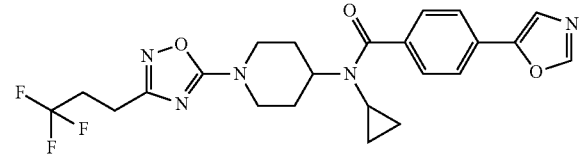 [SMILES: O=C(c1ccc(-c2cnco2)cc1)N(C1CC1)C1CCN(c2nc(CCC(F)(F)F)no2)CC1]

The title compound is prepared from N-(1-cyano-piperidin-4-yl)-N-cyclopropyl-4-oxazol-5-yl-benzamide and 4,4,4-trifluoro-N-hydroxy-butyramidine following a procedure analogous to that described in Example 1. LC (method 8): $t_R$=1.30 min; Mass spectrum (ESI$^+$): m/z=476 [M+H]$^+$.

Example 61

N-Cyclopropyl-N-[1-(5-methyl-pyrazin-2-yl)-piperidin-4-yl]-4-oxazol-5-yl-benzamide

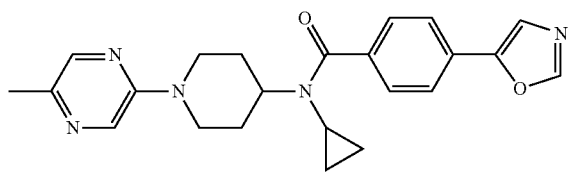

A mixture of N-cyclopropyl-4-oxazol-5-yl-N-piperidin-4-yl-benzamide (600 mg), 2-chloro-5-methyl-pyrazine (100 mg), and cesium carbonate (300 mg) in N,N-dimethylformamide (10 mL) is stirred for 3 days at 80° C. After cooling to room temperature ethyl acetate and water are added. The organic phase is separated, washed with water and brine, dried over MgSO$_4$, and concentrated in vacuo. The residue is chromatographed on silica gel (ethyl acetate/methanol 7:3) to give the title compound. LC (method 1): $t_R$=1.08 min; Mass spectrum (ESI$^+$): m/z=404 [M+H]$^+$.

Example 62

N-Cyclopropyl-4-oxazol-5-yl-N-{1-[3-(2,2,2-trifluoro-ethyl)-[1,2,4]oxadiazol-5-yl]-piperidin-4-yl}benzamide

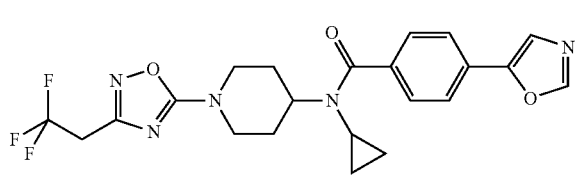 [SMILES: O=C(c1ccc(-c2cnco2)cc1)N(C1CC1)C1CCN(c2nc(CC(F)(F)F)no2)CC1]

The title compound is prepared from N-(1-cyano-piperidin-4-yl)-N-cyclopropyl-4-oxazol-5-yl-benzamide 3,3,3-trifluoro-N-hydroxy-propionamidine following a procedure analogous to that described in Example 1. LC (method 13): $t_R$=1.31 min; Mass spectrum (ESI$^+$): m/z=462 [M+H]$^+$.

Example 63

N-Cyclopropyl-N-[1-(5-ethyl-pyrimidin-2-yl)-piperidin-4-yl]-3-fluoro-4-oxazol-5-yl-benzamide

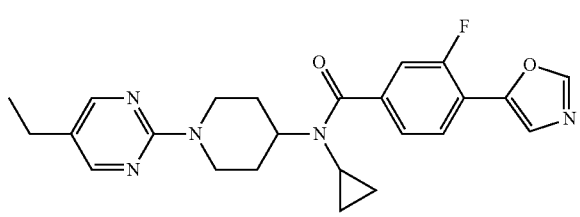 [SMILES: CCc1cnc(N2CCC(N(C(=O)c3ccc(-c4cnco4)c(F)c3)C3CC3)CC2)nc1]

The title compound is prepared from N-cyclopropyl-3-fluoro-4-oxazol-5-yl-N-piperidin-4-yl-benzamide and 2-chloro-5-ethyl-pyrimidine following a procedure analogous to that described in Example 19. LC (method 1): $t_R$=1.16 min; Mass spectrum (ESI$^+$): m/z=436 [M+H]$^+$.

Example 64

N-Cyclopropyl-3-fluoro-N-[1-(3-isopropyl-[1,2,4]oxadiazol-5-yl)-piperidin-4-yl]-4-oxazol-5-yl-benzamide

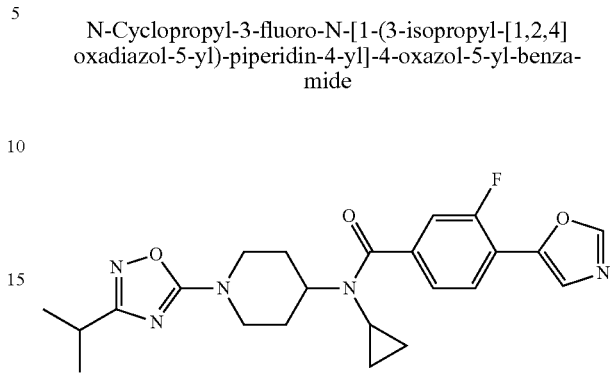

The title compound is prepared from cyclopropyl-[1-(3-isopropyl-[1,2,4]oxadiazol-5-yl)-piperidin-4-yl]-amine and 3-fluoro-4-oxazol-5-yl-benzoic acid following a procedure analogous to that described in Example 17. LC (method 1): $t_R$=1.20 min; Mass spectrum (ESI$^+$): m/z=440 [M+H]$^+$.

Example 65

N-Cyclopropyl-3-fluoro-4-oxazol-5-yl-N-[1-(3-propyl-[1,2,4]oxadiazol-5-yl)-piperidin-4-yl]-benzamide

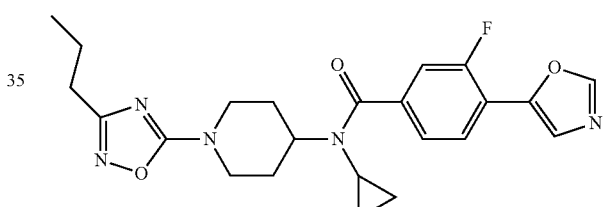

The title compound is prepared from cyclopropyl-[1-(3-propyl-[1,2,4]oxadiazol-5-yl)-piperidin-4-yl]-amine hydrochloride and 3-fluoro-4-oxazol-5-yl-benzoic acid following a procedure analogous to that described in Example 17. LC (method 1): $t_R$=1.20 min; Mass spectrum (ESI$^+$): m/z=440 [M+H]$^+$.

Example 66

N-Cyclopropyl-3-fluoro-N-[1-(5-methyl-pyrazin-2-yl)-piperidin-4-yl]-4-oxazol-5-yl-benzamide

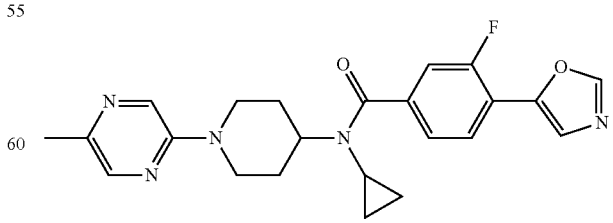

The title compound is prepared from cyclopropyl-[1-(5-methyl-pyrazin-2-yl)-piperidin-4-yl]-amine and 3-fluoro-4-oxazol-5-yl-benzoic acid following a procedure analogous to

Example 67

N-[1-(3-tert-Butyl-[1,2,4]oxadiazol-5-yl)-piperidin-4-yl]-N-cyclopropyl-3-fluoro-4-oxazol-5-yl-benzamide

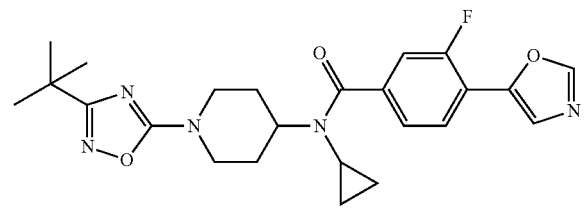 [SMILES: CC(C)(C)c1noc(N2CCC(N(C(=O)c3ccc(-c4cnco4)c(F)c3)C3CC3)CC2)n1]

The title compound is prepared from [1-(3-tert-butyl-[1,2,4]oxadiazol-5-yl)-piperidin-4-yl]-cyclopropyl-amine and 3-fluoro-4-oxazol-5-yl-benzoic acid following a procedure analogous to that described in Example 17. LC (method 1): $t_R$=1.26 min; Mass spectrum (ESI$^+$): m/z=454 [M+H]$^+$.

Example 68

N-Cyclopropyl-N-[1-(5-ethyl-pyrazin-2-yl)-piperidin-4-yl]-3-fluoro-4-oxazol-5-yl-benzamide

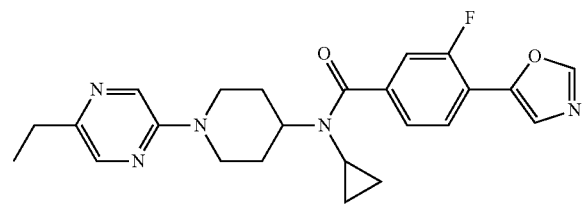 [SMILES: CCc1cnc(N2CCC(N(C(=O)c3ccc(-c4cnco4)c(F)c3)C3CC3)CC2)cn1]

The title compound is prepared from cyclopropyl-[1-(5-ethyl-pyrazin-2-yl)-piperidin-4-yl]-amine and 3-fluoro-4-oxazol-5-yl-benzoic acid following a procedure analogous to that described in Example 17. LC (method 1): $t_R$=1.18 min; Mass spectrum (ESI$^+$): m/z=436 [M+H]$^+$.

Example 69

N-Cyclopropyl-3,5-difluoro-N-[1-(3-isopropyl-[1,2,4]oxadiazol-5-yl)-piperidin-4-yl]-4-oxazol-5-yl-benzamide

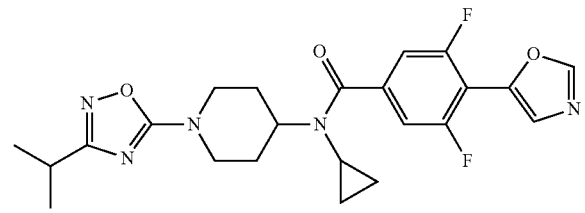

The title compound is prepared from cyclopropyl-[1-(3-isopropyl-[1,2,4]oxadiazol-5-yl)-piperidin-4-yl]-amine and 3,5-difluoro-4-oxazol-5-yl-benzoic acid following a procedure analogous to that described in Example 17. LC (method 1): $t_R$=1.19 min; Mass spectrum (ESI$^+$): m/z=458 [M+H]$^+$.

Example 70

N-Cyclopropyl-3-fluoro-N-[1-(5-methyl-pyrimidin-2-yl)-piperidin-4-yl]-4-oxazol-5-yl-benzamide

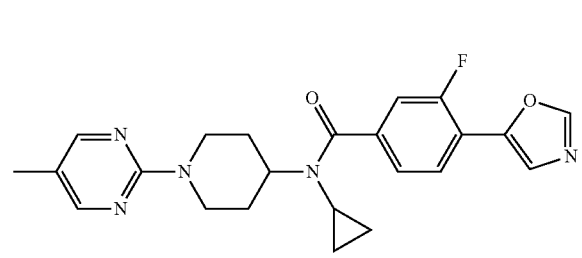 [SMILES: Cc1cnc(N2CCC(N(C(=O)c3ccc(-c4cnco4)c(F)c3)C3CC3)CC2)nc1]

The title compound is prepared from cyclopropyl-[1-(5-methyl-pyrimidin-2-yl)-piperidin-4-yl]-amine and 3-fluoro-4-oxazol-5-yl-benzoic acid following a procedure analogous to that described in Example 17. LC (method 1): $t_R$=1.10 min; Mass spectrum (ESI$^+$): m/z=422 [M+H]$^+$.

Example 71

N-(5'-Bromo-3'-fluoro-3,4,5,6-tetrahydro-2H-[1,2']bipyridinyl-4-yl)-N-cyclopropyl-4-oxazol-5-yl-benzamide

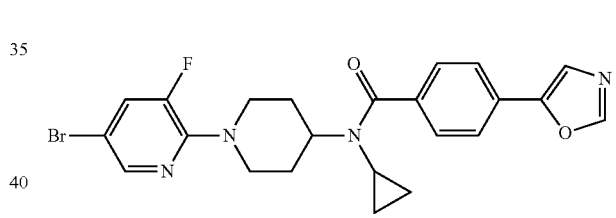

The title compound is prepared from N-Cyclopropyl-4-oxazol-5-yl-N-piperidin-4-yl-benzamide and 5-bromo-2,3-difluoro-pyridine following a procedure analogous to that described in Example 61 using K$_2$CO$_3$ as base and N-methylpyrrolidinone as solvent. LC (method 1): $t_R$=1.35 min; Mass spectrum (ESI$^+$): m/z=507 [M+Na]$^+$.

Example 72

N-Cyclopropyl-N-[1-(6-cyclopropyl-pyridazin-3-yl)-piperidin-4-yl]-4-oxazol-5-yl-benzamide

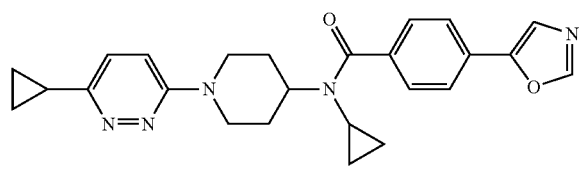 [SMILES: O=C(c1ccc(-c2cnco2)cc1)N(C1CC1)C1CCN(c2ccc(C3CC3)nn2)CC1]

The title compound is prepared by reacting N-cyclopropyl-4-oxazol-5-yl-N-piperidin-4-yl-benzamide and 3-chloro-6-cyclopropyl-pyridazine in the presence of K$_2$CO$_3$ in N-meth-

Example 73

N-Cyclopropyl-N-(3'-fluoro-5'-methyl-3,4,5,6-tetrahydro-2H-[1,2']bipyridinyl-4-yl)-4-oxazol-5-yl-benzamide

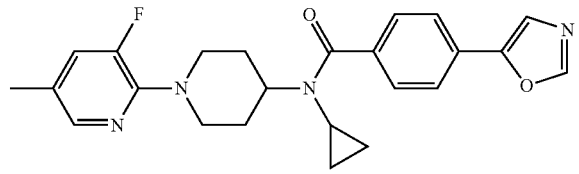 [SMILES: Cc1cnc(N2CCC(N(C(=O)c3ccc(-c4cnco4)cc3)C3CC3)CC2)c(F)c1]

A mixture of N-(5'-Bromo-3'-fluoro-3,4,5,6-tetrahydro-2H-[1,2']bipyridinyl-4-yl)-N-cyclopropyl-4-oxazol-5-yl-benzamide (170 mg), methylboronic acid (126 mg), Na$_2$CO$_3$ solution (2 M; 385 µL), and Pd(PPh)$_4$ (20 mg) in dioxane (3 mL) is stirred at 80° C. overnight under an argon atmosphere. Three more portions of methylboronic acid (42 mg each) as well as PdCl$_2$[1,1'-bis(diphenylphosphino)-ferrocene]*CH$_2$Cl$_2$ complex (14 mg) are added successively over the next day until the conversion is complete. The reaction mixture is filtered through a pad of aluminium oxide and washed with dioxane. The filtrate is concentrated in vacuo and the residue is purified by preparative HPLC. LC (method 1): t$_R$=1.15 min; Mass spectrum (ESI$^+$): m/z=421 [M+H]$^+$.

Example 74

N-Cyclopropyl-N-(3'-fluoro-5'-trifluoromethyl-3,4,5,6-tetrahydro-2H-[1,2']bipyridinyl-4-yl)-4-oxazol-5-yl-benzamide

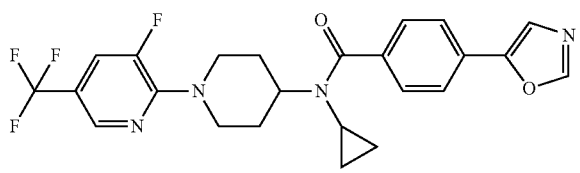 [SMILES: O=C(c1ccc(-c2cnco2)cc1)N(C1CC1)C1CCN(c2ncc(C(F)(F)F)cc2F)CC1]

The title compound is prepared from N-cyclopropyl-4-oxazol-5-yl-N-piperidin-4-yl-benzamide hydrochloride and 2,3-difluoro-5-trifluoromethyl-pyridine following a procedure analogous to that described in Example 19 using N-methylpyrrolidinone as solvent. LC (method 16): t$_R$=0.56 min; Mass spectrum (ESI$^+$): m/z=475 [M+H]$^+$.

ylpyrrolidinone at 200° C. in a microwave vessel. LC (method 15): t$_R$=1.26 min; Mass spectrum (ESI$^+$): m/z=430 [M+H]$^+$.

Example 75

N-Cyclopropyl-4-oxazol-5-yl-N-[1-(5-propoxy-pyrimidin-2-yl)-piperidin-4-yl]-benzamide

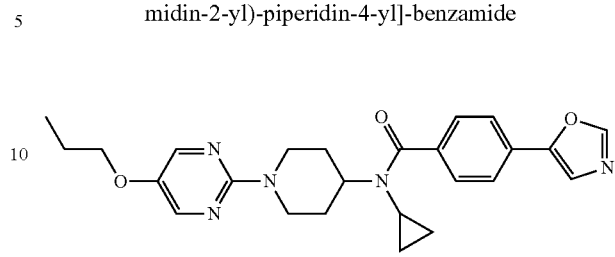

The title compound is prepared from N-cyclopropyl-4-oxazol-5-yl-N-piperidin-4-yl-benzamide hydrochloride and 2-chloro-5-propoxy-pyrimidine following a procedure analogous to that described in Example 19 using N-methylpyrrolidinone as solvent. LC (method 16): t$_R$=0.49 min; Mass spectrum (ESI$^+$): m/z=448 [M+H]$^+$.

Example 76

N-Cyclopropyl-N-[1-(5-ethoxy-pyrimidin-2-yl)-piperidin-4-yl]-4-oxazol-5-yl-benzamide

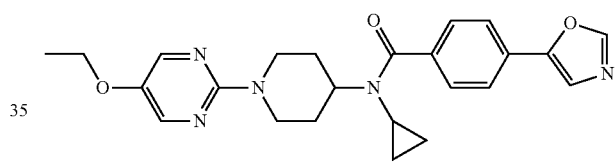

The title compound is prepared from N-cyclopropyl-4-oxazol-5-yl-N-piperidin-4-yl-benzamide hydrochloride and 2-chloro-5-ethoxy-pyrimidine following a procedure analogous to that described in Example 19 using N-methylpyrrolidinone as solvent. LC (method 16): t$_R$=0.46 min; Mass spectrum (ESI$^+$): m/z=434 [M+H]$^+$.

Example 77

N-Cyclopropyl-N-[1-(5-isopropoxy-pyrimidin-2-yl)-piperidin-4-yl]-4-oxazol-5-yl-benzamide

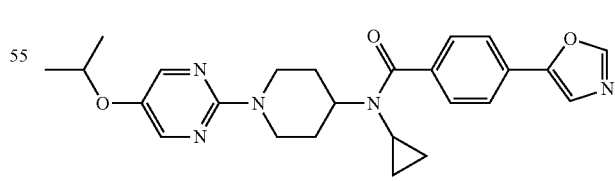

The title compound is prepared from N-cyclopropyl-4-oxazol-5-yl-N-piperidin-4-yl-benzamide hydrochloride and 2-chloro-5-isopropoxy-pyrimidine following a procedure analogous to that described in Example 19 using N-methylpyrrolidinone as solvent. LC (method 16): t$_R$=0.48 min; Mass spectrum (ESI$^+$): m/z=448 [M+H]$^+$.

Example 78

N-Cyclopropyl-N-[1-(5-cyclopropyl-pyrazin-2-yl)-piperidin-4-yl]-4-oxazol-5-yl-benzamide

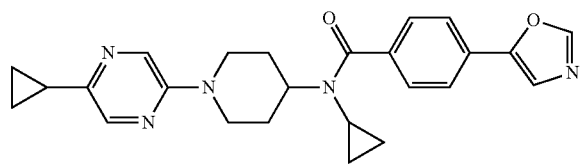 [SMILES: O=C(c1ccc(-c2cnco2)cc1)N(C1CC1)C1CCN(c2cnc(C3CC3)cn2)CC1]

The title compound is prepared from N-cyclopropyl-4-oxazol-5-yl-N-piperidin-4-yl-benzamide hydrochloride and 2-bromo-5-cyclopropyl-pyrazine following a procedure analogous to that described in Example 19 using N-methylpyrrolidinone as solvent. LC (method 16): $t_R$=0.46 min; Mass spectrum (ESI$^+$): m/z=430 [M+H]$^+$.

Example 79

N-Cyclopropyl-4-oxazol-5-yl-N-[1-(5-phenyl-[1,3,4]thiadiazol-2-yl)-piperidin-4-yl]-benzamide

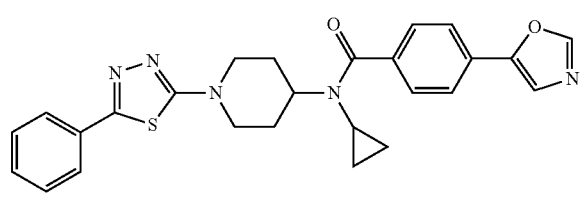 [SMILES: O=C(c1ccc(-c2cnco2)cc1)N(C1CC1)C1CCN(c2nnc(-c3ccccc3)s2)CC1]

The title compound is prepared from N-cyclopropyl-4-oxazol-5-yl-N-piperidin-4-yl-benzamide hydrochloride and 2-chloro-5-phenyl-[1,3,4]thiadiazole following a procedure analogous to that described in Example 19 using N-methylpyrrolidinone as solvent. LC (method 16): $t_R$=0.49 min; Mass spectrum (ESI$^+$): m/z=472 [M+H]$^+$.

Example 80

N-(5'-Chloro-3,4,5,6-tetrahydro-2H-[1,2']bipyridinyl-4-yl)-N-cyclopropyl-4-oxazol-5-yl-benzamide

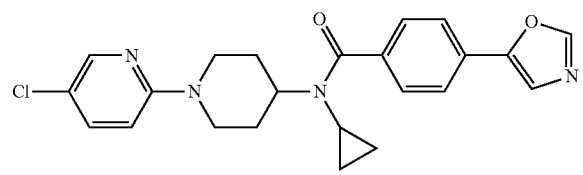 [SMILES: O=C(c1ccc(-c2cnco2)cc1)N(C1CC1)C1CCN(c2ccc(Cl)cn2)CC1]

The title compound is prepared from N-cyclopropyl-4-oxazol-5-yl-N-piperidin-4-yl-benzamide hydrochloride and 2,5-dichloro-pyridine following a procedure analogous to that described in Example 19 using N-methylpyrrolidinone as solvent. LC (method 16): $t_R$=0.43 min; Mass spectrum (ESI$^+$): m/z=423 [M+H]$^+$.

Example 81

5-{4-[Cyclopropyl-(4-oxazol-5-yl-benzoyl)-amino]-piperidin-1-yl}-pyrazine-2-carboxylic acid methyl ester

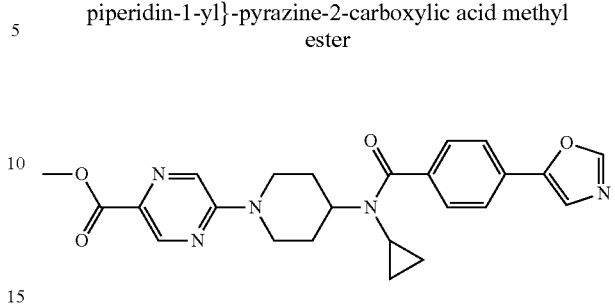

The title compound is prepared from N-cyclopropyl-4-oxazol-5-yl-N-piperidin-4-yl-benzamide hydrochloride and 5-chloro-pyrazine-2-carboxylic acid methyl ester following a procedure analogous to that described in Example 19 using N-methylpyrrolidinone as solvent. LC (method 16): $t_R$=0.44 min; Mass spectrum (ESI$^+$): m/z=448 [M+H]$^+$.

Example 82

N-Cyclopropyl-N-[1-(3,6-dimethyl-pyrazin-2-yl)-piperidin-4-yl]-4-oxazol-5-yl-benzamide

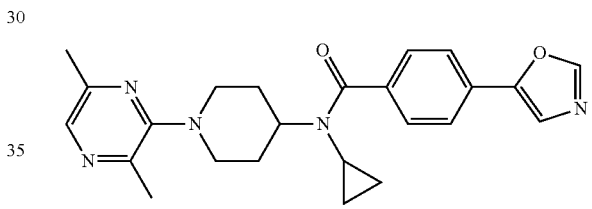

The title compound is prepared from N-cyclopropyl-4-oxazol-5-yl-N-piperidin-4-yl-benzamide hydrochloride and 3-chloro-2,5-dimethyl-pyrazine following a procedure analogous to that described in Example 19 using N-methylpyrrolidinone as solvent. LC (method 16): $t_R$=0.44 min; Mass spectrum (ESI$^+$): m/z=418 [M+H]$^+$.

Example 83

N-Cyclopropyl-N-[1-(5-iodo-pyrazin-2-yl)-piperidin-4-yl]-4-oxazol-5-yl-benzamide

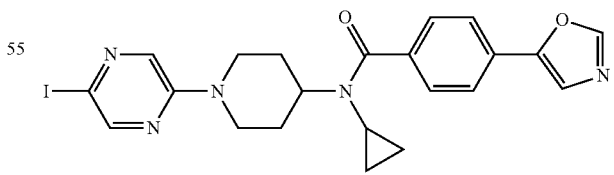

The title compound is prepared from N-cyclopropyl-4-oxazol-5-yl-N-piperidin-4-yl-benzamide hydrochloride and 2-bromo-5-iodo-pyrazine following a procedure analogous to that described in Example 19 using N-methylpyrrolidinone as solvent. LC (method 16): $t_R$=0.51 min; Mass spectrum (ESI$^+$): m/z=516 [M+H]$^+$.

Example 84

2-{4-[Cyclopropyl-(4-oxazol-5-yl-benzoyl)-amino]-piperidin-1-yl}-pyrimidine-5-carboxylic acid methyl ester

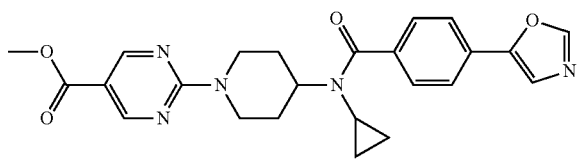 [SMILES: COC(=O)c1cnc(N2CCC(N(C(=O)c3ccc(-c4cnco4)cc3)C3CC3)CC2)nc1]

The title compound is prepared from N-cyclopropyl-4-oxazol-5-yl-N-piperidin-4-yl-benzamide hydrochloride and 2-chloro-pyrimidine-5-carboxylic acid methyl ester following a procedure analogous to that described in Example 19 using N-methylpyrrolidinone as solvent. LC (method 16): $t_R$=0.48 min; Mass spectrum (ESI$^+$): m/z=448 [M+H]$^+$.

Example 85

N-Cyclopropyl-4-oxazol-5-yl-N-(1-pyrazin-2-yl-piperidin-4-yl)-benzamide

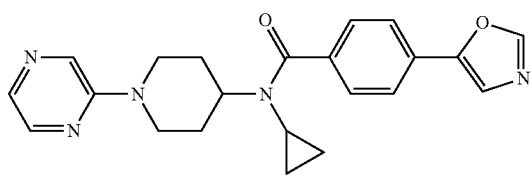 [SMILES: O=C(c1ccc(-c2cnco2)cc1)N(C1CC1)C1CCN(c2cnccn2)CC1]

The title compound is prepared from N-cyclopropyl-4-oxazol-5-yl-N-piperidin-4-yl-benzamide hydrochloride and 2-fluoro-pyrazine following a procedure analogous to that described in Example 19 using N-methylpyrrolidinone as solvent. LC (method 16): $t_R$=0.43 min; Mass spectrum (ESI$^+$): m/z=390 [M+H]$^+$.

Example 86

N-[1-(5-Cyano-pyrazin-2-yl)-piperidin-4-yl]-N-cyclopropyl-4-oxazol-5-yl-benzamide

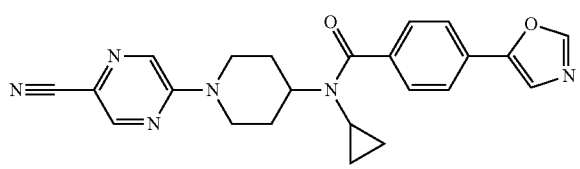 [SMILES: N#Cc1cnc(N2CCC(N(C(=O)c3ccc(-c4cnco4)cc3)C3CC3)CC2)cn1]

The title compound is prepared from N-cyclopropyl-4-oxazol-5-yl-N-piperidin-4-yl-benzamide hydrochloride and 5-chloro-pyrazine-2-carbonitrile following a procedure analogous to that described in Example 19 using N-methylpyrrolidinone as solvent. LC (method 16): $t_R$=0.46 min; Mass spectrum (ESI$^+$): m/z=415 [M+H]$^+$.

Example 87

N-Cyclopropyl-4-oxazol-5-yl-N-[1-(5-trifluoromethyl-[1,3,4]thiadiazol-2-yl)-piperidin-4-yl]-benzamide

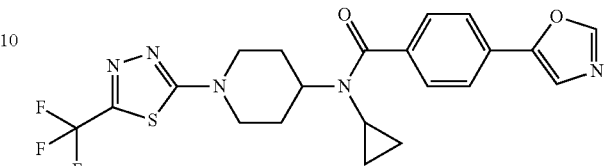

The title compound is prepared from N-cyclopropyl-4-oxazol-5-yl-N-piperidin-4-yl-benzamide hydrochloride and 2-chloro-5-trifluoromethyl-[1,3,4]thiadiazole following a procedure analogous to that described in Example 19 using N-methylpyrrolidinone as solvent. LC (method 17): $t_R$=1.42 min; Mass spectrum (ESI$^+$): m/z=464 [M+H]$^+$.

Example 88

N-Cyclopropyl-N-[1-(5-cyclopropyl-pyrimidin-2-yl)-piperidin-4-yl]-4-oxazol-5-yl-benzamide

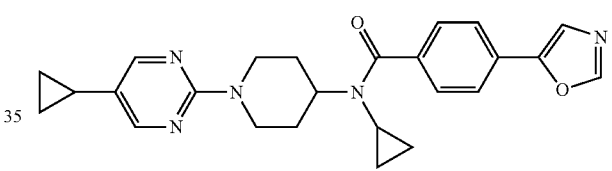

A mixture of N-cyclopropyl-4-oxazol-5-yl-N-piperidin-4-yl-benzamide hydrochloride (35 mg), 2-chloro-5-cyclopropyl-pyrimidine (46 mg), and 2-tert-butylimino-2-diethylamino-1,3-dimethyl-perhydro-1,3,2-diazaphosphorine (82 mg) in N-methylpyrrolidinone (1.5 mol) is stirred at 70° C. overnight. The crude product is purified by preparative HPLC to give the title compound. LC (method 18): $t_R$=1.41 min; Mass spectrum (ESI$^+$): m/z=430 [M+H]$^+$.

Example 89

N-Cyclopropyl-N-[1-(5-methyl-pyrimidin-2-yl)-piperidin-4-yl]-4-oxazol-5-yl-benzamide

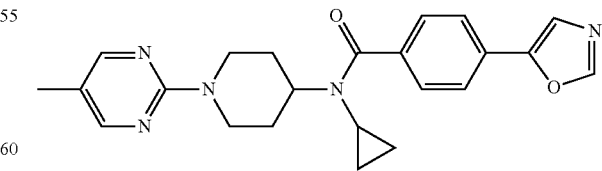 [SMILES: O=C(c1ccc(-c2cnco2)cc1)N(C1CC1)C1CCN(c2ncc(C3CC3)cn2)CC1]

The title compound is prepared from N-cyclopropyl-4-oxazol-5-yl-N-piperidin-4-yl-benzamide hydrochloride and 2-chloro-5-methyl-pyrimidine following a procedure analogous to that described in Example 88. LC (method 18): $t_R$=1.30 min; Mass spectrum (ESI$^+$): m/z=404 [M+H]$^+$.

Example 90

N-Cyclopropyl-N-(3'-fluoro-5'-trifluoromethyl-3,4,5,6-tetrahydro-2H-[1,2']bipyridinyl-4-yl)-4-(2-methyl-imidazol-1-yl)-benzamide

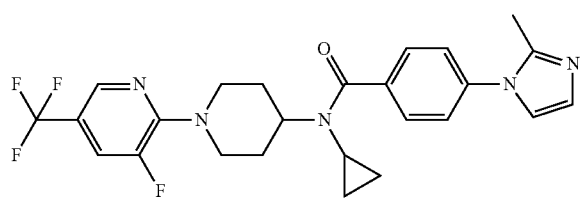 [SMILES: Cc1nccn1-c1ccc(C(=O)N(C2CC2)C2CCN(c3ncc(C(F)(F)F)cc3F)CC2)cc1]

Bromo-tris-pyrrolidino-phosphonium hexafluorophosphate (PyBrOP, 14 mg) in N,N-dimethylformamide (0.1 mL) is added to a solution of cyclopropyl-(3'-fluoro-5'-trifluoromethyl-3,4,5,6-tetrahydro-2H-[1,2']bipyridinyl-4-yl)-amine (6 mg), 4-(2-methyl-imidazol-1-yl)-benzoic acid (6 mg), and triethylamine (0.015 mL) in N,N-dimethylformamide (0.4 mL) at room temperature. The solution is stirred for 2 h and then submitted to chromatography on reversed phase (HPLC, acetonitrile/water/trifluoroacetic acid) to give the pure title compound. LC (method 19): $t_R$=4.33 min; Mass spectrum (ESI$^+$): m/z=488 [M+H]$^+$.

Example 91

N-Cyclopropyl-N-(3'-fluoro-5'-trifluoromethyl-3,4,5,6-tetrahydro-2H-[1,2']bipyridinyl-4-yl)-4-[1,2,4]triazol-1-yl-benzamide

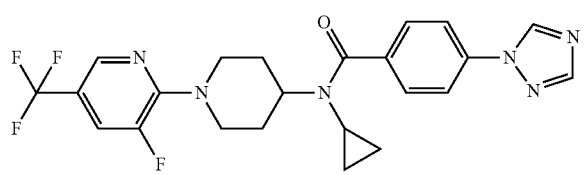 [SMILES: O=C(c1ccc(-n2cncn2)cc1)N(C1CC1)C1CCN(c2ncc(C(F)(F)F)cc2F)CC1]

The title compound is prepared from cyclopropyl-(3'-fluoro-5'-trifluoromethyl-3,4,5,6-tetrahydro-2H-[1,2']bipyridinyl-4-yl)-amine and 4-[1,2,4]triazol-1-yl-benzoic acid following a procedure analogous to that described in Example 90. LC (method 19): $t_R$=4.61 min; Mass spectrum (ESI$^+$): m/z=475 [M+H]$^+$.

Example 92

N-Cyclopropyl-N-(3'-fluoro-5'-trifluoromethyl-3,4,5,6-tetrahydro-2H-[1,2']bipyridinyl-4-yl)-4-(5-methyl-[1,2,4]triazol-1-yl)-benzamide

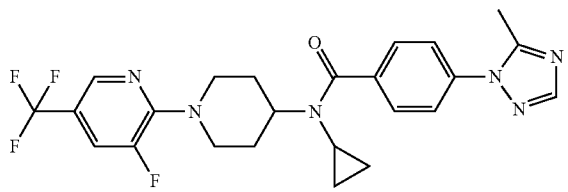 [SMILES: Cc1ncnn1-c1ccc(C(=O)N(C2CC2)C2CCN(c3ncc(C(F)(F)F)cc3F)CC2)cc1]

The title compound is prepared from cyclopropyl-(3'-fluoro-5'-trifluoromethyl-3,4,5,6-tetrahydro-2H-[1,2']bipyridinyl-4-yl)-amine and 4-(5-methyl-[1,2,4]triazol-1-yl)-benzoic acid following a procedure analogous to that described in Example 90. LC (method 19): $t_R$=4.54 min; Mass spectrum (ESI$^+$): m/z=489 [M+H]$^+$.

Example 93

N-Cyclopropyl-3-fluoro-N-(3'-fluoro-5'-trifluoromethyl-3,4,5,6-tetrahydro-2H-[1,2']bipyridinyl-4-yl)-4-(2-methyl-imidazol-1-yl)-benzamide

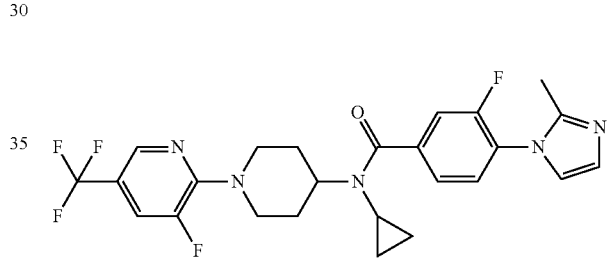

The title compound is prepared from cyclopropyl-(3'-fluoro-5'-trifluoromethyl-3,4,5,6-tetrahydro-2H-[1,2']bipyridinyl-4-yl)-amine and 3-fluoro-4-(2-methyl-imidazol-1-yl)-benzoic acid following a procedure analogous to that described in Example 90. LC (method 19): $t_R$=4.71 min; Mass spectrum (ESI$^+$): m/z=506 [M+H]$^+$.

Example 94

N-Cyclopropyl-3-fluoro-N-(3'-fluoro-5'-trifluoromethyl-3,4,5,6-tetrahydro-2H-[1,2']bipyridinyl-4-yl)-4-[1,2,4]triazol-1-yl-benzamide

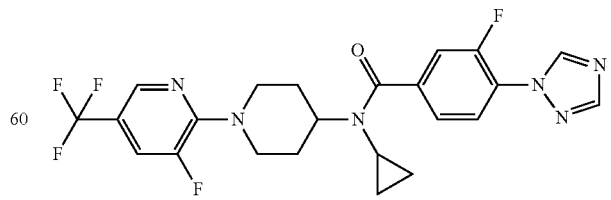

The title compound is prepared from cyclopropyl-(3'-fluoro-5'-trifluoromethyl-3,4,5,6-tetrahydro-2H-[1,2']bipyridinyl-4-yl)-amine and 3-fluoro-4-[1,2,4]triazol-1-yl-benzoic acid following a procedure analogous to that described in Example 90. LC (method 19): $t_R$=4.44 min; Mass spectrum (ESI⁺): m/z=493 [M+H]⁺.

Example 95

N-Cyclopropyl-3-fluoro-N-(3'-fluoro-5'-trifluoromethyl-3,4,5,6-tetrahydro-2H-[1,2']bipyridinyl-4-yl)-4-(5-methyl-[1,2,4]triazol-1-yl)-benzamide

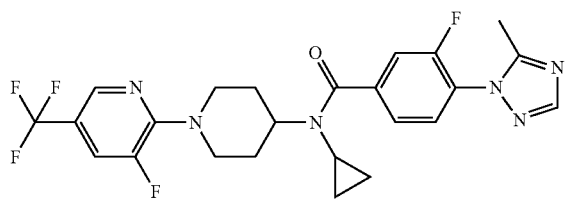 [SMILES: Cc1ncnn1-c1ccc(C(=O)N(C2CC2)C2CCN(c3ncc(C(F)(F)F)cc3F)CC2)cc1F]

The title compound is prepared from cyclopropyl-(3'-fluoro-5'-trifluoromethyl-3,4,5,6-tetrahydro-2H-[1,2']bipyridinyl-4-yl)-amine and 3-fluoro-4-(5-methyl-[1,2,4]triazol-1-yl)-benzoic acid following a procedure analogous to that described in Example 90. LC (method 19): $t_R$=4.64 min; Mass spectrum (ESI⁺): m/z=507 [M+H]⁺.

Example 96

N-Cyclopropyl-N-[1-(3-isopropyl-[1,2,4]oxadiazol-5-yl)-piperidin-4-yl]-4-(2-methyl-imidazol-1-yl)-benzamide

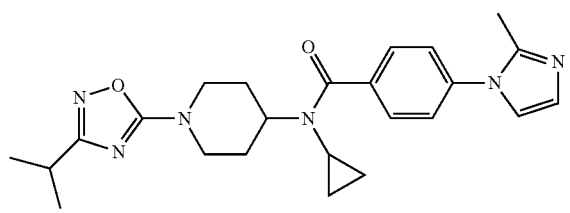 [SMILES: Cc1nccn1-c1ccc(C(=O)N(C2CC2)C2CCN(c3nc(C(C)C)no3)CC2)cc1]

The title compound is prepared from cyclopropyl-[1-(3-isopropyl-[1,2,4]oxadiazol-5-yl)-piperidin-4-yl]-amine and 4-(2-methyl-imidazol-1-yl)-benzoic acid following a procedure analogous to that described in Example 90. LC (method 19): $t_R$=3.46 min; Mass spectrum (ESI⁺): m/z=435 [M+H]⁺.

Example 97

N-Cyclopropyl-N-[1-(3-isopropyl-[1,2,4]oxadiazol-5-yl)-piperidin-4-yl]-4-[1,2,4]triazol-1-yl-benzamide

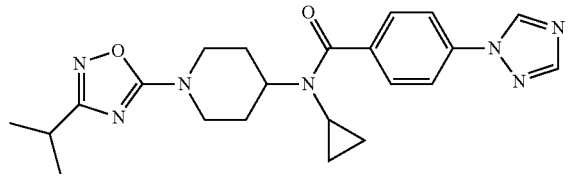 [SMILES: CC(C)c1noc(N2CCC(N(C(=O)c3ccc(-n4cncn4)cc3)C3CC3)CC2)n1]

The title compound is prepared from cyclopropyl-[1-(3-isopropyl-[1,2,4]oxadiazol-5-yl)-piperidin-4-yl]-amine and 4-[1,2,4]triazol-1-yl-benzoic acid following a procedure analogous to that described in Example 90. LC (method 19): $t_R$=3.71 min; Mass spectrum (ESI⁺): m/z=422 [M+H]⁺.

Example 98

N-Cyclopropyl-N-[1-(3-isopropyl-[1,2,4]oxadiazol-5-yl)-piperidin-4-yl]-4-(5-methyl-[1,2,4]triazol-1-yl)-benzamide

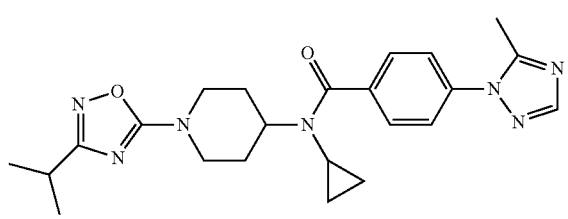 [SMILES: Cc1ncnn1-c1ccc(C(=O)N(C2CC2)C2CCN(c3nc(C(C)C)no3)CC2)cc1]

The title compound is prepared from cyclopropyl-[1-(3-isopropyl-[1,2,4]oxadiazol-5-yl)-piperidin-4-yl]-amine and 4-(5-methyl-[1,2,4]triazol-1-yl)-benzoic acid following a procedure analogous to that described in Example 90. LC (method 19): $t_R$=3.30 min; Mass spectrum (ESI⁺): m/z=436 [M+H]⁺.

Example 99

N-Cyclopropyl-3-fluoro-N-[1-(3-isopropyl-[1,2,4]oxadiazol-5-yl)-piperidin-4-yl]-4-(2-methyl-imidazol-1-yl)-benzamide

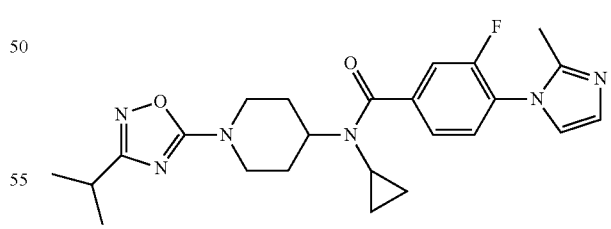

The title compound is prepared from cyclopropyl-[1-(3-isopropyl-[1,2,4]oxadiazol-5-yl)-piperidin-4-yl]-amine and 3-fluoro-4-(2-methyl-imidazol-1-yl)-benzoic acid following a procedure analogous to that described in Example 90. LC (method 19): $t_R$=3.98 min; Mass spectrum (ESI⁺): m/z=453 [M+H]⁺.

Example 100

N-Cyclopropyl-3-fluoro-N-[1-(3-isopropyl-[1,2,4]oxadiazol-5-yl)-piperidin-4-yl]-4-[1,2,4]triazol-1-yl-benzamide

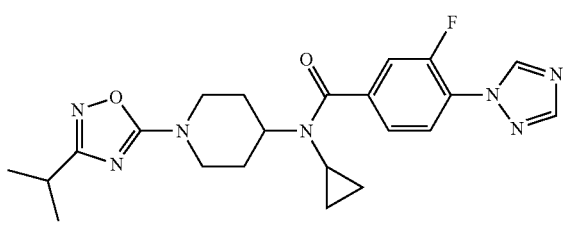 [SMILES: CC(C)c1noc(N2CCC(N(C(=O)c3ccc(-n4cncn4)c(F)c3)C3CC3)CC2)n1]

The title compound is prepared from cyclopropyl-[1-(3-isopropyl-[1,2,4]oxadiazol-5-yl)-piperidin-4-yl]-amine and 3-fluoro-4-[1,2,4]triazol-1-yl-benzoic acid following a procedure analogous to that described in Example 90. LC (method 19): $t_R$=3.84 min; Mass spectrum (ESI$^+$): m/z=440 [M+H]$^+$.

Example 101

N-Cyclopropyl-3-fluoro-N-[1-(3-isopropyl-[1,2,4]oxadiazol-5-yl)-piperidin-4-yl]-4-(5-methyl-[1,2,4]triazol-1-yl)-benzamide

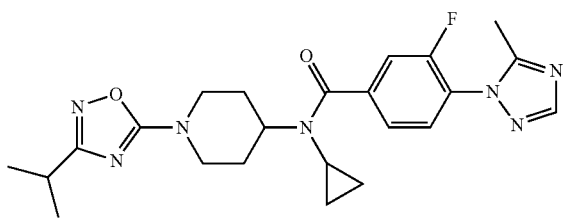 [SMILES: Cc1ncnn1-c1ccc(C(=O)N(C2CC2)C2CCN(c3nc(C(C)C)no3)CC2)cc1F]

The title compound is prepared from cyclopropyl-[1-(3-isopropyl-[1,2,4]oxadiazol-5-yl)-piperidin-4-yl]-amine and 3-fluoro-4-(5-methyl-[1,2,4]triazol-1-yl)-benzoic acid following a procedure analogous to that described in Example 90. LC (method 19): $t_R$=3.84 min; Mass spectrum (ESI$^+$): m/z=454 [M+H]$^+$.

Example 102

N-Cyclopropyl-N-[1-(5-ethyl-pyrimidin-2-yl)-piperidin-4-yl]-4-(2-methyl-imidazol-1-yl)-benzamide

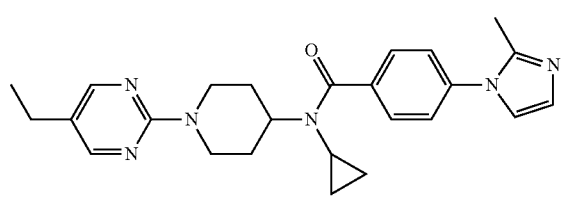 [SMILES: CCc1cnc(N2CCC(N(C(=O)c3ccc(-n4ccnc4C)cc3)C3CC3)CC2)nc1]

The title compound is prepared from cyclopropyl-[1-(5-ethyl-pyrimidin-2-yl)-piperidin-4-yl]-amine and 4-(2-methyl-imidazol-1-yl)-benzoic acid following a procedure analogous to that described in Example 90. LC (method 19): $t_R$=3.84 min; Mass spectrum (ESI$^+$): m/z=431 [M+H]$^+$.

Example 103

N-Cyclopropyl-N-[1-(5-ethyl-pyrimidin-2-yl)-piperidin-4-yl]-4-(5-methyl-[1,2,4]triazol-1-yl)-benzamide

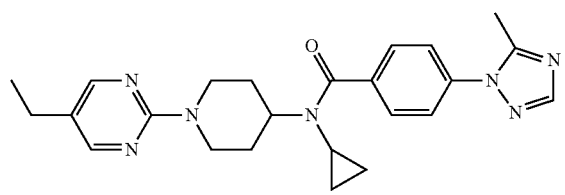 [SMILES: CCc1cnc(N2CCC(N(C(=O)c3ccc(-n4ncnc4C)cc3)C3CC3)CC2)nc1]

The title compound is prepared from cyclopropyl-[1-(5-ethyl-pyrimidin-2-yl)-piperidin-4-yl]-amine and 4-(5-methyl-[1,2,4]triazol-1-yl)-benzoic acid following a procedure analogous to that described in Example 90. LC (method 19): $t_R$=3.77 min; Mass spectrum (ESI$^+$): m/z=432 [M+H]$^+$.

Example 104

N-Cyclopropyl-N-[1-(5-ethyl-pyrimidin-2-yl)-piperidin-4-yl]-3-fluoro-4-(2-methyl-imidazol-1-yl)-benzamide

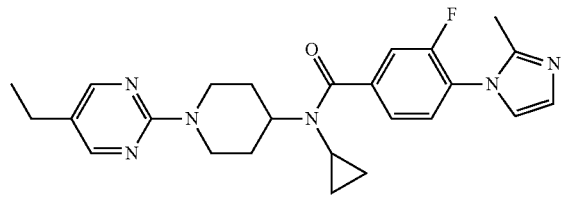 [SMILES: CCc1cnc(N2CCC(N(C(=O)c3ccc(-n4ccnc4C)c(F)c3)C3CC3)CC2)nc1]

The title compound is prepared from cyclopropyl-[1-(5-ethyl-pyrimidin-2-yl)-piperidin-4-yl]-amine and 3-fluoro-4-(2-methyl-imidazol-1-yl)-benzoic acid following a procedure analogous to that described in Example 90. LC (method 19): $t_R$=3.81 min; Mass spectrum (ESI$^+$): m/z=449 [M+H]$^+$.

Example 105

N-Cyclopropyl-N-[1-(5-ethyl-pyrimidin-2-yl)-piperidin-4-yl]-3-fluoro-4-[1,2,4]triazol-1-yl-benzamide

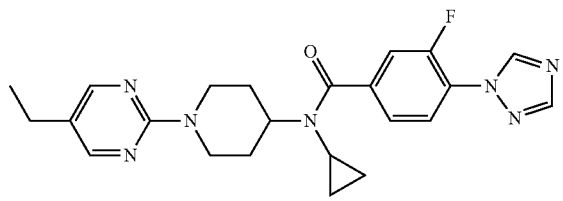 [SMILES: CCc1cnc(N2CCC(N(C(=O)c3ccc(-n4cncn4)c(F)c3)C3CC3)CC2)nc1]

The title compound is prepared from cyclopropyl-[1-(5-ethyl-pyrimidin-2-yl)-piperidin-4-yl]-amine and 3-fluoro-4-[1,2,4]triazol-1-yl-benzoic acid following a procedure analogous to that described in Example 90. LC (method 19): $t_R$=4.25 min; Mass spectrum (ESI$^+$): m/z=436 [M+H]$^+$.

Example 106

N-Cyclopropyl-N-[1-(5-ethyl-pyrimidin-2-yl)-piperidin-4-yl]-3-fluoro-4-(5-methyl-[1,2,4]triazol-1-yl)-benzamide

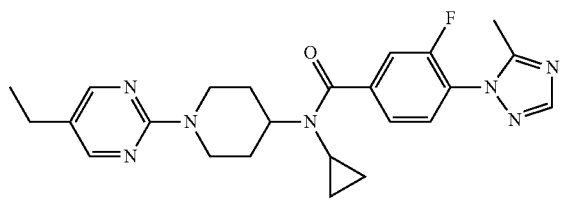 [SMILES: CCc1cnc(N2CCC(N(C(=O)c3ccc(-n4ncnc4C)c(F)c3)C3CC3)CC2)nc1]

The title compound is prepared from cyclopropyl-[1-(5-ethyl-pyrimidin-2-yl)-piperidin-4-yl]-amine and 3-fluoro-4-(5-methyl-[1,2,4]triazol-1-yl)-benzoic acid following a procedure analogous to that described in Example 90. LC (method 19): $t_R$=3.69 min; Mass spectrum (ESI$^+$): m/z=450 [M+H]$^+$.

Example 107

N-[1-(5-Chloro-pyrimidin-2-yl)-piperidin-4-yl]-N-cyclopropyl-4-(2-methyl-imidazol-1-yl)-benzamide

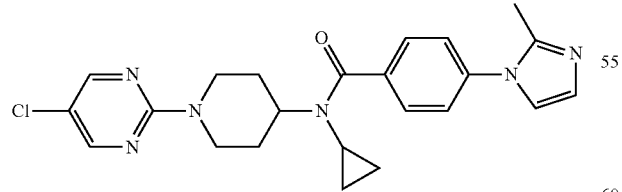

1-(3-Dimethylamino-propyl)-3-ethyl-carbodiimide (EDC, 12 mg) in N,N-dimethylformamide (0.1 mL) is added to a solution of [1-(5-chloro-pyrimidin-2-yl)-piperidin-4-yl]-cyclopropyl-amine (5 mg), 4-(2-methyl-imidazol-1-yl)-benzoic acid (6 mg), 1-hydroxy-benzo-triazole (3 mg), and triethylamine (15 μL) in N,N-dimethylformamide (0.4 mL) at room temperature. The solution is stirred for 18 h and then submitted to chromatography on reversed phase (HPLC, acetonitrile/water/trifluoroacetic acid) to give the pure title compound. LC (method 19): $t_R$=3.97 min; Mass spectrum (ESI$^+$): m/z=437 [M+H]$^+$.

Example 108

N-[1-(5-Chloro-pyrimidin-2-yl)-piperidin-4-yl]-N-cyclopropyl-4-[1,2,4]triazol-1-yl-benzamide

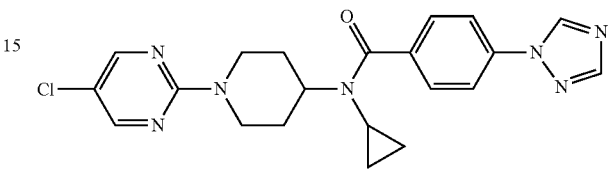

The title compound is prepared from [1-(5-chloro-pyrimidin-2-yl)-piperidin-4-yl]-cyclopropyl-amine and 4-[1,2,4]triazol-1-yl-benzoic acid following a procedure analogous to that described in Example 107. LC (method 19): $t_R$=3.86 min; Mass spectrum (ESI$^+$): m/z=424 [M+H]$^+$.

Example 109

N-[1-(5-Chloro-pyrimidin-2-yl)-piperidin-4-yl]-N-cyclopropyl-4-(5-methyl-[1,2,4]triazol-1-yl)-benzamide

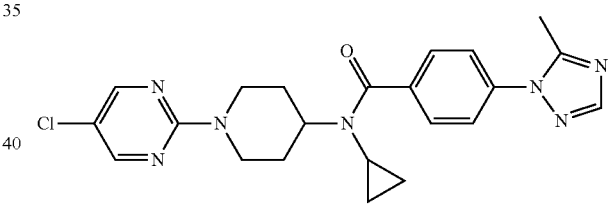

The title compound is prepared from [1-(5-chloro-pyrimidin-2-yl)-piperidin-4-yl]-cyclopropyl-amine and 4-(5-methyl-[1,2,4]triazol-1-yl)-benzoic acid following a procedure analogous to that described in Example 107. LC (method 19): $t_R$=3.79 min; Mass spectrum (ESI$^+$): m/z=438 [M+H]$^+$.

Example 110

N-[1-(5-Chloro-pyrimidin-2-yl)-piperidin-4-yl]-N-cyclopropyl-4-tetrazol-1-yl-benzamide

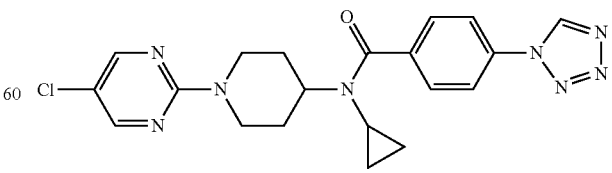

The title compound is prepared from [1-(5-chloro-pyrimidin-2-yl)-piperidin-4-yl]-cyclopropyl-amine and 4-tetrazol-1-yl-benzoic acid following a procedure analogous to that described in Example 107. LC (method 19): $t_R$=4.05 min; Mass spectrum (ESI$^+$): m/z=425 [M+H]$^+$.

Example 111

N-[1-(5-Chloro-pyrimidin-2-yl)-piperidin-4-yl]-N-cyclopropyl-4-(5-methyl-tetrazol-1-yl)-benzamide

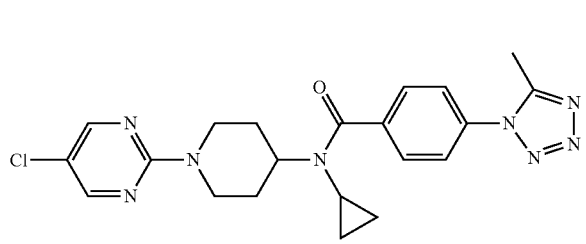 [SMILES: Cc1nnnn1-c1ccc(C(=O)N(C2CC2)C2CCN(c3ncc(Cl)cn3)CC2)cc1]

The title compound is prepared from [1-(5-chloro-pyrimidin-2-yl)-piperidin-4-yl]-cyclopropyl-amine and 4-(5-methyl-tetrazol-1-yl)-benzoic acid following a procedure analogous to that described in Example 107. LC (method 19): $t_R$=4.02 min; Mass spectrum (ESI$^+$): m/z=439 [M+H]$^+$.

Example 112

N-[1-(5-Chloro-pyrimidin-2-yl)-piperidin-4-yl]-N-cyclopropyl-3-fluoro-4-(2-methyl-imidazol-1-yl)-benzamide

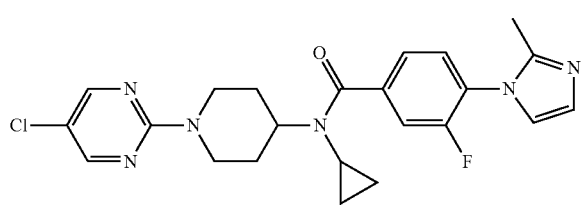 [SMILES: Cc1nccn1-c1ccc(C(=O)N(C2CC2)C2CCN(c3ncc(Cl)cn3)CC2)cc1F]

The title compound is prepared from [1-(5-chloro-pyrimidin-2-yl)-piperidin-4-yl]-cyclopropyl-amine and 3-fluoro-4-(2-methyl-imidazol-1-yl)-benzoic acid following a procedure analogous to that described in Example 107. LC (method 19): $t_R$=4.04 min; Mass spectrum (ESI$^+$): m/z=455 [M+H]$^+$.

Example 113

N-[1-(5-Chloro-pyrimidin-2-yl)-piperidin-4-yl]-N-cyclopropyl-3-fluoro-4-[1,2,4]triazol-1-yl-benzamide

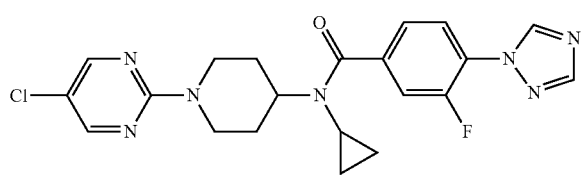 [SMILES: O=C(c1ccc(-n2cncn2)c(F)c1)N(C1CC1)C1CCN(c2ncc(Cl)cn2)CC1]

The title compound is prepared from [1-(5-chloro-pyrimidin-2-yl)-piperidin-4-yl]-cyclopropyl-amine and 3-fluoro-4-[1,2,4]triazol-1-yl-benzoic acid following a procedure analogous to that described in Example 107. LC (method 19): $t_R$=4.00 min; Mass spectrum (ESI$^+$): m/z=442 [M+H]$^+$.

Example 114

N-[1-(5-Chloro-pyrimidin-2-yl)-piperidin-4-yl]-N-cyclopropyl-3-fluoro-4-(5-methyl-[1,2,4]triazol-1-yl)-benzamide

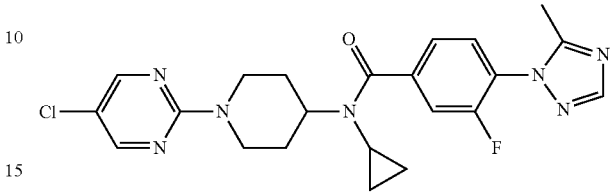

The title compound is prepared from [1-(5-chloro-pyrimidin-2-yl)-piperidin-4-yl]-cyclopropyl-amine and 3-fluoro-4-(5-methyl-[1,2,4]triazol-1-yl)-benzoic acid following a procedure analogous to that described in Example 107. LC (method 19): $t_R$=3.90 min; Mass spectrum (ESI$^+$): m/z=456 [M+H]$^+$.

Example 115

N-[1-(5-Chloro-pyrimidin-2-yl)-piperidin-4-yl]-N-cyclopropyl-3-fluoro-4-tetrazol-1-yl-benzamide

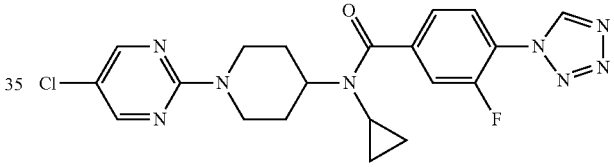

The title compound is prepared from [1-(5-chloro-pyrimidin-2-yl)-piperidin-4-yl]-cyclopropyl-amine and 3-fluoro-4-tetrazol-1-yl-benzoic acid following a procedure analogous to that described in Example 107. LC (method 19): $t_R$=4.18 min; Mass spectrum (ESI$^+$): m/z=443 [M+H]$^+$.

Example 116

N-[1-(5-Chloro-pyrimidin-2-yl)-piperidin-4-yl]-N-cyclopropyl-3-fluoro-4-(5-methyl-tetrazol-1-yl)-benzamide

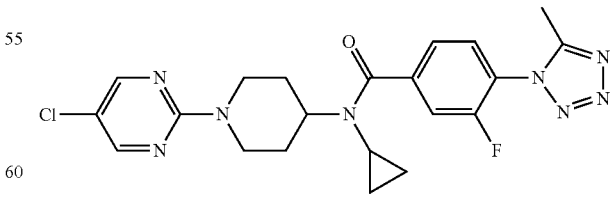

The title compound is prepared from [1-(5-chloro-pyrimidin-2-yl)-piperidin-4-yl]-cyclopropyl-amine and 3-fluoro-4-(5-methyl-tetrazol-1-yl)-benzoic acid following a procedure analogous to that described in Example 107. LC (method 19): $t_R$=4.18 min; Mass spectrum (ESI$^+$): m/z=457 [M+H]$^+$.

Example 117

N-Cyclopropyl-N-(3'-fluoro-5'-trifluoromethyl-3,4,5,6-tetrahydro-2H-[1,2']bipyridinyl-4-yl)-4-tetrazol-1-yl-benzamide

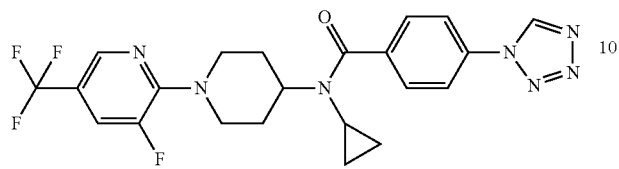

The title compound is prepared from cyclopropyl-(3'-fluoro-5'-trifluoromethyl-3,4,5,6-tetrahydro-2H-[1,2']bipyridinyl-4-yl)-amine and 4-tetrazol-1-yl-benzoic acid following a procedure analogous to that described in Example 107. LC (method 19): $t_R$=4.46 min; Mass spectrum (ESI$^+$): m/z=476 [M+H]$^+$.

Example 118

N-Cyclopropyl-N-(3'-fluoro-5'-trifluoromethyl-3,4,5,6-tetrahydro-2H-[1,2']bipyridinyl-4-yl)-4-(5-methyl-tetrazol-1-yl)-benzamide

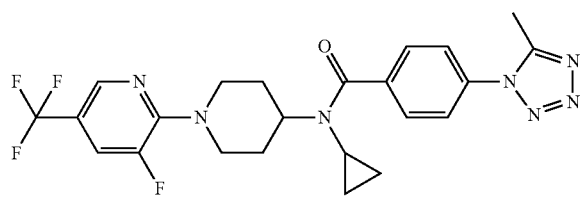 [SMILES: Cc1nnnn1-c1ccc(C(=O)N(C2CC2)C2CCN(c3ncc(C(F)(F)F)cc3F)CC2)cc1]

The title compound is prepared from cyclopropyl-(3'-fluoro-5'-trifluoromethyl-3,4,5,6-tetrahydro-2H-[1,2']bipyridinyl-4-yl)-amine and 4-(5-methyl-tetrazol-1-yl)-benzoic acid following a procedure analogous to that described in Example 107. LC (method 19): $t_R$=4.41 min; Mass spectrum (ESI$^+$): m/z=490 [M+H]$^+$.

Example 119

N-Cyclopropyl-3-fluoro-N-(3'-fluoro-5'-trifluoromethyl-3,4,5,6-tetrahydro-2H-[1,2]bipyridinyl-4-yl)-4-(5-methyl-tetrazol-1-yl)-benzamide

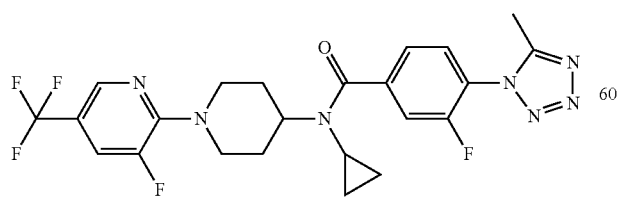

The title compound is prepared from cyclopropyl-(3'-fluoro-5'-trifluoromethyl-3,4,5,6-tetrahydro-2H-[1,2']bipyridinyl-4-yl)-amine and 3-fluoro-4-(5-methyl-tetrazol-1-yl)-benzoic acid following a procedure analogous to that described in Example 107. LC (method 19): $t_R$=4.58 min; Mass spectrum (ESI$^+$): m/z=508 [M+H]$^+$.

Example 120

(3S,4R)—N-Cyclopropyl-N-(3-fluoro-5'-trifluoromethyl-3,4,5,6-tetrahydro-2H-[1,2']bipyridinyl-4-yl)-4-(5-methyl-tetrazol-1-yl)-benzamide (Absolute Configurations Arbitrarily Assigned)

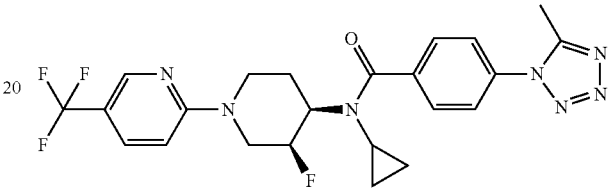

The title compound is prepared from (3S,4R)-cyclopropyl-(3-fluoro-5'-trifluoromethyl-3,4,5,6-tetrahydro-2H-[1,2']bipyridinyl-4-yl)-amine and 4-(5-methyl-tetrazol-1-yl)-benzoic acid following a procedure analogous to that described in Example 107. LC (method 19): $t_R$=4.26 min; Mass spectrum (ESI$^+$): m/z=490 [M+H]$^+$.

Example 121

(3S,4R)—N-Cyclopropyl-3-fluoro-N-(3-fluoro-5'-trifluoromethyl-3,4,5,6-tetrahydro-2H-[1,2']bipyridinyl-4-yl)-4-tetrazol-1-yl-benzamide (Absolute Configurations Arbitrarily Assigned)

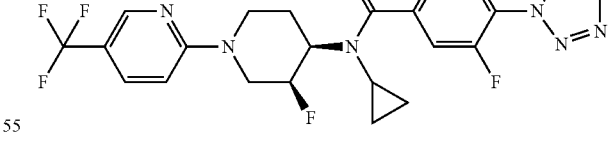

The title compound is prepared from (3S,4R)-cyclopropyl-(3-fluoro-5'-trifluoromethyl-3,4,5,6-tetrahydro-2H-[1,2']bipyridinyl-4-yl)-amine and 3-fluoro-4-tetrazol-1-yl-benzoic acid following a procedure analogous to that described in Example 107. LC (method 19): $t_R$=4.39 min; Mass spectrum (ESI$^+$): m/z=494 [M+H]$^+$.

The invention claimed is:

1. A compound of formula I

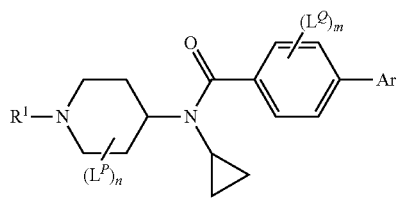

I wherein:
R$^1$ is a 5- or 6-membered heteroaromatic ring which contains 1, 2, or 3 heteroatoms independently selected from N, O, and S, wherein optionally a second carbocyclic ring is condensed to the heteroaromatic ring, and the second carbocyclic ring is unsaturated or aromatic and 5- or 6-membered and optionally contains 1, 2, or 3 heteroatoms independently selected from N, O, and S, and 1 or 2 —CH$_2$— groups in the second carbocyclic ring are optionally replaced by —N(R$^N$)—, —C(=O)—, —S(=O)—, or —S(=O)$_2$—, and wherein in the heteroaromatic ring and/or the second carbocyclic ring the H-atom in one or more NH groups is optionally replaced by R$^N$, and wherein each of the heteroaromatic ring and second carbocyclic ring are independently optionally substituted with one or more substituents selected from L$^{Ar}$ and the heteroaromatic ring or the second carbocyclic ring is optionally substituted with a group R$^2$;

R$^N$ are each independently H, C$_{1-4}$-alkyl, C$_{1-4}$-alkyl-C(=O)—, or C$_{1-4}$-alkyl-S(=O)$_2$—;

Ar is a phenyl ring, a tetrazolyl ring, or a 5- or 6-membered heteroaromatic ring which contains 1, 2, or 3 heteroatoms independently selected from N, O, and S, wherein optionally a second carbocyclic ring is condensed to the phenyl ring or heteroaromatic ring, and the second carbocyclic ring is unsaturated or aromatic and 5- or 6-membered and optionally contains 1, 2, or 3 heteroatoms independently selected from N, O, and S, and 1 or 2 —CH$_2$— groups in the second carbocyclic ring are optionally replaced by —N(R$^N$)—, —C(=O)—, —S(=O)—, or —S(=O)$_2$—, and wherein in the heteroaromatic ring and/or the second carbocyclic ring the H-atom in one or more NH groups are optionally replaced by R$^N$, and wherein each of the phenyl ring, heteroaromatic ring, and second carbocyclic ring independently are optionally substituted with one or more substituents selected from L$^{Ar}$ and the phenyl ring, tetrazolyl ring, heteroaromatic ring, or second carbocyclic ring are each optionally substituted with a group T;

T is F, Cl, Br, I, CN, OH, NO$_2$, C$_{1-6}$-alkyl-, C$_{1-6}$-alkenyl-, C$_{1-6}$-alkynyl-, C$_{3-6}$-cycloalkyl, C$_{1-6}$-alkyl-O—, C$_{3-6}$-cycloalkyl-O—, C$_{1-6}$-alkyl-S—, HO—C(=O)—, C$_{1-6}$-alkyl-O—C(=O)—, C$_{1-4}$-alkyl-C(=O)—, C$_{3-6}$-cycloalkyl-C(=O)—, C$_{1-4}$-alkyl-S(=O)—, C$_{1-4}$-alkyl-S(=O)$_2$—, R$^{NT1}$R$^{NT2}$N—, R$^{NT1}$R$^{NT2}$N—C(=O)—, R$^{NT1}$R$^{NT2}$N—S(=O)$_2$—, R$^{NT1}$R$^{NT2}$N—C(=O)—(R$^N$)N—, heterocyclyl, heterocyclyl-O—, aryl, aryl-O—, heteroaryl, or heteroaryl-O—, wherein each alkyl, alkenyl, alkynyl, and cycloalkyl group is optionally substituted with one or more substituents independently selected from F, Cl, CN, OH, C$_{1-3}$-alkyl, C$_{3-6}$-cycloalkyl, C$_{1-3}$-alkyl-O—, R$^{NT1}$R$^{NT2}$N—, R$^{NT1}$R$^{NT2}$N—C(=O)—, C$_{1-4}$-alkyl-S(=O)—, C$_{1-4}$-alkyl-S(=O)$_2$—, R$^{NT1}$R$^{NT2}$N—S(=O)$_2$—, aryl, heteroaryl, and heterocyclyl, and wherein heteroaryl is a 5- or 6-membered aromatic carbocyclic ring which contains 1, 2, 3, or 4 heteroatoms independently selected from N, O, and S, wherein the H-atom in one or more NH groups is optionally replaced by R$^N$, and heterocyclyl is a 4- to 7-membered unsaturated or saturated carbocyclic ring in which 1 or 2-CH$_2$-groups are independently replaced by NR$^N$, O, —C(=O)—, S, —S(=O)—, or —S(=O)$_2$—, and/or in which a —CH— group is replaced by N, and wherein each aryl, heteroaryl, or heterocyclyl group is optionally substituted with one or more substituents independently selected from L$^{Ar}$;

R$^{NT1}$ is H, C$_{1-6}$-alkyl, C$_{3-6}$-cycloalkyl, C$_{1-6}$-alkyl-C(=O)—, C$_{1-6}$-alkyl-S(=O)$_2$, heterocyclyl, aryl, or heteroaryl, wherein each alkyl and cycloalkyl group is optionally substituted with one or more substituents independently selected from the group consisting of F, OH, CN, C$_{1-4}$-alkyl, C$_{1-4}$-alkyl-O—, R$^N{}_2$N, C$_{1-4}$-alkyl-S(=O)$_2$—, C$_{3-6}$-cycloalkyl, heterocyclyl, phenyl, and heteroaryl; and wherein heterocyclyl is a C$_{4-7}$-cycloalkyl ring in which 1 or 2-CH$_2$-groups are independently replaced by NR$^N$, O, C(=O), S, S(=O), or S(=O)$_2$; and wherein heterocyclyl is optionally substituted with one or more substituents independently selected from F, C$_{1-4}$-alkyl, R$^N{}_2$N, OH, and C$_{1-4}$-alkyl-O—; and wherein heteroaryl is a 5- or 6-membered aromatic carbocyclic ring which contains 1, 2, or 3 heteroatoms independently selected from N, O, and S, wherein the H-atom in one or more NH groups are optionally replaced by R$^N$; and wherein aryl, phenyl, and heteroaryl are optionally substituted with one or more substituents L$^{Ar}$;

R$^{NT2}$ is H and C$_{1-6}$-alkyl; or

R$^{NT1}$ and R$^{NT2}$ are linked to form a C$_{3-5}$-alkylene group, wherein 1 or 2-CH$_2$-groups are independently replaced by NR$^N$, O, C(=O), S, S(=O), or S(=O)$_2$, and optionally substituted with one or more substituents independently selected from F, C$_{1-4}$-alkyl, (R$^N$)$_2$N, OH, and C$_{1-4}$-alkyl-O—;

L$^{Ar}$ is F, Cl, Br, I, CN, OH, NO$_2$, C$_{1-4}$-alkyl-, C$_{1-4}$-alkyl-O—, (R$^N$)$_2$N—C(=O), (R$^N$)$_2$N—, or C$_{1-4}$-alkyl-S(=O)$_2$—, wherein each alkyl group is optionally independently substituted with one or more substituents selected from F, Cl, CN, OH, and C$_{1-3}$-alkyl-O—;

L$^P$ is F or C$_{1-3}$-alkyl, wherein the alkyl group is optionally substituted with one or more F-atoms;

L$^Q$ is F, Cl, CN, OH, C$_{1-4}$-alkyl, C$_{3-7}$-cycloalkyl-, F$_2$HC, F$_3$C, C$_{1-4}$-alkyl-O—, F$_2$HC—O—, F$_3$C—O—, or C$_{3-7}$-cycloalkyl-O—;

R$^2$ is F, Cl, Br, I, CN, OH, NO$_2$, C$_{1-6}$-alkyl-, C$_{1-6}$-alkenyl-, C$_{1-6}$-alkynyl-, C$_{3-6}$-cycloalkyl, C$_{1-6}$-alkyl-O—, C$_{3-6}$- cycloalkyl-O—, C$_{1-6}$-alkyl-S—, HO—C(=O)—, C$_{1-6}$-alkyl-O—C(=O)—, C$_{1-4}$-alkyl-C(=O)—, C$_{3-6}$-cycloalkyl-C(=O)—, C$_{1-4}$-alkyl-S(=O)—, C$_{1-4}$-alkyl-S(=O)$_2$—, R$^{NT1}$R$^{NT2}$N—, R$^{NT1}$R$^{NT2}$N—C(=O)—, R$^{NT1}$R$^{NT2}$N—S(=O)$_2$—, R$^{NT1}$R$^{NT2}$N—C(=O)— (R$^N$)N—, heterocyclyl, heterocyclyl-O—, aryl, aryl-O—, heteroaryl, or heteroaryl-O—, wherein each alkyl, alkenyl, alkynyl, and cycloalkyl group is optionally substituted with one or more substituents independently selected from F, Cl, CN, OH, C$_{1-3}$-alkyl, C$_{3-6}$-cycloalkyl, C$_{1-3}$-alkyl-O—, R$^{NT1}$R$^{NT2}$N—, R$^{NT1}$R$^{NT2}$N—C(=O)—, C$_{1-4}$-alkyl-S(=O)—, C$_{1-4}$-alkyl-S(=O)$_2$—, R$^{NT1}$R$^{NT2}$N—S(=O)$_2$—, aryl, heteroaryl, and heterocyclyl, wherein heteroaryl is a 5- or 6-membered aromatic carbocyclic ring which contains 1, 2, 3, or 4 heteroatoms independently selected from N, O, and S, wherein the H-atom in one or more NH groups is optionally replaced by R$^N$; and wherein heterocyclyl is a 4- to 7-membered unsaturated or saturated carbocyclic ring in which 1 or 2 —CH$_2$-groups are independently replaced by NR$^N$, O, —C(=O)—, S, —S(=O)—, or —S(=O)$_2$—, and/or in which a —CH-group is replaced by N; and wherein each aryl, heteroaryl, or heterocyclyl group is optionally substituted with one or more substituents independently selected from L$^{Ar}$;

m is 0, 1, or 2; and n is 0, 1, 2, 3, or 4, wherein aryl is phenyl or naphthyl, or a salt thereof.

2. The compound according to claim 1, wherein:

R$^1$ is a 5-membered heteroaromatic ring which contains 2 or 3 heteroatoms independently selected from N, O, and S, and a 6-membered heteroaromatic ring which contains 1 or 2 N atoms, wherein optionally a second carbocyclic ring is condensed to the 5- and 6-membered heteroaromatic rings, wherein the second carbocyclic ring is unsaturated or aromatic and 5- or 6-membered and optionally contains 1 or 2 heteroatoms independently selected from N, O, and S, and in the second carbocyclic ring are optionally replaced by —N(R$^N$)—, —C(=O)—, or —S(=O)$_2$—, and wherein in the heteroaromatic ring and/or the second carbocyclic ring the H-atom in one or more NH groups are optionally replaced by R$^N$, and wherein each of the heteroaromatic ring and/or second carbocyclic ring independently is optionally substituted with one or two substituents selected from L$^{Ar}$, and wherein the heteroaromatic ring or the second carbocyclic ring is optionally substituted with a group R$^2$.

3. The compound according to claim 1, wherein:

Ar is a phenyl ring, a tetrazolyl ring, a 6-membered heteroaromatic ring which contains 1 or 2 N-atoms, or a 5-membered heteroaromatic ring which contains 1, 2, or 3 heteroatoms independently selected from N, O and S; wherein the phenyl ring, tetrazolyl ring, or heteroaromatic ring is optionally substituted with a group T, and wherein the phenyl ring and heteroaromatic ring are optionally substituted with one or more substituents independently selected from L$^{Ar}$, and wherein in the heteroaromatic rings the H-atom in one or more NH groups is optionally replaced by R$^N$.

4. The compound according to claim 1, wherein:

Ar is a phenyl ring, a 5-membered heteroaromatic ring which contains 2 or 3 heteroatoms independently selected from N, O, or S, and a 6-membered heteroaromatic ring which contains 1 or 2 N atoms, wherein a second carbocyclic ring is condensed to the phenyl ring or the heteroaromatic ring, wherein the second carbocyclic ring is unsaturated or aromatic and is 5- or 6-membered and optionally contains 1 or 2 heteroatoms independently selected from N, O, and S, and 1 or 2 —CH$_2$— groups in the second carbocyclic ring are optionally replaced by —N(R$^N$)—, —C(=O)—, —S(=O)—, or —S(=O)$_2$—, and wherein in the heteroaromatic ring and/or the second carbocyclic ring the H-atom in one or more NH groups are optionally replaced by R$^N$, and wherein each of the phenyl ring, heteroaromatic ring, and second carbocyclic ring is optionally substituted with one or more substituents independently selected from L$^{Ar}$, and wherein the phenyl ring, heteroaromatic ring, or second carbocyclic ring is optionally substituted with a group T.

5. The compound according to claim 1, wherein T is CN, C$_{1-3}$-alkyl-, NC—C$_{1-3}$-alkyl-, C$_{1-4}$-alkyl-S(=O)—, C$_{1-4}$-alkyl-S(=O)$_2$—, R$^{NT1}$R$^{NT2}$N—S(=O)$_2$—, R$^{NT1}$R$^{NT2}$N—C(=O)—, or R$^{NT1}$R$^{NT2}$N—.

6. The compound according to claim 1 selected from:

(1)

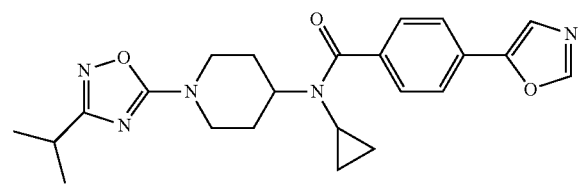

(2)

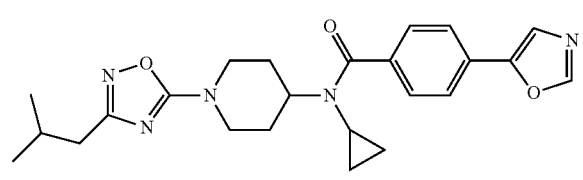

(3)

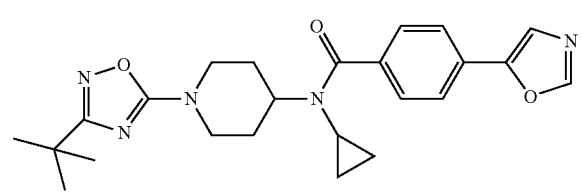

(4)

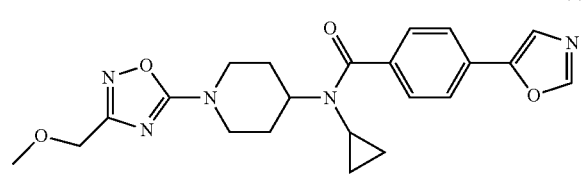

(5)

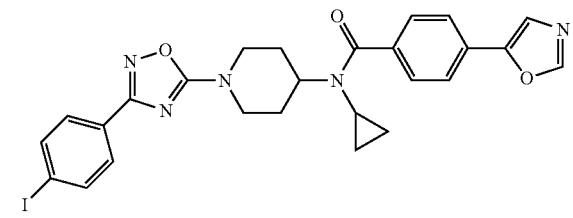

(6)
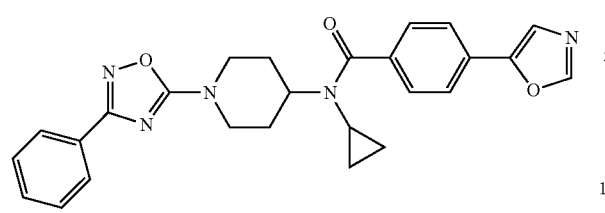
(7)
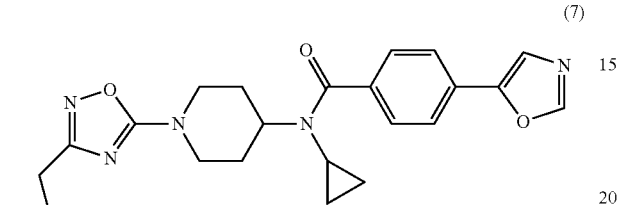
(8)
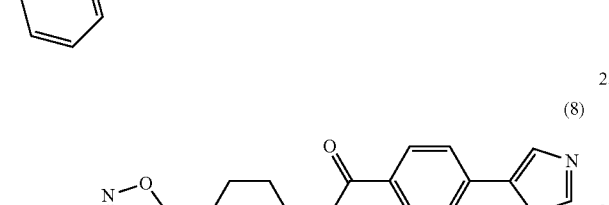
(9)
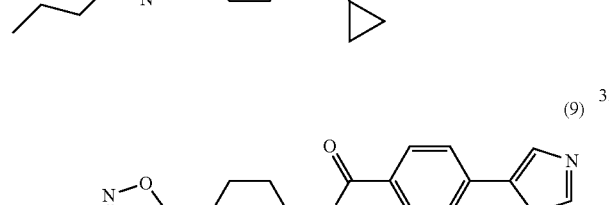
(10)
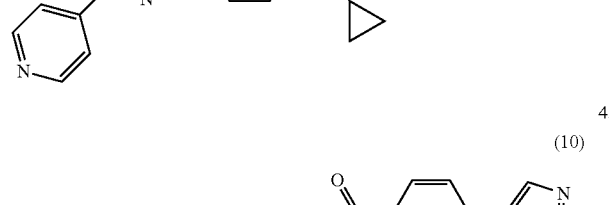
(11)
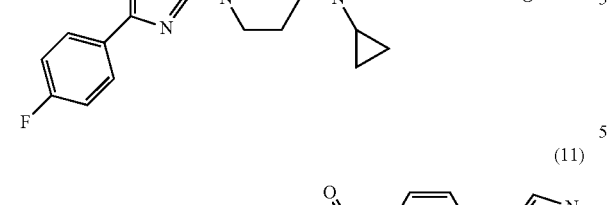
(12)
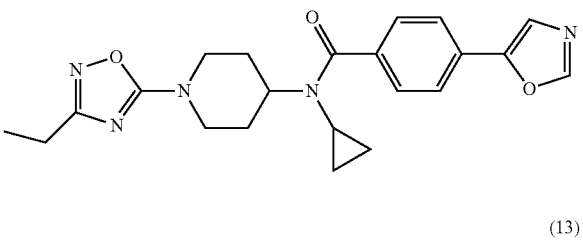
(13)
(14)
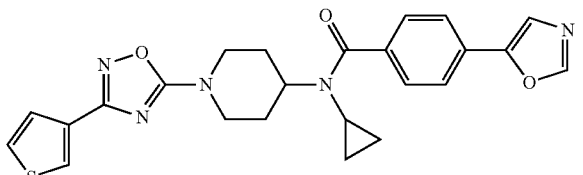
(15)
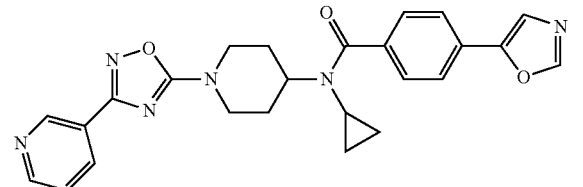
(16)
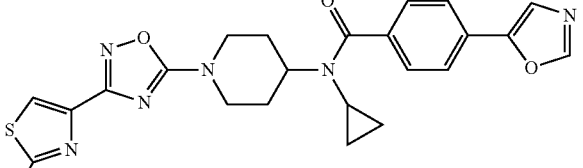
(17)
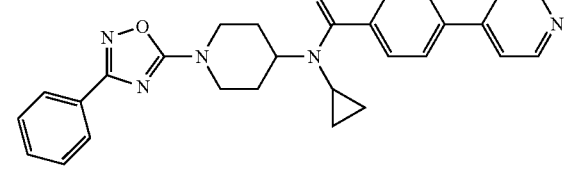
(18)
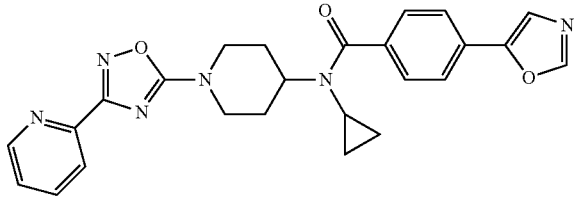

-continued
(19)
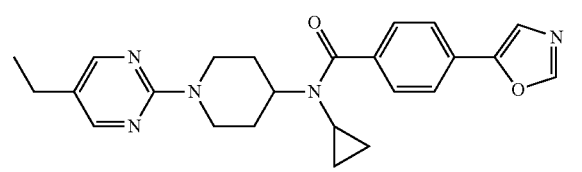
(20)
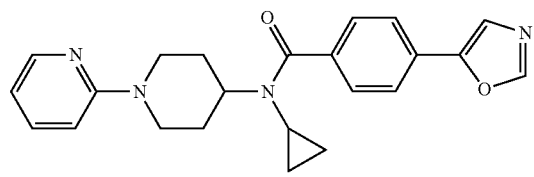
(21)
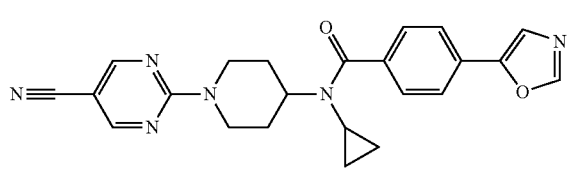
(22)
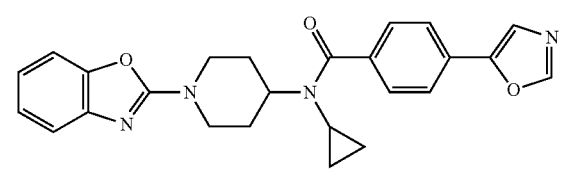
(23)
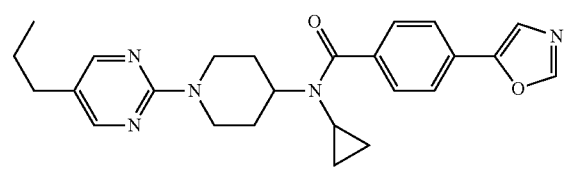
(24)
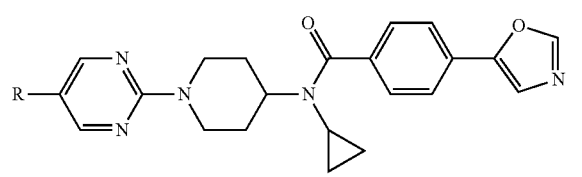
R = 4-chlorophenyl
(25)
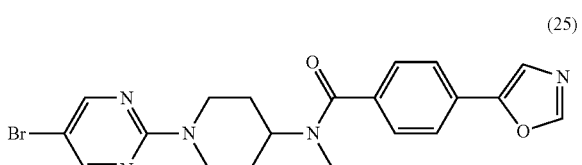
(26)
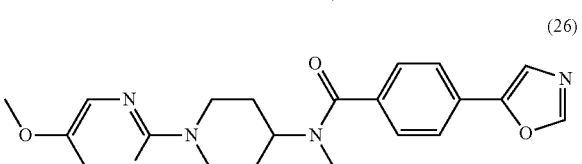
-continued
(27)
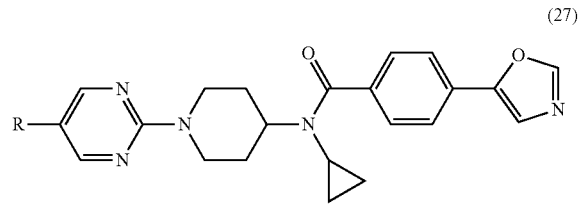
R = 4-methoxyphenyl
(28)
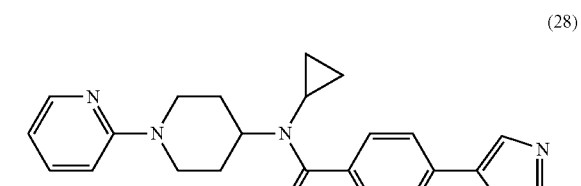
(29)
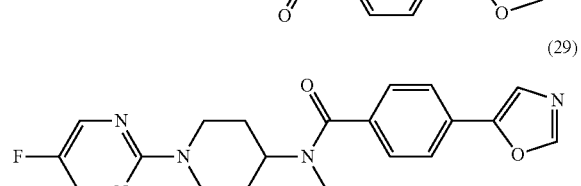
(30)
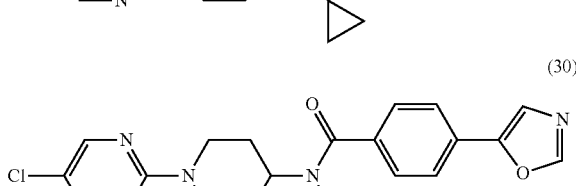
(31)
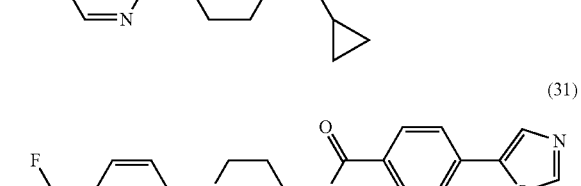
(32)
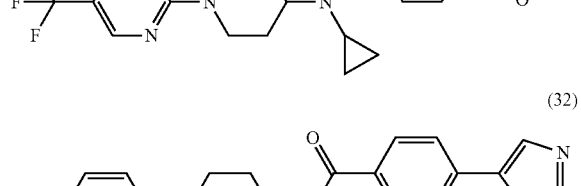
(33)
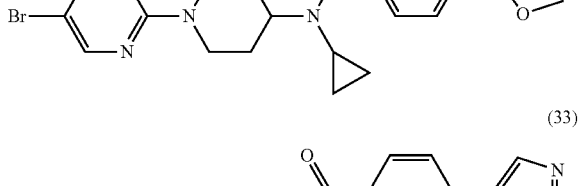
(34)
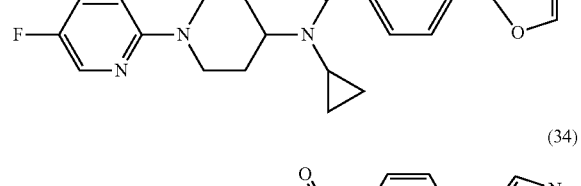

(35)
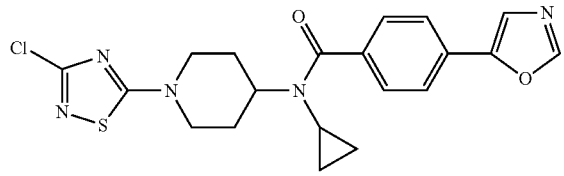
(36)
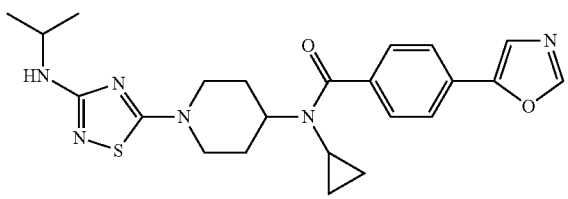
(37)
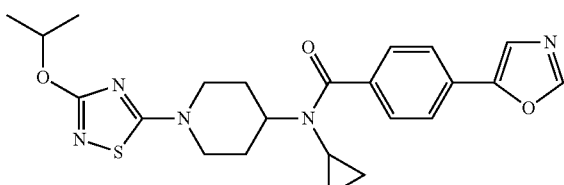
(38)
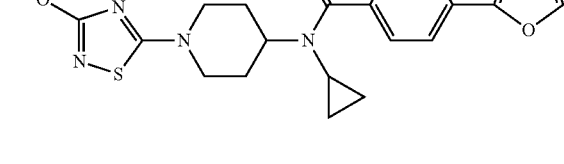
(39)
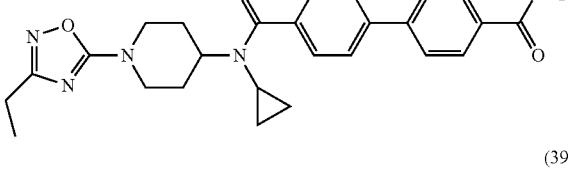
R = phenyl
(40)
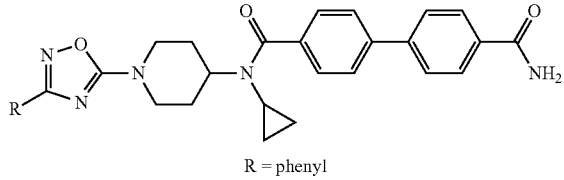
R = 4-bromophenyl
(41)
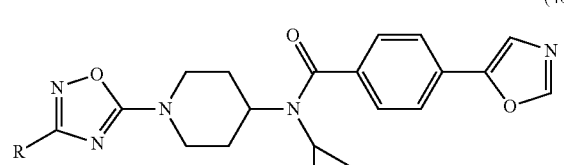
(42)
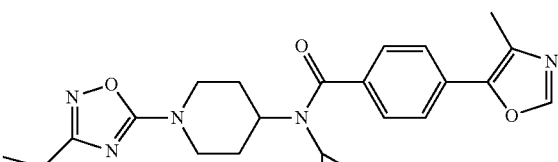
(43)
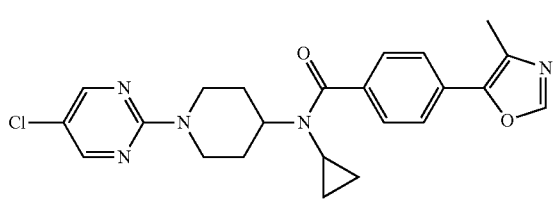
(44)
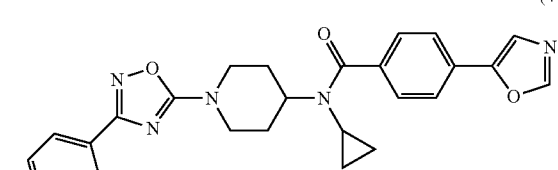
(45)
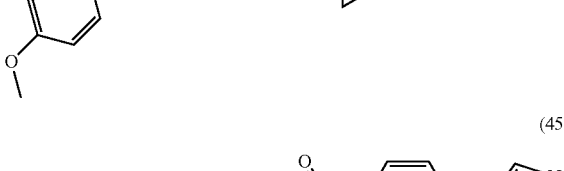
(46)
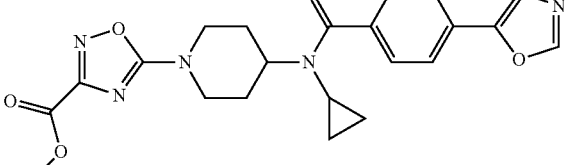
(47)
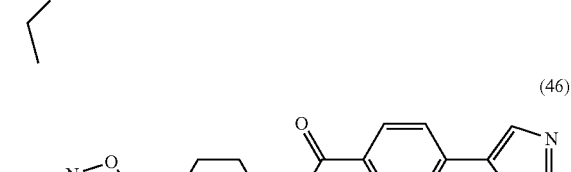
(48)
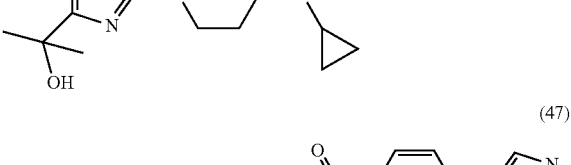

-continued
(49)
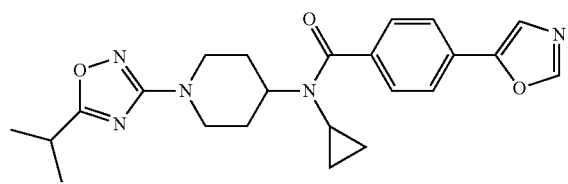
(50)
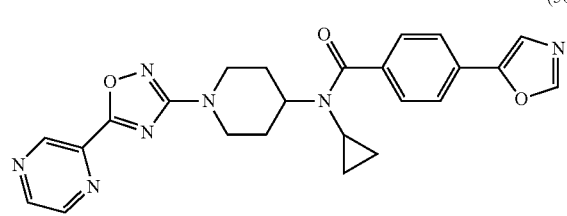
(51)
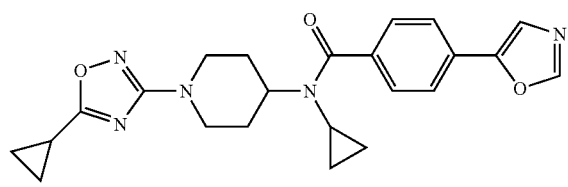
(52)
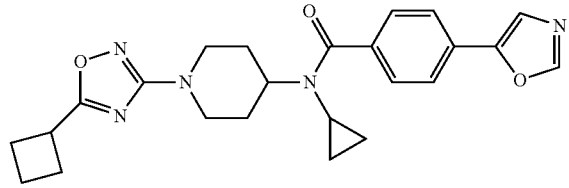
(53)
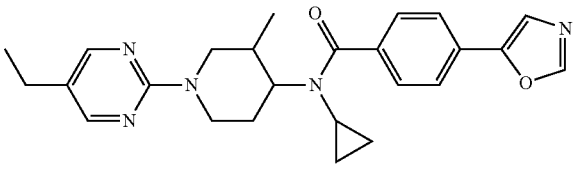
(54)
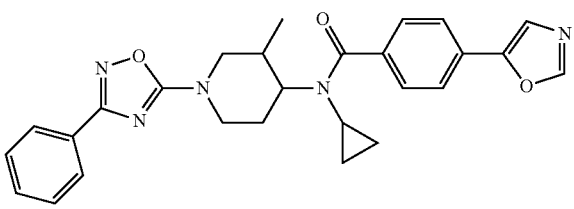
-continued
(55)
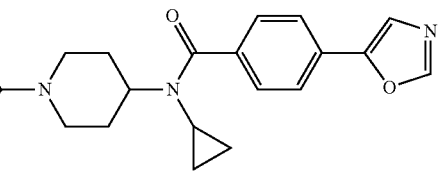
(56)
(57)
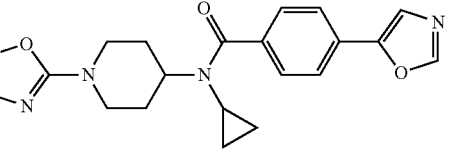
(58)
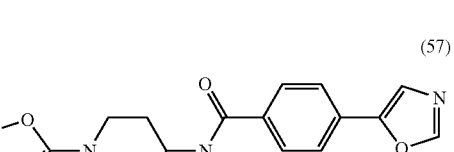
(59)
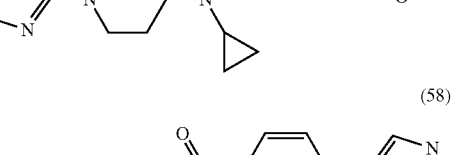
(60)
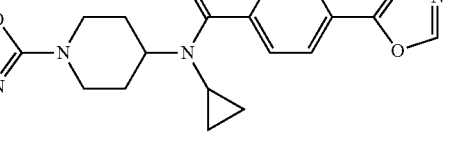
or a salt thereof.
* * * * *

SEQUENCE LISTING

<160> NUMBER OF SEQ ID NOS: 1

<210> SEQ ID NO 1
<211> LENGTH: 358
<212> TYPE: PRT
<213> ORGANISM: artificial
<220> FEATURE:
<223> OTHER INFORMATION: Assay tool

<400> SEQUENCE: 1

```
Met Lys Thr Ile Ile Ala Leu Ser Tyr Ile Phe Cys Leu Val Phe Ala
1               5                   10                  15

Asp Tyr Lys Asp Asp Asp Ala Glu Ser Ser Phe Ser Phe Gly Val
            20                  25                  30

Ile Leu Ala Val Leu Ala Ser Leu Ile Ile Ala Thr Asn Thr Leu Val
                35                  40                  45

Ala Val Ala Val Leu Leu Leu Ile His Lys Asn Asp Gly Val Ser Leu
                50                  55                  60

Cys Phe Thr Leu Asn Leu Ala Val Ala Asp Thr Leu Ile Gly Val Ala
65                  70                  75                  80

Ile Ser Gly Leu Leu Thr Asp Gln Leu Ser Ser Pro Ser Arg Pro Thr
                85                  90                  95

Gln Lys Thr Leu Cys Ser Leu Arg Met Ala Phe Val Thr Ser Ser Ala
                100                 105                 110

Ala Ala Ser Val Leu Thr Val Met Leu Ile Thr Phe Asp Arg Tyr Leu
                115                 120                 125

Ala Ile Lys Gln Pro Phe Arg Tyr Leu Lys Ile Met Ser Gly Phe Val
            130                 135                 140

Ala Gly Ala Cys Ile Ala Gly Leu Trp Leu Val Ser Tyr Leu Ile Gly
145                 150                 155                 160

Phe Leu Pro Leu Gly Ile Pro Met Phe Gln Gln Thr Ala Tyr Lys Gly
                165                 170                 175

Gln Cys Ser Phe Phe Ala Val Phe His Pro His Phe Val Leu Thr Leu
                180                 185                 190

Ser Cys Val Gly Phe Phe Pro Ala Met Leu Leu Phe Val Phe Phe Tyr
                195                 200                 205

Cys Asp Met Leu Lys Ile Ala Ser Met His Ser Gln Gln Ile Arg Lys
210                 215                 220

Met Glu His Ala Gly Ala Met Ala Gly Gly Tyr Arg Ser Pro Arg Thr
225                 230                 235                 240

Pro Ser Asp Phe Lys Ala Leu Arg Thr Val Ser Val Leu Ile Gly Ser
                245                 250                 255

Phe Ala Leu Ser Trp Thr Pro Phe Leu Ile Thr Gly Ile Val Gln Val
                260                 265                 270

Ala Cys Gln Glu Cys His Leu Tyr Leu Val Leu Glu Arg Tyr Leu Trp
            275                 280                 285

Leu Leu Gly Val Gly Asn Ser Leu Leu Asn Pro Leu Ile Tyr Ala Tyr
            290                 295                 300

Trp Gln Lys Glu Val Arg Leu Gln Leu Tyr His Met Ala Leu Gly Val
305                 310                 315                 320

Lys Lys Val Leu Thr Ser Phe Leu Leu Phe Leu Ser Ala Arg Asn Cys
                325                 330                 335

Gly Pro Glu Arg Pro Arg Glu Ser Ser Cys His Ile Val Ala Ile Ala
            340                 345                 350
```

Ser Ser Glu Phe Asp Gly
355